(12) United States Patent
Nakazawa et al.

(10) Patent No.: US 10,351,621 B2
(45) Date of Patent: *Jul. 16, 2019

(54) ANTI-HISTONE THERAPY IN ACUTE KIDNEY INJURY

(71) Applicant: Immunomedics, Inc., Morris Plains, NJ (US)

(72) Inventors: Daigo Nakazawa, Munich (DE); Hans-Joachim Anders, Munich (DE)

(73) Assignee: Immunomedics, Inc., Morris Plains, NJ (US)

( * ) Notice: Subject to any disclaimer, the term of this patent is extended or adjusted under 35 U.S.C. 154(b) by 3 days.

This patent is subject to a terminal disclaimer.

(21) Appl. No.: 15/704,344

(22) Filed: Sep. 14, 2017

(65) Prior Publication Data

US 2018/0057574 A1 Mar. 1, 2018

Related U.S. Application Data

(60) Continuation-in-part of application No. 15/402,585, filed on Jan. 10, 2017, now abandoned, which is a division of application No. 14/746,997, filed on Jun. 23, 2015, now Pat. No. 9,580,495.

(60) Provisional application No. 62/394,529, filed on Sep. 14, 2016, provisional application No. 62/016,277, filed on Jun. 24, 2014.

(51) Int. Cl.
| | |
|---|---|
| *A61K 39/395* | (2006.01) |
| *A61K 38/00* | (2006.01) |
| *A61K 38/16* | (2006.01) |
| *C07K 16/18* | (2006.01) |
| *A61K 38/19* | (2006.01) |
| *C07K 16/24* | (2006.01) |
| *A61K 38/21* | (2006.01) |
| *C07K 16/28* | (2006.01) |
| *A61K 31/727* | (2006.01) |
| *A61K 38/48* | (2006.01) |
| *A61K 38/36* | (2006.01) |
| *A61K 38/20* | (2006.01) |
| *A61K 45/06* | (2006.01) |
| *A61P 13/12* | (2006.01) |
| *A61K 39/00* | (2006.01) |

(52) U.S. Cl.
CPC ............ *C07K 16/18* (2013.01); *A61K 31/727* (2013.01); *A61K 38/19* (2013.01); *A61K 38/191* (2013.01); *A61K 38/193* (2013.01); *A61K 38/20* (2013.01); *A61K 38/21* (2013.01); *A61K 38/366* (2013.01); *A61K 38/4866* (2013.01); *A61K 39/3955* (2013.01); *A61K 45/06* (2013.01); *A61P 13/12* (2018.01); *C07K 16/241* (2013.01); *C07K 16/2896* (2013.01); *A61K 2039/505* (2013.01); *A61K 2300/00* (2013.01); *C07K 2317/21* (2013.01); *C07K 2317/24* (2013.01); *C07K 2317/31* (2013.01); *C07K 2317/54* (2013.01); *C07K 2317/55* (2013.01); *C07K 2317/569* (2013.01); *C07K 2317/622* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,645,493 | B1 | 11/2003 | Bucala et al. |
| 7,312,318 | B2 | 12/2007 | Hansen et al. |
| 8,088,357 | B2 | 1/2012 | Goletz et al. |
| 8,119,101 | B2 | 2/2012 | Byrd et al. |
| 8,716,218 | B2 | 5/2014 | Esmon et al. |
| 2003/0013122 | A1 | 1/2003 | Bucala et al. |
| 2004/0126372 | A1 | 1/2004 | Banerjee et al. |
| 2006/0140936 | A1 | 6/2006 | Goldenberg et al. |
| 2006/0286611 | A1 | 12/2006 | Zempleni et al. |
| 2007/0003543 | A1 | 1/2007 | Datta et al. |

(Continued)

FOREIGN PATENT DOCUMENTS

| | | |
|---|---|---|
| WO | 2009061918 A1 | 5/2009 |
| WO | 2012155039 A1 | 11/2012 |
| WO | 2015200260 | 12/2015 |

OTHER PUBLICATIONS

Chertow et al. 2005. J. Am. Soc. Nephrol. 16:3365-3370 (Year: 2005).*
Allam et al., "Histones from Dying Renal Cells Aggravate Kidney Injury via TLR2 and TLR4", J Am Soc Nephrol. Aug. 2012;23(8):1375-88.
Astiz et al., "Septic shock", Lancet. May 16, 1998;351(9114):1501-5.
Berends et al., "Nuclease expression by *Staphylococcus aureus* facilitates escape from neutrophil extracellular traps", J Innate Immun. 2010;2(6):576-86.

(Continued)

*Primary Examiner* — Shulamith H Shafer
(74) *Attorney, Agent, or Firm* — Richard A. Nakashima

(57) ABSTRACT

Acute kidney injury (AKI) is often associated with damage to remote organs, such as lungs or heart. AKI induces kidney tubular necrosis as well as NETosis, programmed neutrophil death leading to neutrophil extracellular traps (NETs). Histones released during NETosis induces further formation of NETs, which is damaging to renal tissues and remote organs. Circulating trap-forming neutrophils directly injured the lung, while other dead tissue releases contributed to injury in other organs. Suppressing renal necroinflammation using inhibitors of NET formation, tubular cell necrosis or extracellular histones prevented kidney as well as remote organ injuries. Dual inhibition of neutrophil trap formation together with tubular cell necrosis had an additive protective effect. Preferably, damage to remote organs induced by AKI may be treated and/or prevented using anti-histone agents such as anti-histone IgG, recombinant activated protein C, or heparin, alone or in combination with other therapeutic agents, such as PAD inhibitors.

13 Claims, 30 Drawing Sheets

Specification includes a Sequence Listing.

(56) References Cited

U.S. PATENT DOCUMENTS

| | | | |
|---|---|---|---|
| 2009/0117099 A1 | 5/2009 | Esmon et al. | |
| 2012/0231016 A1 | 9/2012 | Tseng et al. | |
| 2013/0287802 A1 | 10/2013 | Govindappa et al. | |
| 2014/0199329 A1 | 7/2014 | Wagner et al. | |
| 2014/0234209 A1 | 8/2014 | Chang et al. | |

OTHER PUBLICATIONS

Bernard et al., "Efficacy and safety of recombinant human activated protein C for severe sepsis", N Engl J Med. Mar. 8, 2001;344(10):699-709.

Bonsib et al., "Glomerular basement membrane discontinuities. Scanning electron microscopic study of acellular glomeruli", Am J Pathol. Jun. 1985;119(3):357-60.

Burger-Kentischer et al., "Expression of macrophage migration inhibitory factor in different stages of human atherosclerosis", Circulation. Apr. 2, 2002;105(13):1561-6.

Calandra et al., "Protection from septic shock by neutralization of macrophage migration inhibitory factor", Nat Med. Feb. 2000;6(2):164-70.

Caudrillier et al., "Platelets induce neutrophil extracellular traps in transfusion-related acute lung injury", J Clin Invest. Jul. 2, 2012;122(7):2661-71.

Chow et al., "Statins enhance formation of phagocyte extracellular traps", Cell Host Microbe. Nov. 18, 2010;8(5):445-54.

Creemers et al., "Epitope recognition in histone H1 by SLE autoantibodies in the presence of a DNA-ligand", Autoimmunity. 1992;12(3):167-74.

De Meyer et al., "Extracellular chromatin is an important mediator of ischemic stroke in mice", Arterioscler Thromb Vasc Biol. Aug. 2012;32(8):1884-91.

Dieker et al., "Mimotopes for lupus-derived anti-DNA and nucleosome-specific autoantibodies selected from random peptide phage display libraries: facts and follies", J Immunol Methods. Jan. 2005;296(1-2):83-93.

Fleming et al., "Accelerated ischemia/reperfusion-induced injury in autoimmunity-prone mice", J Immunol. Sep. 15, 2004;173(6):4230-5.

Fleming et al., "Anti-phospholipid antibodies restore mesenteric ischemia/reperfusion-induced injury in complement receptor 2/complement receptor 1-deficient mice", J Immunol. Dec. 1, 2004;173(11):7055-61.

Frese-Schaper et al., "Reversal of established lupus nephritis and prolonged survival of New Zealand black x New Zealand white mice treated with the topoisomerase I inhibitor irinotecan", J Immunol. Feb. 15, 2010;184(4):2175-82.

Friggeri et al., "Extracellular histones inhibit efferocytosis", Mol Med. Jul. 18, 2012;18:825-33.

Fuchs et al., "Extracellular DNA traps promote thrombosis", Proc Natl Acad Sci U S A. Sep. 7, 2010;107(36):15880-5.

Gillrie et al., "Plasmodium falciparum histones induce endothelial proinflammatory response and barrier dysfunction", Am J Pathol. Mar. 2012;180(3):1028-39.

Jiang et al., "The expression of plasma nucleosomes in mice undergoing in vivo apoptosis", Clin Immunol. Feb. 2003;106(2):139-47.

Kimura et al., "Kinetics of core histones in living human cells: little exchange of H3 and H4 and some rapid exchange of H2B", J Cell Biol. Jun. 25, 2001;153(7):1341-53.

Kramers et al., "Specificity of monoclonal anti-nucleosome autoantibodies derived from lupus mice", J Autoimmun. Dec. 1996;9(6):723-9.

Kumar et al., "Necrotic glomerular cells release histones that trigger glomerular inflammation and crescent formation in glomerulonephritis", Nephrol. Dial. Transplant, vol. 28, No. 1, pp. 46-47 (2013).

Larosa et al., "Immune aspects of sepsis and hope for new therapeutics", Curr Infect Dis Rep. Oct. 2012;14(5):474-83.

Lee et al., "Histone H4 is a major component of the antimicrobial action of human sebocytes", J Invest Dermatol. Oct. 2009;129(10):2489-96.

Leung et al., "Construction and characterization of a humanized, internalizing, B-cell (CD22)-specific, leukemia/lymphoma antibody, LL2", Mol Immunol. Dec. 1995;32(17-18):1413-27.

Monestier et al., "Shared idiotypes and restricted immunoglobulin variable region heavy chain genes characterize murine autoantibodies of various specificities", J Clin Invest. Sep. 1986;78(3):753-9.

Monestier et al., "Monoclonal anti-histone H1 autoantibodies from MRL lpr/lpr mice", Mol Immunol. Aug. 1989;26(8):749-58.

Monestier et al., "Antihistone antibodies in antinuclear antibody-positive juvenile arthritis", Arthritis Rheum. Dec. 1990;33(12):1836-41.

Monestier, M., "Variable region genes of anti-histone autoantibodies from a MRL/Mp-lpr/lpr mouse", Eur J Immunol. Jul. 1991;21(7):1725-31.

Monestier et al., "Antibodies to histones in systemic lupus erythematosus and drug-induced lupus syndromes", Rheum Dis Clin North Am. May 1992;18(2):415-36.

Monestier et al., "Structure and binding properties of monoclonal antibodies to core histones from autoimmune mice", Mol Immunol. Aug. 1993;30(12):1069-75.

Monestier et al., "Induction of anti-polycation antibodies in H-2s mice by immunization with nuclear antigens", Mol Immunol. Jan. 1997;34(1):39-51.

Monestier et al., "Molecular and structural properties of three autoimmune IgG monoclonal antibodies to histone H2B", J Biol Chem. May 5, 2000;275(18):13558-63.

Mostoslavsky et al., "Lupus anti-DNA autoantibodies cross-react with a glomerular structural protein: a case for tissue injury by molecular mimicry", Eur J Immunol. Apr. 2001;31(4):1221-7.

Neeli et al., "Divergent members of a single autoreactive B cell clone retain specificity for apoptotic blebs", Mol Immunol. Mar. 2007;44(8):1914-21.

Olins et al., "The human granulocyte nucleus: Unusual nuclear envelope and heterochromatin composition", Eur J Cell Biol. May 2008;87(5):279-90.

Olins et al., "An epichromatin epitope: persistence in the cell cycle and conservation in evolution", Nucleus. Jan.-Feb. 2011;2(1):47-60.

Prudovsky et al., "Phosphatidylserine colocalizes with epichromatin in interphase nuclei and mitotic chromosomes", Nucleus. Mar. 1, 2012;3(2):200-10.

Radic et al., "Nucleosomes are exposed at the cell surface in apoptosis", J Immunol. Jun. 1, 2004;172(11):6692-700.

Riedemann et al., "The enigma of sepsis", J Clin Invest. Aug. 2003;112(4):460-7.

Rifkin et al., "Immune complexes present in the sera of autoimmune mice activate rheumatoid factor B cells", J Immunol. Aug. 1, 2000;165(3):1626-33.

Salgame et al., "An ELISA for detection of apoptosis", Nucleic Acids Res. Feb. 1, 1997;25(3):680-1.

Toussaint et al., "Immunoglobulins in adult sepsis and septic shock", Curr Infect Dis Rep. Oct. 2012;14(5):522-9.

Ullal et al., "Microparticles as antigenic targets of antibodies to DNA and nucleosomes in systemic lupus erythematosus", J Autoimmun. May 2011;36(3-4):173-80.

Van Amersfoort et al., "Receptors, mediators, and mechanisms involved in bacterial sepsis and septic shock", Clin Microbiol Rev. Jul. 2003;16(3):379-414.

Van Bavel et al., "Apoptosis-associated acetylation on histone H2B is an epitope for lupus autoantibodies", Mol Immunol. Dec. 2009;47(2-3):511-6.

Van Bruggen et al., "Nucleosomes and histones are present in glomerular deposits in human lupus nephritis", Nephrol Dial Transplant. Jan. 1997;12(1):57-66.

Xu et al., "Extracellular histones are mediators of death through TLR2 and TLR4 in mouse fatal liver injury", J Immunol. Sep. 1, 2011;187(5):2626-31.

Yamagata et al., "Clinical findings on ANCA-associated renal vasculitis from the Japan RPGN registry obtained via a questionnaire survey", Clin Exp Nephrol. Oct. 2013;17(5):646-649.

(56) References Cited

OTHER PUBLICATIONS

Yasuda et al., "Requirement for DNA CpG content in TLR9-dependent dendritic cell activation induced by DNA-containing immune complexes", J Immunol. Sep. 1, 2009;183(5):3109-17.
Abrams et al., "Circulating histones are mediators of trauma-associated lung injury", Am J Respir Crit Care Med. Jan. 15, 2013;187(2):160-9.
Allam et al., "Histones trigger sterile inflammation by activating the NLRP3 inflammasome", Eur J Immunol. Dec. 2013;43(12):3336-42.
Allam et al., "Extracellular histones in tissue injury and inflammation", J Mol Med (Berl). May 2014;92(5):465-72.
Arieff et al., "Rapidly progressive glomerulonephritis treated with anticoagulants", Arch Intern Med. Jan. 1972;129(1):77-84.
Basile et al., "Pathophysiology of acute kidney injury", Compr Physiol. Apr. 2012;2(2):1303-53.
Bathe et al., "Neutrophil transit times through pulmonary capillaries: the effects of capillary geometry and fMLP-stimulation", Biophys J. Oct. 2002;83(4):1917-33.
Brinkmann et al., "Neutrophil extracellular traps kill bacteria", Science. Mar. 5, 2004;303(5663):1532-5.
Brown et al., "TLR2 stimulation of intrinsic renal cells in the induction of immune-mediated glomerulonephritis", J Immunol. Aug. 1, 2006;177(3):1925-31.
Brown et al., "Toll-like receptor 4 ligation on intrinsic renal cells contributes to the induction of antibody-mediated glomerulonephritis via CXCL1 and CXCL2", J Am Soc Nephrol. Jun. 2007;18(6):1732-9.
Chaput et al., "Sepsis: the dark side of histones", Nat Med. Nov. 2009;15(11):1245-6.
Chen et al., "The role of high mobility group box 1 (HMGB1) in the pathogenesis of kidney diseases", Acta Pharm Sin B. May 2016;6(3):183-8.
Chen et al., "Release and activity of histone in diseases", Cell Death Dis. Aug. 14, 2014;5:e1370.
Desai et al., "PMA and crystal-induced neutrophil extracellular trap formation involves RIPK1-RIPK3-MLKL signaling", Eur J Immunol. Jan. 2016;46(1):223-9.
Doi et al., "The high-mobility group protein B1-Toll-like receptor 4 pathway contributes to the acute lung injury induced by bilateral nephrectomy", Kidney Int. Aug. 2014;86(2):316-26.
Fuchs et al., "Novel cell death program leads to neutrophil extracellular traps", J Cell Biol. Jan. 15, 2007;176(2):231-41.
Gupta et al., "Efficient neutrophil extracellular trap induction requires mobilization of both intracellular and extracellular calcium pools and is modulated by cyclosporine A", PLoS One. May 12, 2014;9(5):e97088.
Ham et al., "Peptidyl arginine deiminase-4 activation exacerbates kidney ischemia-reperfusion injury", Am J Physiol Renal Physiol. Nov. 1, 2014;307(9):F1052-62.
Hayama et al., "Benefical effect of neutrophil elastase inhibitor on renal warm ischemia-reperfusion injury in the rat", Transplant Proc. Sep. 2006;38(7):2201-2.
Hirsch, JD., "Bactericidal action of histone", J Exp Med. Dec. 1, 1958;108(6):925-44.
Huang et al., "Histones activate the NLRP3 inflammasome in Kupffer cells during sterile inflammatory liver injury", J Immunol. Sep. 1, 2013;191(5):2665-79.
Kambas et al., "Tissue factor expression in neutrophil extracellular traps and neutrophil derived microparticles in antineutrophil cytoplasmic antibody associated vasculitis may promote thromboinflammation and the thrombophilic state associated with the disease", Ann Rheum Dis. Oct. 2014;73(10):1854-63.
Kessenbrock et al., "Netting neutrophils in autoimmune small-vessel vasculitis.", Nat Med. Jun. 2009;15(6):623-5.
Klein et al., "Interleukin-6 mediates lung injury following ischemic acute kidney injury or bilateral nephrectomy", Kidney Int. Oct. 2008;74(7):901-9.
Kramer et al., "Renal ischemia/reperfusion leads to macrophage-mediated increase in pulmonary vascular permeability", Kidney Int. Jun. 1999;55(6):2362-7.
Kumar et al., "Neutrophil Extracellular Trap-Related Extracellular Histones Cause Vascular Necrosis in Severe GN", J Am Soc Nephrol. Oct. 2015;26(10):2399-413.
Kusano et al., "A novel anti-histone H1 monoclonal antibody, SSV monoclonal antibody, improves lung injury and survival in a mouse model of lipopolysaccharide-induced sepsis-like syndrome", Biomed Res Int. 2015;2015:491649.
Lech et al., "Endogenous and exogenous pentraxin-3 limits postischemic acute and chronic kidney injury", Kidney Int. Apr. 2013;83(4):647-61.
Lech et al., "Macrophage phenotype controls long-term AKI outcomes—kidney regeneration versus atrophy", J Am Soc Nephrol. Feb. 2014;25(2):292-304.
Li et al. "PAD4 is essential for antibacterial innate immunity mediated by neutrophil extracellular traps", J Exp Med. Aug. 30, 2010;207(9)1853-62.
Liborio et al., "AKI complications in critically ill patients: association with mortality rates and RRT", Clin J Am Soc Nephrol. Jan. 7, 2015;10(1):21-8.
Linkermann et al., "Two independent pathways of regulated necrosis mediate ischemia-reperfusion injury", Proc Natl Acad Sci U S A. Jul. 16, 2013;110(29):12024-9.
Linkermann et al., "Regulated cell death and inflammation: an auto-amplification loop causes organ failure", Nat Rev Immunol. Nov. 2014;14(11):759-67.
Linkermann et al., "Synchronized renal tubular cell death involves ferroptosis", Proc Natl Acad Sci U S A. Nov. 25, 2014;111(47):16836-41.
Matthijsen et al.,"Myeloperoxidase is critically involved in the induction of organ damage after renal ischemia reperfusion", Am J Pathol. Dec. 2007;171(6):1743-52.
Mulay et al., "Targeting Inflammation in So-Called Acute Kidney Injury", Semin Nephrol. Jan. 2016;36(1):17-30.
Mulay et al., "Necroinflammation in Kidney Disease", J Am Soc Nephrol. Jan. 2016;27(1):27-39.
Nakazawa et al., "Abundant neutrophil extracellular traps in thrombus of patient with microscopic polyangiitis", Front Immunol. Nov. 12, 2012;3:333.
Nakazawa et al., "Intravascular Neutrophil Extracellular Trap (NET) Release Promote Vascular Injury and Tubular Necrosis Upon Ischemia/Reperfusion Injury (IRI) of Kidney", Kidney International Reports, Nov. 2016, vol. 1, Issue 4, pp. S8-S9.
Nakazawa et al., "Intravascular Neutrophil Extracellular Trap (NET) Release Promotes Vascular Injury and Tubular Necrosis Upon Renal Ischemia Reperfusion", Nephrology Dialysis Transplantation, vol. 31, Issue suppl_1, May 1, 2016, pp. i63.
Remijsen et al., "Dying for a cause: NETosis, mechanisms behind an antimicrobial cell death modality", Cell Death Differ. Apr. 2011;18(4):581-8.
Rock et al., "The sterile inflammatory response", Annu Rev Immunol. 2010;28:321-42.
Saffarzadeh et al., "Neutrophil extracellular traps directly induce epithelial and endothelial cell death: a predominant role of histones", PLoS One. 2012;7(2):e32366.
Scheel et al., "Uremic lung: new insights into a forgotten condition", Kidney Int. Oct. 2008;74(7):849-51.
Semeraro et al., "Extracellular histones promote thrombin generation through platelet-dependent mechanisms: involvement of platelet TLR2 and TLR4", Blood. Aug. 18, 2011;118(7):1952-61.
Sharfuddin et al., "Pathophysiology of ischemic acute kidney injury", Nat Rev Nephrol. Apr. 2011;7(4):189-200.
Tsuboi et al., "Roles of toll-like receptors in C—C chemokine production by renal tubular epithelial cells", J lmmunol. Aug. 15, 2002;169(4):2026-33.
Wang et al., "Histone hypercitrullination mediates chromatin decondensation and neutrophil extracellular trap formation", J Cell Biol. Jan. 26, 2009;184(2):205-13.
Ware et al., "The acute respiratory distress syndrome", N Engl J Med. May 4, 2000;342(18):1334-49.

(56) References Cited

OTHER PUBLICATIONS

Wong et al., "Diabetes primes neutrophils to undergo NETosis, which impairs wound healing", Nat Med. Jul. 2015;21(7):815-9.

Xu et al., "Extracellular histones are major mediators of death in sepsis", Nat Med. Nov. 2009;15(11):1318-21.

Yap et al., "Acute kidney injury and extrarenal organ dysfunction: new concepts and experimental evidence", Anesthesiology. May 2012;116(5):1139-48.

* cited by examiner

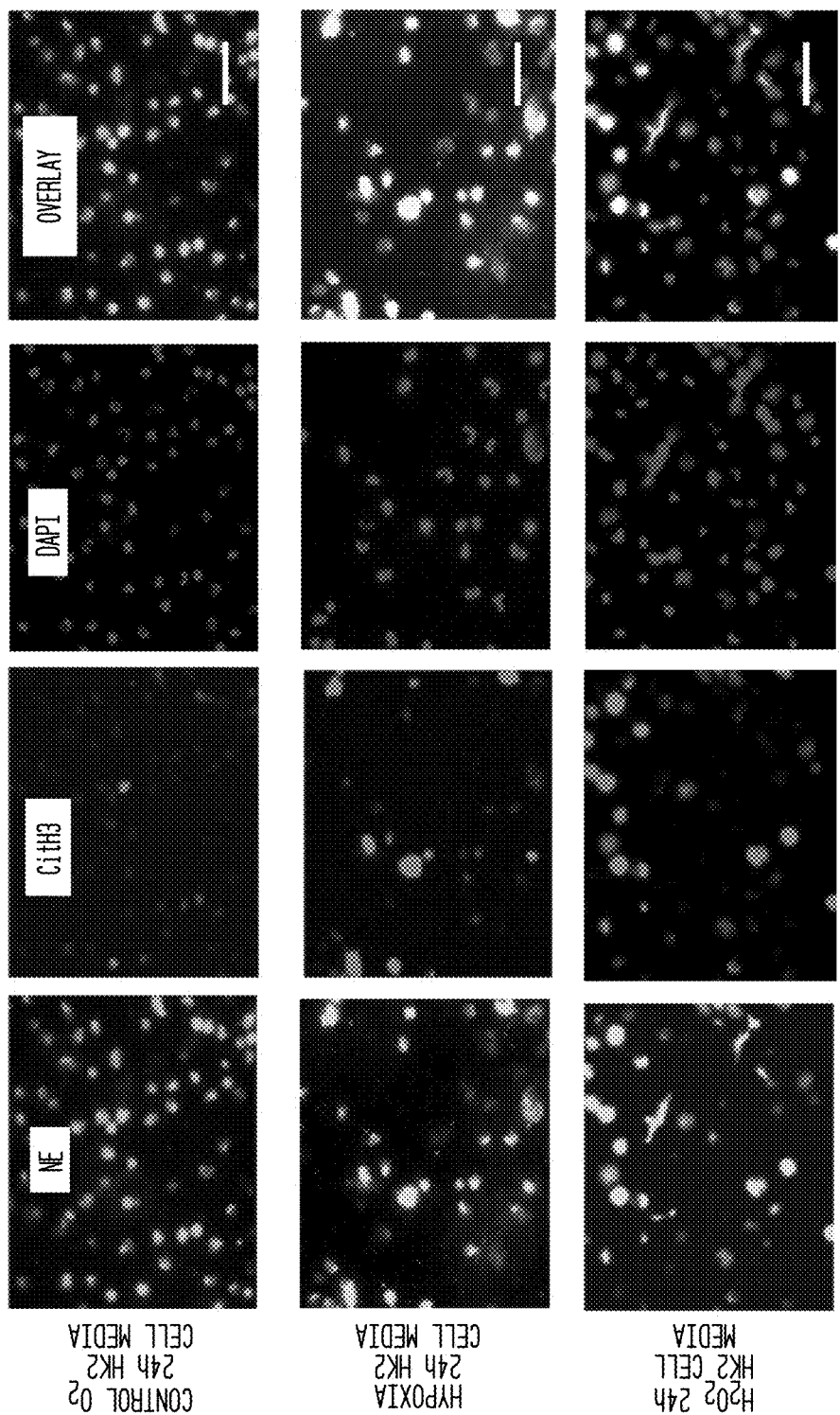

MPO-DNA

MPO-DNA

LDH ASSAY

LANE 1. CONTROL NEUTROPHIL
LANE 2. HYPOXIA NEUTROPHIL
LANE 3. NorO2 HK2 MEDIA -> NEUTROPHIL
LANE 4. HYPOXIA HK2 MEDIA -> NEUTROPHIL
LANE 5. H2O2 HK2 MEDIA -> NEUTROPHIL
LANE 6. PMA (25nM) STIMULATED NEUTROPHIL

Ly6b POSITIVE AREA (%)

CitH3 POSITIVE AREA (%)

TUNEL AREA (%)

TUBULAR INJURY SCORE

TUBULAR INJURY SCORE (PAS)

CIRCULATING NETs

PLASMA CREATININE

PLASMA UREA

Bilateral IRI kidney (I35min, Rep24h)

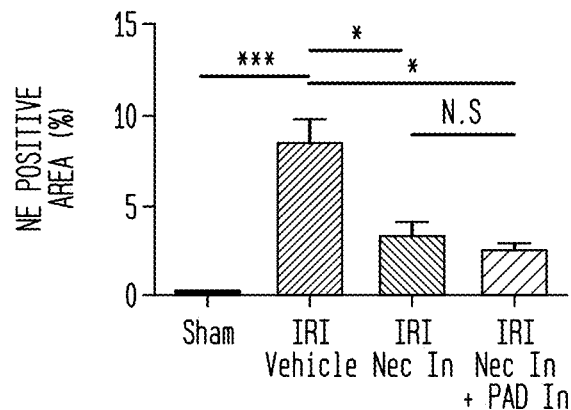
FIG. 5C
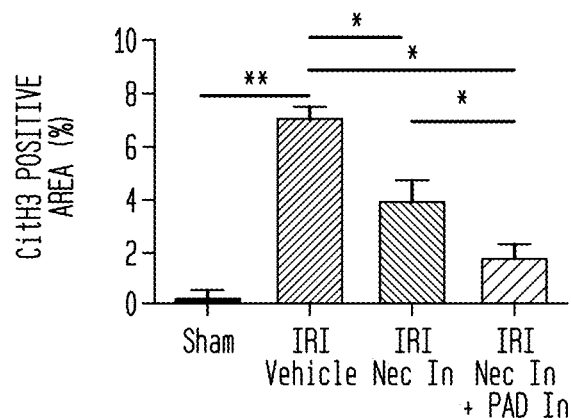
FIG. 5D
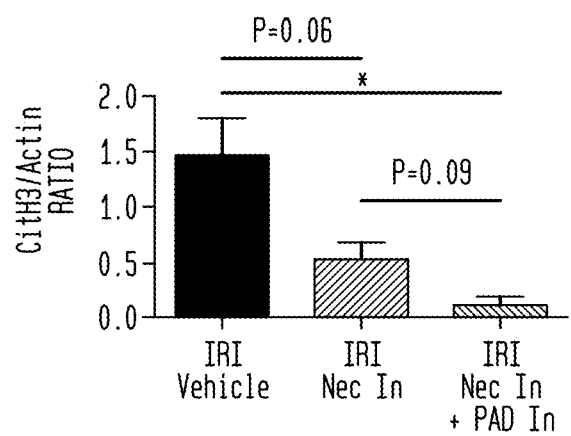

Control neutrophil

Histone-stimulated neutrophil

CitH3/DAPI ratio(%)

- PBS (control)
- Histone
- Histone + conIgG
- Histone + aHisAbs

LDH ASSAY (O.D. 492nm)

- PBS (control)
- Histone
- Histone + conIgG
- Histone + aHisAbs

CitH3 positive area (%)

Necrotic area (%)

TUNEL area (%)

PLASMA CRE (mg/dl)

NETs area in lung

TUNEL area in lung p>0.05, ## p<0.01 compared to histne IgGs

BAL cell number

LIVER

HEART

BRAIN ent application is a continuation-in-part of U.S. patent application Ser. No. 15/402,585, filed Jan. 10, 2017, which was a divisional of U.S. patent application Ser. No. 14/746,997 (now issued U.S. Pat. No. 9,580,495), filed Jun. 23, 2015, which claimed the benefit under 35 U.S.C. 119(e) of provisional U.S. Patent Application Ser. No. 62/016,277, filed Jun. 24, 2014. The text of each priority application is incorporated herein by reference in its entirety.

SEQUENCE LISTING

<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Asp Tyr Leu His
1               5

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Gly Trp Ile Asp Pro Glu Asn Gly Asp Thr Glu Tyr Ala Ser
1               5                   10                  15

Lys Phe Gln Gly
            20

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Leu Val His Leu Arg Thr Phe Ala Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Glu Ser Val Asp Ser Tyr Asp Asn Ser Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Ser Asn Leu Glu Ser
1               5

<210> SEQ ID NO 6
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 6

Gln Gln Asn Asn Glu Asp Pro Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Tyr Trp Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Ile Asp Pro Ser Asp Ser Glu Thr His Tyr Asn Gln Lys Phe Lys
1               5                   10                  15

Asp

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Lys Ile Thr Asp Asp Tyr Asn Tyr Phe Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Glu Ser Val Asp Ser Tyr Gly Asn Ser Phe Met His
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
His Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Asn Asn Glu Asp Pro Leu Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Tyr Val Met Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ile Asn Pro Tyr Asn Asp Gly Thr Lys Tyr Asn Glu Lys Phe Lys
1               5                   10                  15

Gly

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Gly Asp Gly Tyr Pro Phe Asp Tyr
1               5

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Ser Gln Ser Ile Val His Ser Asn Gly Asn Thr Tyr Leu Glu
1               5                   10                  15

<210> SEQ ID NO 17
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 17

Lys Val Ser Asn Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Gln Gly Ser His Val Pro Tyr Thr
1               5

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ile Glu Tyr Leu Ala Lys Gln Ile Val Asp Asn Ala Ile Gln Gln
1               5                   10                  15

Ala
```

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 23
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 24
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Gly Phe Glu Glu Leu Ala Trp Lys Ile Ala Lys Met Ile Trp Ser
1               5                   10                  15

Asp Val Phe Gln Gln Gly Cys

20

<210> SEQ ID NO 26
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
        50

<210> SEQ ID NO 27
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
        50

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Gly Phe Ala Leu
            20                  25                  30

Gln His Phe Thr Arg Leu Gln Gln Glu Asn Glu Arg
        35                  40
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Gln Ile Glu Tyr Val Ala Lys Gln Ile Val Asp Tyr Ala Ile His Gln
1               5                   10                  15

Ala
```

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Glu Phe Pro Lys Pro Ser Thr Pro Pro Gly Ser Ser Gly Gly Ala Pro
1               5                   10                  15
```

<210> SEQ ID NO 32
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
            180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 327
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 35
<211> LENGTH: 106
<212> TYPE: PRT
<213> ORGANISM: Homo sapiens

<400> SEQUENCE: 35

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agggcctcac taaaccatcc                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcaattattc cccatgaacg                                              20

<210> SEQ ID NO 38
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccaccacgct cttctgtcta c                                              21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agggtctggg ccatagaact                                                20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aggggtaact ctgtaggccc                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaacacatgc agtcacagcc                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catccctcgt ctcccattta                                                20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tatccgagtt ggggaaatca                                                20

<210> SEQ ID NO 44
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 44
agcggcaggt tacattcaaa                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caagttttgg tggcacacag                                               20
```

ANTI-HISTONE THERAPY IN ACUTE KIDNEY INJURY

RELATED APPLICATIONS

This application claims the benefit under 35 U.S.C. 119(e) of provisional U.S. Patent Application Ser. No. 62/394,529, filed Sep. 14, 2016. The present application is a continuation-in-part of U.S. patent application Ser. No. 15/402,585, filed Jan. 10, 2017, which was a divisional of U.S. patent application Ser. No. 14/746,997 (now issued U.S. Pat. No. 9,580,495), filed Jun. 23, 2015, which claimed the benefit under 35 U.S.C. 119(e) of provisional U.S. Patent Application Ser. No. 62/016,277, filed Jun. 24, 2014. The text of each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 13, 2017 is named IMM346US3_SL.txt and is 22,779 bytes in size.

FIELD OF THE INVENTION

The invention relates to compositions and methods of use of histone-neutralizing agents, such as anti-histone IgG, activated protein C, and heparin, or PAD inhibitors for treatment of remote organ injury induced by acute kidney injury. Remote organ injury refers to injury to nonrenal organs, for example the lungs and heart. In certain preferred embodiments, the histone-neutralizing agent is an anti-histone antibody or antigen-binding fragment thereof, such as the BWA-3 anti-H4 antibody. In other embodiments, the anti-histone antibodies bind to human histones H2B, H3 or H4. More particular embodiments may concern chimeric or more preferably humanized forms of anti-histone antibodies. However, any other known histone-neutralizing agent may be utilized for treating remote organ injury induced by acute kidney injury. In alternative embodiments, a PAD inhibitor may be Cl amidine, although other known PAD inhibitors such as o-F-amidine, o-Cl-amidine, TDFA (Thr-Asp-F-amidine), YW3-56 or streptonigrin (Bicker & Thompson, 2013, Biopolymers 99:155-63) may be utilized.

BACKGROUND

Acute kidney injury (AKI) is a common problem in both tertiary care centers as well as in the developing world. AKI often arises from injuries such as trauma, severe infection, sepsis, medications and contrast agents, or following major surgery. AKI is common among patients requiring intensive care on hospital admission, often requiring the use of dialysis. Renal failure is often associated with damage to remote (nonrenal) organs, particularly the lungs, with increased pulmonary vascular permeability and pulmonary hemorrhage (Kramer et al., 1999, Kidney Int. 55:2362-7).

Acute kidney injury involves cell necrosis as well as NETosis, a programmed neutrophil death leading to expulsion of nuclear chromatin leading to neutrophil extracellular traps (NETs). ETosis is a programmed form of cell death of mostly neutrophils (referred to as NETosis) and other granulocytes (Brinkmann et al., 2004, Science 303:1532). NETosis causes an explosion-like directed expulsion of chromatin generating a meshwork called neutrophil extracellular traps (NETs), which immobilize and kill bacteria during infections (Brinkmann et al., 2004, Science 303:1532). Cytokine-induced NETosis also drives sterile injury including necrotizing GN (Kessenbrock et al., 2009, Nat Med 15:623; Kambas et al., 2013, Ann Rheum Dis 73:1854; Nakazawa et al., 2012, Front Immunol 3:333; Tsuboi et al., 2002, J Immunol 169:2026). Many cytosolic or chromatin-related components could account for the toxic and pro-inflammatory effect of NETs, such as proteolytic enzymes or intracellular molecules with immunostimulatory effects, referred to as danger-associated molecular patterns (DAMPs) (Rock et al., 2010, Annual Review of Immunology 28:321).

Histones are nuclear proteins that wind up the double-stranded DNA to form chromatin. Dynamic modifications of histone residues regulate gene transcription by determining the accessibility of transcription factors to their DNA binding sites (Helin & Dhanak, 2013, Nature 502:480). When cell necrosis releases histones into the extracellular space they display significant cytotoxic effects (Hirsch, 1958, J Exp Med 108:925; Xu et al., 2009, Nat Med 15:1318; Chaput & Zychlinsky, 2009, Nat Med 15:1245; Allam et al., 2014, J Mol Med 92:465). Histones contribute to fatal outcomes in murine endotoxinemia caused by microvascular injury and activation of coagulation (Xu et al., 2009, Nat Med 15:1318; Abrams et al., 2013, Am J Respir Crit Care Med 187:160; Saffarzadeh et al., 2012, PLoS One 7:e32366; Semeraro et al., 2011, Blood 118:1952). Dying renal cells release extracellular histones that promote septic and post-ischemic acute kidney injury (Allam et al., 2012, J Am Soc Nephrol 23:1375). Further, histones act as DAMPs by activating Toll-like receptor (TLR)-2 and -4 as well as NLRP3 (Allam et al., 2012, J Am Soc Nephrol 23:1375; Allam et al., 2013, Eur J Immunol 43:3336; Semeraro et al., 2011, Blood 118:1952; Huang et al., 2013, J Immunol 191:2665; Xu et al., 2011, J Immunol 187:2626). TLR2/-4-mediated pathology is an essential mechanism of crescentic GN (Brown et al., 2006, J Immunol 177:1925; Brown et al., 2007, J Am Soc Nephrol 18:1732).

A need exists for improved methods and compositions for treatment of remote organ injury induced by acute kidney injury, preferably using histone-neutralizing agents such as anti-histone antibodies or fragments thereof, or agents that inhibit post-translational modification of histones, such as PAD (peptidyl arginine deiminase) inhibitors (Bicker & Thompson, 2013, Biopolymers 99:155-63).

SUMMARY

The present invention concerns compositions and methods of anti-histone therapy for remote organ injury induced by acute kidney injury. Preferably the anti-histone therapy may involve use of agents such as activated protein C, heparin, or anti-histone antibodies, such as antibodies against histone H2B, H3 or H4. In more preferred embodiments, the anti-histone antibody may be a BWA-3 anti-H4 antibody (see, e.g., U.S. patent application Ser. No. 14/620, 315, the Examples section and Figures of which are incorporated herein by reference). In alternative embodiments, PAD (peptidyl arginine deiminase) inhibitors may be utilized alone or in combination with other histone inhibitors.

Preferably, the anti-histone antibodies or fragments thereof may be chimeric, humanized or human. The antibody can be of various isotypes, preferably human IgG1, IgG2, IgG3 or IgG4, more preferably comprising human IgG1 hinge and constant region sequences. Most preferably, the antibody or fragment thereof may be designed or selected to comprise human constant region sequences that belong to specific allotypes, which may result in reduced immunogenicity when the immunoconjugate is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes. Exemplary humanized anti-histone antibodies are disclosed in U.S. patent application Ser. No. 14/620,315, the Figures and Examples section of which are incorporated herein by reference.

In certain preferred embodiments, a combination of anti-histone antibodies may be used. Antibodies against human histones H1, H2A, H2B, H3 or H4 may be used in any combination. Other non-antibody therapeutic agents targeted against either histones or downstream effectors of a histone-mediated pathway may also be utilized in combination with anti-histone antibodies or fragments thereof, administered either before, simultaneously with, or following administration of one or more anti-histone antibodies or fragments thereof. Various therapeutic agents of use in treating histone-associated diseases are known in the art, such as activated protein C (APC), thrombomodulin, a peptide fragment of histone H1, H2A, H2B, H3 or H4, granzyme A, granzyme B, plasmin, Factor 7-activating protease, heparin, Cl-amidine and any such known agent may be utilized in combination with anti-histone antibodies or antibody fragments. A human histone H4 peptide may comprise residues 50-67 or 40-78 of human H4 (see, e.g., U.S. Publ. No. 20090117099). Depending on the underlying etiology, the anti-histone agents may also be utilized in combination with one or more standard treatments for acute kidney injury, such as corticosteroids, immune-suppressing drugs or plasmapheresis.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 2A. NETs initiate the loop of necroinflammation in vitro. The media of human induced tubular epithelial cells (iTECs) treated with normal oxygen, hypoxia (1% $O_2$) or 10 mM $H_2O_2$ for 24 hours, were applied to healthy human neutrophils. After 4 hours of incubation, the NETs were detected by immunofluorescence staining. NE: Green, CitH3: Red, DAPI staining: Blue. Scale Bar: 50 µm.

FIG. 5C. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Left graph show NE positive area and right graph show CitH3 positive area.

FIG. 5D. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Quantification of protein expression, normalized to β-actin expression.

DETAILED DESCRIPTION OF THE INVENTION

Definitions

Figure 1A:
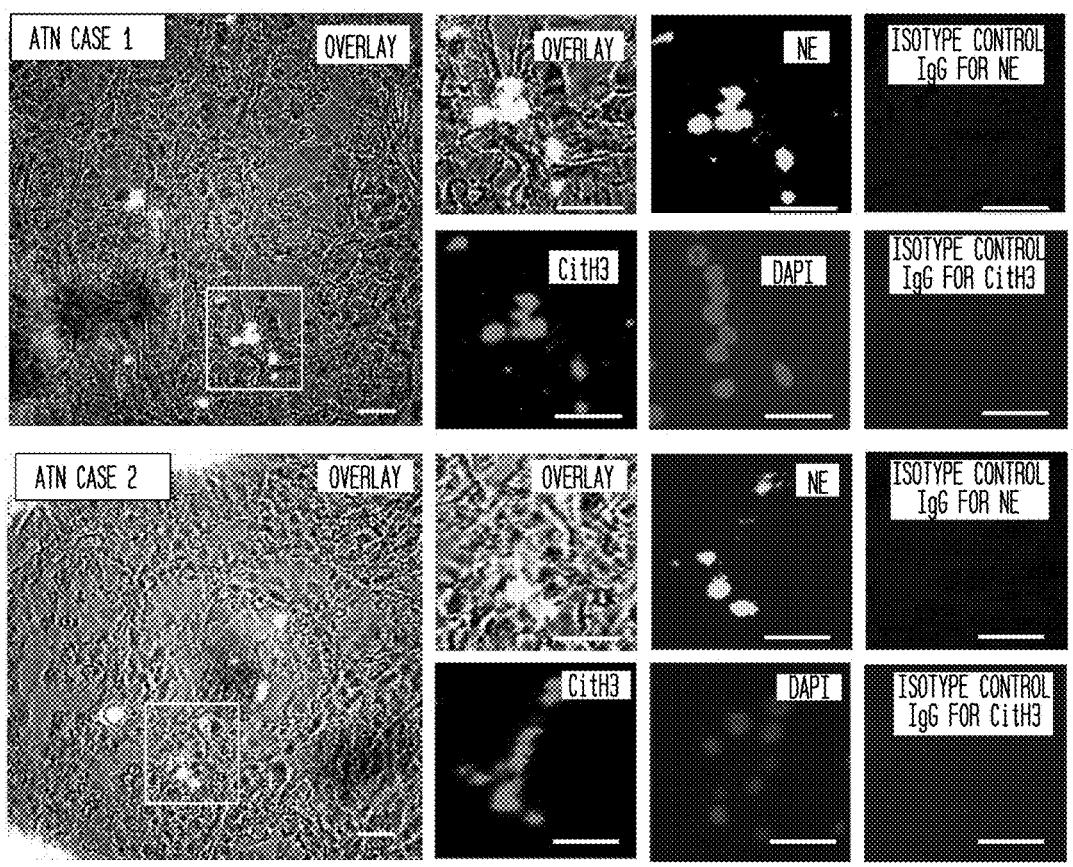
FIG. 1A. NETs evidence in 2 patients with acute tubular necrosis (ATN) after kidney transplantation. Representative NETs immunostaining in 2 human kidney biopsy samples with severe ATN. Neutrophil elastase (NE): Green, citrullinated histone 3(CitH3): Red, DAPI staining: Blue and overlay with phase contrast. The staining by isotype control IgG for NE and CitH3 was conducted (Right figure). NE/CitH3 positive NETs are detected in tubular-interstitium space (Upper figures: Case 1, Lower figures: Case 2). Scale Bar: 25 µm.

In the description that follows, a number of terms are used and the following definitions are provided to facilitate understanding of the claimed subject matter. Terms that are not expressly defined herein are used in accordance with their plain and ordinary meanings.

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MM).

An "antibody" as used herein refers to a full-length (i.e., naturally occurring or formed by normal immunoglobulin gene fragment recombinatorial processes) immunoglobulin molecule (e.g., an IgG antibody). An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as $F(ab')_2$, $F(ab)_2$, Fab', Fab, Fv, sFv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb). Fragments of antibodies that do not bind to the same antigen as the intact antibody, such as the Fc fragment, are not included within the scope of an "antibody fragment" as used herein.

A "chimeric antibody" is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A "humanized antibody" is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A "human antibody" is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, human antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples section of each of which is incorporated herein by reference.

An "immunoconjugate" is an antibody, antigen-binding antibody fragment, antibody complex or antibody fusion protein that is conjugated to a therapeutic agent. Conjugation may be covalent or non-covalent. Preferably, conjugation is covalent.

As used herein, the term "antibody fusion protein" is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An "immunomodulator" is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation. Exemplary interferons include interferon-α, interferon-β, interferon-γ and interferon-λ.

An anti-histone antibody or antibody fragment, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of an autoimmune disease state. A physiologically significant effect could also be the evocation of a humoral and/or cellular immune response in the recipient subject leading to growth inhibition or death of target cells.

Anti-Histone Antibodies

Various anti-histone antibodies and/or antigen-binding fragments thereof may be of use. The murine BWA-3 (anti-H4), LG2-1 (anti-H3) and LG2-2 (anti-H2B) hybridomas were reported by Monestier et al. (1993, Mol. Immunol 30:1069-75). However, murine antibodies are generally not appropriate for human therapeutic use, due to the formation of human anti-mouse antibodies (HAMA) that can neutralize these antibodies and thus make them less active.

In preferred embodiments, a humanized or chimeric anti-histone H4 antibody is one that comprises the heavy chain complementarity-determining region (CDR) sequences CDR1 (DDYLH, SEQ ID NO:1), CDR2 (WIGWIDPENGDTEYASKFQG, SEQ ID NO:2) and CDR3 (PLVHLRTFAY, SEQ ID NO:3) and the light chain CDR sequences CDR1 (RASESVDSYDNSLH, SEQ ID NO:4), CDR2 (LASNLES, SEQ ID NO:5) and CDR3 (QQNNEDPWT, SEQ ID NO:6). (See, e.g., U.S. Pat. No. 8,987,421, the Figures and Examples section of which are incorporated herein by reference.)

In other preferred embodiments, a humanized or chimeric anti-histone H3 antibody is one that comprises the heavy chain CDR sequences CDR1 (SYWMH, SEQ ID NO:7), CDR2 (NIDPSDSETHYNQKFKD, SEQ ID NO:8) and CDR3 (EKITDDYNYFDY, SEQ ID NO:9) and the light chain CDR sequences CDR1 (RASESVDSYGNSFMH, SEQ ID NO:10), CDR2 (HASNLES, SEQ ID NO:11) and CDR3 (QQNNEDPLT, SEQ ID NO:12) (see, e.g., U.S. Pat. No. 8,987,421).

In still other preferred embodiments, a humanized or chimeric anti-histone H2B antibody is one that comprises the heavy chain CDR sequences CDR1 (SYVMY, SEQ ID NO:13), CDR2 (YINPYNDGTKYNEKFKG, SEQ ID NO:14) and CDR3 (PGDGYPFDY, SEQ ID NO:15) and the light chain CDR sequences CDR1 (RSSQSIVHSNGNTYLE, SEQ ID NO:16), CDR2 (KVSNRFS, SEQ ID NO:17) and CDR3 (FQGSHVPYT, SEQ ID NO:18) (see, e.g., U.S. Pat. No. 8,987,421).

General Techniques for Antibodies and Antibody Fragments

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). The person of ordinary skill may readily produce antibodies against any known and characterized target antigen, using only routine experimentation. Known antigens that may be targeted include, but are not limited to, human histone H4 (e.g., NCBI Ref. No. NP_778224.1), human histone H3 (e.g., GenBank Ref. No. CAB02546.1) or human histone H2B (e.g., GenBank Ref. No. CAB02542.1)

Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Phamacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, J. Mol. Biol. 222:581-97). Library construction was performed according to Andris-Widhopf et al. (2000, In: Phage Display Laboratory Manual, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999,

*J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, *Science*, 246:1274-1281) to allow rapid and easy identification of monoclonal Fab' fragments with the desired specificity. F(ab)$_2$ fragments may be generated by papain digestion of an antibody.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. Nos. 4,704,692, 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991).

Techniques for producing single domain antibodies are also known in the art, as disclosed for example in Cossins et al. (2006, Prot Express Purif 51:253-259), incorporated herein by reference. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). In certain embodiments, anti-pancreatic cancer VHH antibody fragments may be utilized in the claimed compositions and methods.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys*. 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572, 856; 6,566,076; 6,562,618; 6,545,130; 6,544,749; 6,534, 058; 6,528,625; 6,528,269; 6,521,227; 6,518,404; 6,511, 665; 6,491,915; 6,488,930; 6,482,598; 6,482,408; 6,479, 247; 6,468,531; 6,468,529; 6,465,173; 6,461,823; 6,458, 356; 6,455,044; 6,455,040, 6,451,310; 6,444,206; 6,441, 143; 6,432,404; 6,432,402; 6,419,928; 6,413,726; 6,406, 694; 6,403,770; 6,403,091; 6,395,276; 6,395,274; 6,387, 350; 6,383,759; 6,383,484; 6,376,654; 6,372,215; 6,359, 126; 6,355,481; 6,355,444; 6,355,245; 6,355,244; 6,346, 246; 6,344,198; 6,340,571; 6,340,459; 6,331,175; 6,306, 393; 6,254,868; 6,187,287; 6,183,744; 6,129,914; 6,120, 767; 6,096,289; 6,077,499; 5,922,302; 5,874,540; 5,814, 440; 5,798,229; 5,789,554; 5,776,456; 5,736,119; 5,716, 595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use include, but are not limited to, LL1 (anti-CD74), LL2 and RFB4 (anti-CD22), MN-14 (anti-carcinoembryonic antigen (CEA, also known as CD66e), hL243 (anti-HLA-DR), alemtuzumab (anti-CD52), gemtuzumab (anti-CD33), ibritumomab tiuxetan (anti-CD20); rituximab (anti-CD20); tositumomab (anti-CD20); and GA101 (anti-CD20). Such antibodies are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hA20 (U.S. Pat. No. 7,151,164), hA19 (U.S. Pat. No. 7,109,304), hLL1 (U.S. Pat. No. 7,312,318,), hLL2 (U.S. Pat. No. 5,789,554), hL243 (U.S. Pat. No. 7,612,180), hMN-14 (U.S. Pat. No. 6,676,924), hMN-15 (U.S. Pat. No. 8,287,865), and hMN-3 (U.S. Pat. No. 7,541,440), the text of each recited patent or application is incorporated herein by reference with respect to the Figures and Examples sections.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD1 la); muromonab-CD3 (anti-CD3 receptor); anti-CD40L (UCB, Brussels, Belgium); natalizumab (anti-α4 integrin) and omalizumab (anti-IgE).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as autoimmune diseases like rheumatoid arthritis and systemic lupus erythematosus (Morand & Leech, 2005, Front Biosci 10:12-22; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

Bispecific and Multispecific Antibodies

Bispecific or multispecific antibodies can be prepared by a variety of procedures, ranging from glutaraldehyde linkage to more specific linkages between functional groups. The antibodies and/or antibody fragments are preferably covalently bound to one another, directly or through a linker moiety, through one or more functional groups on the antibody or fragment, e. g., amine, carboxyl, phenyl, thiol, or hydroxyl groups. Various conventional linkers in addition to glutaraldehyde can be used, e. g., disiocyanates, diiosothiocyanates, bis (hydroxysuccinimide) esters, carbodiimides, maleimidehydroxy-succinimde esters, and the like. The optimal length of the linker may vary according to the type of target cell.

A simple method to produce multivalent antibodies is to mix the antibodies or fragments in the presence of glutaraldehyde. The initial Schiff base linkages can be stabilized, e. g., by borohydride reduction to secondary amines. A diiosothiocyanate or carbodiimide can be used in place of glutaraldehyde as a non-site-specific linker.

The simplest form of a multivalent, multispecific antibody is a bispecific antibody. Bispecific antibodies can be made by a variety of conventional methods, e. g., disulfide cleavage and reformation of mixtures of whole IgG or, preferably F (ab')$_2$ fragments, fusions of more than one hybridoma to form polyomas that produce antibodies having more than one specificity, and by genetic engineering. Bispecific antibodies have been prepared by oxidative cleavage of Fab' fragments resulting from reductive cleavage of different antibodies. This is advantageously carried out by mixing two different F (ab')$_2$ fragments produced by pepsin digestion of two different antibodies, reductive cleavage to form a mixture of Fab' fragments, followed by oxidative reformation of the disulfide linkages to produce a mixture of F (ab')$_2$ fragments including bispecific antibodies containing a Fab' portion specific to each of the original epitopes. General techniques for the preparation of multivalent antibodies may be found, for example, in Nisonhoff et al., Arch Biochem. Biophys. 93: 470 (1961) Hammerling et al., J. Exp. Med. 128: 1461 (1968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e. g., an antibody Fab fragment having free sulfhydryl groups (or, a larger fragment or intact antibody with sulfhydryl groups appended thereto by, e. g., Train's Reagent. Such a linker is less likely to crosslink groups in the same antibody and improves the selectivity of the linkage.

It is advantageous to link the antibodies or fragments at sites remote from the antigen binding sites. This can be accomplished by, e. g., linkage to cleaved interchain sulfhydryl groups, as noted above. Another method involves reacting an antibody having an oxidized carbohydrate portion with another antibody which has at least one free amine function. This results in an initial Schiff base (imine) linkage, which is preferably stabilized by reduction to a secondary amine, e. g., by borohydride reduction, to form the final product. Such site-specific linkages are disclosed, for small molecules, in U.S. Pat. No. 4,671,958, and for larger addends in U.S. Pat. No. 4,699,784.

Alternatively, such bispecific antibodies can be produced by fusing two hybridoma cell lines that produce appropriate Mabs. Techniques for producing tetradomas are described, for example, by Milstein et al., *Nature* 305: 537 (1983) and Pohl et al., *Int. J. Cancer* 54: 418 (1993).

Alternatively, chimeric genes can be designed that encode both binding domains. General techniques for producing bispecific antibodies by genetic engineering are described, for example, by Songsivilai et al., *Biochem Biophys Res. Commun* 164: 271 (1989); Traunecker et al., *EMBO J.* 10: 3655 (1991); and Weiner et al., *J. Immunol.* 147: 4035 (1991).

A higher order multivalent, multispecific molecule can be obtained by adding various antibody components to a bispecific antibody, produced as above. For example, a bispecific antibody can be reacted with 2-iminothiolane to introduce one or more sulfhydryl groups for use in coupling the bispecific antibody to a further antibody derivative that binds the same or a different epitope of the target antigen, using the bis-maleimide activation procedure described above. These techniques for producing multivalent antibodies are well known to those of skill in the art. See, for example, U.S. Pat. No. 4,925,648, and Goldenberg, international publication No. WO 92/19273, which are incorporated by reference.

DOCK-AND-LOCK® (DNL®)

In preferred embodiments, a bispecific or multispecific antibody is formed as a DOCK-AND-LOCK® (DNL®) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264. Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL® complex comprises a trimer with two DDD-linked molecules attached to one AD-linked molecule, variations in complex structure allow the formation of dimers, trimers, tetramers, pentamers, hexamers and other multimers. In some embodiments, the DNL® complex may comprise two or more antibodies, antibody fragments or fusion proteins which bind to the same antigenic determinant or to two or more different antigens. The DNL® complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (RI and RII), and each type has $\alpha$ and $\beta$ isoforms (Scott, *Pharmacol. Ther.* 1991; 50:123). Thus, the four isoforms of PKA regulatory subunits are RI$\alpha$, RII$\beta$, RII$\alpha$ and RIII$\beta$. The R subunits have been isolated only as stable dimers and the dimerization domain has been shown to consist of the first 44 amino-terminal residues of RII$\alpha$ (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci USA.* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell Biol.* 2004; 5:959). The AD of AKAPs for PKA is an amphipathic helix of 14-18 residues (Carr et al., *J. Biol. Chem.* 1991; 266:14188). The amino acid sequences of the AD are quite varied among individual AKAPs, with the binding affinities reported for RII dimers ranging from 2 to 90 nM (Alto et al., *Proc. Natl. Acad. Sci. USA.* 2003; 100:4445). AKAPs will only bind to dimeric R subunits. For human RII$\alpha$, the AD binds to a hydrophobic surface formed by the 23 amino-terminal residues (Colledge and Scott, *Trends Cell Biol.* 1999; 6:216). Thus, the dimerization domain and AKAP binding domain of human RII$\alpha$ are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL® complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA.* 2001; 98:8480) to ligate site-specifically. Using various combinations of linkers, adaptor modules and precursors, a wide variety of DNL® constructs of different stoichiometry may be produced and used (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL® constructs, different AD or DDD sequences may be utilized. Exemplary DDD and AD sequences are provided below.

```
DDD1
                                          (SEQ ID NO: 19)
SHIQIPPGLTELLQGYTVEVLRQQPPDLVEFAVEYFTRLREARA

DDD2
                                          (SEQ ID NO: 20)
CGHIQIPPGLTELLQGYTVEVLRQQPPDLVEFAVEYFTRLREARA

AD1
                                          (SEQ ID NO: 21)
QIEYLAKQIVDNAIQQA

AD2
                                          (SEQ ID NO: 22)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                          (SEQ ID NO: 23)
SLRECELYVQKHNIQALLKDSIVQLCTARPERPMAFLREYFERLEKEEAK

DDD3C
                                          (SEQ ID NO: 24)
MSCGGSLRECELYVQKHNIQALLKDSIVQLCTARPERPMAFLREYFERLE
KEEAK

AD3
                                          (SEQ ID NO: 25)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                          (SEQ ID NO: 26)
SLRECELYVQKHNIQALLKDVSIVQLCTARPERPMAFLREYFEKLEKEEA
K

PKA RIβ
                                          (SEQ ID NO: 27)
SLKGCELYVQLHGIQQVLKDCIVHLCISKPERPMKFLREHFEKLEKEENR
QILA

PKA RIIα
                                          (SEQ ID NO: 28)
SHIQIPPGLTELLQGYTVEVGQQPPDLVDFAVEYFTRLREARRQ

PKA RIIβ
                                          (SEQ ID NO: 29)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:19 below. (See Figure 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                          (SEQ ID NO: 19)
SHIQIPPGLTELLQGYTVEVLRQQPPDLVEFAVEYFTRLREARA
```

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:21), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:21 below. The skilled artisan will realize that in designing sequence variants of the AD sequence, one would desirably avoid changing any of the underlined residues, while conservative amino acid substitutions might be made for residues that are less critical for DDD binding.

AKAP-IS
(SEQ ID NO: 21)
QIEYL<u>AKQ</u>IVD<u>NAI</u>QQA

Gold et al. (2006, Mol Cell 24:383-95) utilized crystallography and peptide screening to develop a SuperAKAP-IS sequence (SEQ ID NO:30), exhibiting a five order of magnitude higher selectivity for the MI isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL® constructs. Figure 2 of Gold et al. disclosed additional DDD-binding sequences from a variety of AKAP proteins.

SuperAKAP-IS
(SEQ ID NO: 30)
QIEY<u>V</u>AKQIVD<u>Y</u>AI<u>H</u>QA

Stokka et al. (2006, Biochem J 400:493-99) also developed peptide competitors of AKAP binding to PKA. The peptide antagonists were designated as Ht31, RIAD and PV-38. The Ht-31 peptide exhibited a greater affinity for the RII isoform of PKA, while the RIAD and PV-38 showed higher affinity for RI.

Hundsrucker et al. (2006, *Biochem J* 396:297-306) developed still other peptide competitors for AKAP binding to PKA, with a binding constant as low as 0.4 nM to the DDD of the MI form of PKA. The sequences of various AKAP antagonistic peptides are provided in Table 1 of Hundsrucker et al.

Residues that were highly conserved among the AD domains of different AKAP proteins are indicated below by underlining with reference to the AKAP IS sequence (SEQ ID NO:21). The residues are the same as observed by Alto et al. (2003), with the addition of the C-terminal alanine residue. (See Figure 4 of Hundsrucker et al. (2006), incorporated herein by reference.) The sequences of peptide antagonists with particularly high affinities for the MI DDD sequence were those of AKAP-IS, AKAP7δ-wt-pep, AKAP7δ-L304T-pep and AKAP7δ-L308D-pep.

AKAP-IS
(SEQ ID NO: 21)
QIEYL<u>AKQ</u>IVD<u>NAI</u>QQA

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:19. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 19)
SH*IQ*<u>I</u>PP*GL*T*ELL*QG*YT*V*EVL*RQQ*PP*D*LVE*F*AVE*YF*TR*L*REA*R*A

The skilled artisan will realize that these and other amino acid substitutions in the DDD or AD amino acid sequences may be utilized to produce alternative species within the genus of AD or DDD moieties, using techniques that are standard in the field and only routine experimentation.

Alternative DNL® Structures

In certain alternative embodiments, DNL® constructs may be formed using alternatively constructed antibodies or antibody fragments, in which an AD moiety may be attached at the C-terminal end of the kappa light chain ($C_k$), instead of the C-terminal end of the Fc on the heavy chain. The alternatively formed DNL® constructs may be prepared as disclosed in U.S. Pat. No. 9,446,123, the entire text of which is incorporated herein by reference. The light chain conjugated DNL® constructs exhibit enhanced Fc-effector function activity in vitro and improved pharmacokinetics, stability and anti-lymphoma activity in vivo (Rossi et al., 2013, Bioconjug Chem 24:63-71).

$C_k$-conjugated DNL® constructs may be prepared as disclosed in U.S. Pat. No. 9,446,123. Briefly, $C_k$-AD2-IgG, was generated by recombinant engineering, whereby the AD2 peptide was fused to the C-terminal end of the kappa light chain. Because the natural C-terminus of $C_K$ is a cysteine residue, which forms a disulfide bridge to $C_H L$ a 16-amino acid residue "hinge" linker was used to space the AD2 from the $C_K$-$V_H$1 disulfide bridge. The mammalian expression vectors for $C_k$-AD2-IgG-veltuzumab and $C_k$-AD2-IgG-epratuzumab were constructed using the pdHL2 vector, which was used previously for expression of the homologous $C_H$3-AD2-IgG modules. A 2208-bp nucleotide sequence was synthesized comprising the pdHL2 vector sequence ranging from the Bam HI restriction site within the $V_K/C_K$ intron to the Xho I restriction site 3' of the $C_k$ intron, with the insertion of the coding sequence for the hinge linker (EFPKPSTPPGSSGGAP, SEQ ID NO:31) and AD2, in frame at the 3' end of the coding sequence for $C_K$. This synthetic sequence was inserted into the IgG-pdHL2 expression vectors for veltuzumab and epratuzumab via Bam HI and Xho I restriction sites. Generation of production clones with SpESFX-10 were performed as described for the $C_H$3-AD2-IgG modules. $C_k$-AD2-IgG-veltuzumab and $C_k$-AD2-IgG-epratuzumab were produced by stably-transfected production clones in batch roller bottle culture, and purified from the supernatant fluid in a single step using MabSelect (GE Healthcare) Protein A affinity chromatography.

Following the same DNL® process described previously for 22-(20)-(20) (Rossi et al., 2009, *Blood* 113:6161-71), $C_k$-AD2-IgG-epratuzumab was conjugated with $C_H$1-DDD2-Fab-veltuzumab, a Fab-based module derived from veltuzumab, to generate the bsHexAb 22*-(20)-(20), where the 22* indicates the $C_k$-AD2 module of epratuzumab and each (20) symbolizes a stabilized dimer of veltuzumab Fab. The properties of 22*-(20)-(20) were compared with those of 22-(20)-(20), the homologous Fc-bsHexAb comprising $C_H$3-AD2-IgG-epratuzumab, which has similar composition and molecular size, but a different architecture.

Following the same DNL® process described previously for 20-2b (Rossi et al., 2009, *Blood* 114:3864-71), $C_k$-AD2-IgG-veltuzumab, was conjugated with IFNα2b-DDD2, a module of IFNα2b with a DDD2 peptide fused at its C-terminal end, to generate 20*-2b, which comprises veltuzumab with a dimeric IFNα2b fused to each light chain. The properties of 20*-2b were compared with those of 20-2b, which is the homologous Fc-IgG-IFNα.

Each of the bsHexAbs and IgG-IFNα were isolated from the DNL® reaction mixture by MabSelect affinity chromatography. The two $C_k$-derived prototypes, an anti-CD22/CD20 bispecific hexavalent antibody, comprising epratuzumab (anti-CD22) and four Fabs of veltuzumab (anti-CD20), and a CD20-targeting immunocytokine, comprising veltuzumab and four molecules of interferon-α2b, displayed enhanced Fc-effector functions in vitro, as well as improved pharmacokinetics, stability and anti-lymphoma activity in vivo, compared to their Fc-derived counterparts.

Amino Acid Substitutions

In alternative embodiments, the disclosed methods and compositions may involve production and use of proteins or peptides with one or more substituted amino acid residues. For example, the DDD and/or AD sequences used to make DNL® constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, *J. Mol. Biol.,* 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry,* 13:222-245; 1978, *Ann. Rev. Biochem.,* 47: 251-276; 1979, *Biophys.* 1, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:32) and veltuzumab (SEQ ID NO:33).

```
Rituximab heavy chain variable region sequence
                                       (SEQ ID NO: 32)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
                                       (SEQ ID NO: 33)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotypoe characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Exemplary antibody constant region sequences of use in the chimeric and humanized anti-histone antibodies are disclosed in SEQ ID NO:34 and SEQ ID NO:35 below.

```
Exemplary human heavy chain constant region
                                       (SEQ ID NO: 34)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

Exemplary human light chain constant region
                                       (SEQ ID NO: 35)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC
```

Immunoconjugates

In certain embodiments, the antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as 125I, $^{131}$I, $^{123}$I, $^{124}$I, $^{62}$Cu, $^{64}$Cu, $^{18}$F, $^{111}$In$^{67}$Ga, $^{68}$Ga, $^{99m}$Tc, $^{94m}$Tc, $^{11}$C, $^{13}$N, $^{15}$O, $^{76}$Br for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

PAD Inhibitors

In certain preferred embodiments, a therapeutic agent for use either alone or in combination with or conjugated to an anti-histone agent, such as an anti-histone antibody, may be a PAD inhibitor. PADs (protein arginine deiminases) catalyze the post-translational citrullination of histones and other proteins, in which arginine amino acid residues are converted to citrulline. Overexpression of PADs has been observed in various disease states, such as rheumatoid arthritis, Alzheimer's disease, multiple sclerosis, systemic lupus, Parkinson's disease and cancer (Bicker & Thompson, 2013, 99:155-63). In humans, PADs comprise five calcium-dependent isozymes (PADs 1-4 and 6), which share about 50% sequence homology (Bicker & Thompson, 2013, 99:155-63). While the various isozymes are found in different tissues throughout the body, only PAD4 has been confirmed to play a role in histone citrullination (Bicker & Thompson, 2013, 99:155-63).

PADs have also been identified as playing crucial roles in the generation of neutrophil extracellular traps (NETs) (Bicker & Thompson, 2013, 99:155-63). PAD4 plays a regulatory role in NET formation by mediating chromatin decondensation through histone citrullination (Bicker & Thompson, 2013, 99:155-63). In particular, citrullinated histone H3 appears to be important in NET formation (Bicker & Thompson, 2013, 99:155-63). The pan-PAD inhibitor Cl-amidine has been commonly used in studies of disease therapy, such as rheumatoid arthritis treatment, and may be of use in the instant claimed methods. However, other known PAD inhibitors, such as BB-Cl-amidine, YW3-56, (see, e.g., Wang et al., 2012, J Biol Chem 287:25941-53; Knight et al., 2015, Ann Rheum Dis 74:2199-206), o-F-amidine, o-Cl-amidine, TDFA (Thr-Asp-F-amidine) or streptonigrin (Bicker & Thompson, 2013, Biopolymers 99:155-63) may also be used in the methods and compositions.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject anti-histone antibodies or other histone-neutralizing agents, or else separately administered before, simultaneously with, or after the histone-neutralizing agent. Drugs of use may possess a pharmaceutical property selected from the group consisting of antimitotic, antikinase (e.g., anti-tyrosine kinase), alkylating, antimetabolite, antibiotic, alkaloid, anti-angiogenic, pro-apoptotic agents, immune modulators, and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide, transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-$\alpha$, -$\beta$ or -$\gamma$, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); interleukins (ILs) such as IL-1, IL-1$\alpha$, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. Lenolidamide is yet another immunomodulator that has shown activity in controlling certain cancers, such as multiple myeloma and hematopoietic tumors.

Other useful therapeutic agents may comprise oligonucleotides, especially antisense oligonucleotides that preferably are directed against oncogenes and oncogene products, such as bcl-2. A preferred form of therapeutic oligonucleotide is siRNA.

Immune Dysregulatory Disease

In various embodiments, the histone-neutralizing agents are of use to treat immune-dysregulatory diseases, such as acute kidney injury. In certain preferred embodiments, the therapy may utilize either a combination of two or more histone-neutralizing agents.

Additional therapeutic agents that may be added in combination include a cytokine, a chemokine, a coagulation inhibitor, an anti-T cell or anti B-cell antibody or antibody fragment, an immunomodulator, a stem cell growth factor, a lymphotoxin, a hematopoietic factor, a colony stimulating factor, an interferon, erythropoietin or thrombopoietin. An optional therapeutic agent may include activated protein C, heparin or thrombomodulin, as mentioned above. Combinations of anti-histone antibodies or fragments thereof with other histone neutralizing agents, including but not limited to antibodies or antibody fragments against additional immune system target antigens, as discussed below, may be utilized in certain embodiments.

The immune system comprises both the innate immune system and the adaptive or acquired immune system. Many host cells participate in the processes of innate and adaptive immunity, such as neutrophils, T- and B-lymphocytes, macrophages and monocytes, dendritic cells, and plasma cells. They usually act in concert, affecting one another, particularly in the regulation of certain factors and cytokines that contribute to the recognition and processing of innate and external noxients, and these systems have evolved over the millions of years of the development of vertebrate, mammalian, and human organisms.

A major goal of immunotherapy is to exploit or enhance a patient's immune system against an innate or foreign noxient, such as a malignant cell or an invading microorganism. The immune system has been studied more in relation to recognizing and responding to exogenous noxients, such as microbial organisms, than it has in relation to indigenous malfunctions, such as cancer and certain autoimmune and immune-dysregulatory diseases, particularly since the latter may have both genetic as well as environmental components. The defenses against microbial organisms, such as bacteria, fungi, parasites, and viruses, are innate to the particular organism, with the immune system being programmed to recognize biochemical patterns of these microorganisms and to respond to attack them without requiring prior exposure to the microorganism. This innate immune system includes, for example, neutrophils, natural killer cells and monocytes/macrophages that can eradicate the invading microorganisms by direct engulfment and destruction.

The innate immune response is often referred to as a nonspecific one that controls an invading external noxient until the more specific adaptive immune system can marshal specific antibodies and T cells (cf. Modlin et al., *N Engl J Med* 1999, 340:1834-1835; Das, *Crit. Care* 2000; 4:290-296). The nonspecific immune responses involve the lymphatic system and phagocytes. The lymphatic system includes the lymphocytes and macrophages. Macrophages can engulf, kill and dispose of foreign particles. Phagocytes include neutrophils and macrophages, which again ingest, degrade and dispose of debris, and have receptors for complement and antibody. In summary, the innate immune system provides a line of defense again certain antigens because of inherited characteristics.

In contrast, the adaptive, or acquired, immune system is highly evolved and very specific in its responses. It is called an adaptive system because it occurs during the lifetime of an individual as an adaptation to infection with a pathogen. Adaptive immunity can be artificially acquired in response to a vaccine (antigens) or by administering antibodies, or can be naturally acquired by infection. The acquired immunity can be active, if an antibody was produced, or it can be passive, if exogenous antibody made from another source is injected.

The adaptive immune system produces antibodies specific to a given antigen. The simplest and most direct way in which antibodies provide protection is by binding to them and thereby blocking their access to cells that they may infect or destroy. This is known as neutralization. Binding by antibodies, however, is not sufficient to arrest the replication of bacteria that multiply outside cells. In this case, one role of antibody is to enable a phagocytic cell to ingest and destroy the bacterium. This is known as opsonization. The third function of antibodies is to activate a system of plasma proteins, known as complement. In many cases, the adaptive immune system confers lifelong protective immunity to re-infection with the same pathogen, because the adaptive immune system has a 'memory' of the antigens presented to it.

Antibody-mediated immunity is called humoral immunity and is regulated by B cells and the antibodies they produce. Cell-mediated immunity is controlled by T cells. Both humoral and cell-mediated immunity participate in protecting the host from invading organisms. This interplay can result in an effective killing or control of foreign organisms. Occasionally, however, the interplay can become erratic. In these cases, there is a dysregulation that can cause disease. Sometimes the disease is life-threatening, such as with septic shock and certain autoimmune disorders.

The B and T lymphocytes are critical components of a specific immune response. B cells are activated by antigen to engender clones of antigen-specific cells that mediate adaptive immunity. Most clones differentiate to plasma cells that secrete antibody, while a few clones form memory cells that revert to plasma cells. Upon subsequent re-infection, memory cells produce a higher level of antibody in a shorter period than in the primary response. Antibodies secreted by the plasma cells can play multiple roles in immunity, such as binding and neutralizing a foreign agent, acting as opsonins (IgG) to promote phagocytosis, directly affecting metabolism and growth of some organisms, engaging in antigen-antibody reactions that activate complement, causing phagocytosis and membrane attack complex, and/or engaging in antigen-antibody reactions that activate T cells and other killer cells.

T lymphocytes function as both helper cells and suppressor cells. Helper T cells induce antigen-specific B cells and effector T cells to proliferate and differentiate. Suppressor T cells interact with helper T cells to prevent an immune response or to suppress an ongoing one, or to regulate effector T cells. Cytotoxic T cells destroy antigen by binding to target cells. In a delayed-type hypersensitivity reaction, the T cells do not destroy antigen, but attract macrophages, neutrophils and other cells to destroy and dispose of the antigen.

T cells can detect the presence of intracellular pathogens because infected cells display on their surface peptide fragments derived from the pathogens' proteins. These foreign peptides are delivered to the cell surface by specialized host-cell glycoproteins, termed Major Histocompatibility Complex (MHC) molecules. The recognition of antigen as a small peptide fragment bound to a MHC molecule and displayed at the cell surface is one of the most distinctive features of T cells. There are two different classes of MHC molecules, known as MHC class I and MHC class II, that deliver peptides from different cellular compartments to the surface of the infected cell. Peptides from the cytosol are bound to MHC class I molecules which are expressed on the majority of nucleated cells and are recognized by CD8+ T cells. MHC class II molecules, in contrast, traffic to lysosomes for sampling endocytosed protein antigens which are presented to the CD4+ T cells (Bryant and Ploegh, *Curr Opin Immunol* 2004; 16:96-102).

CD8+ T cells differentiate into cytotoxic T cells, and kill the target cell. CD4+ T cells differentiate into two types of effector T cells. Pathogens that accumulate in large numbers inside macrophage vesicles tend to stimulate the differentiation of $T_{H1}$ cells which activate macrophages and induce B cells to make IgG antibodies that are effective in opsonizing extracellular pathogens for uptake by phagocytes. Extracellular antigens tend to stimulate the production of $T_{H2}$ cells which initiate the humoral immune response by activating naive antigen-specific B cells to produce IgM antibodies, inter alia.

The innate and adaptive immune systems interact, in that the cells of the innate immune system can express various molecules that can interact with or trigger the adaptive immune system by activating certain cells capable of producing immune factors, such as by activating T and B cells of the lymphatic series of leukocytes. The early induced but non-adaptive responses are important for two main reasons. First, they can repel a pathogen or, more often, control it until an adaptive immune response can be mounted. Second, these early responses influence the adaptive response in several ways. For example, the innate immune response produces cytokines and other inflammatory mediators that have profound effects on subsequent events, including the recruitment of new phagocytic cells to local sites of infection. Another effect of these mediators is to induce the expression of adhesion molecules on the endothelial cells of the local blood vessels, which bind to the surface of circulating monocytes and neutrophils and greatly increase their rate of migration of these cells out of the blood and into the tissues. These events all are included under the term inflammation, which is a feature of the innate immune system that forms part of the protective response at a localized site to isolate, destroy and remove a foreign material. This is followed by repair. Inflammation is divided into acute and chronic forms.

The immune system communicates via nonspecific tissue resistance factors. These include the interferons, which are proteins produced in response to viruses, endotoxins and certain bacteria. Interferons inhibit viral replication and activate certain host-defense responses. Infected cells produce interferon that binds the infected cells to other, neighboring cells, causing them to produce antiviral proteins and enzymes that interfere with viral gene transcription and proteins synthesis. Interferons can also affect normal cell growth and suppress cell-mediated immunity.

Complement is another nonspecific tissue resistance factor, and comprises plasma proteins and membrane proteins that mediate specific and non-specific defenses. Complement has two pathways, the classical pathway associated with specific defense, and the alternative pathway that is activated in the absence of specific antibody, and is thus non-specific. In the classical pathway, antigen-antibody complexes are recognized when C1 interacts with the Fc of the antibody, such as IgM and to some extent, IgG, ultimately causing mast cells to release chemotactic factors, vascular mediators and a respiratory burst in phagocytes, as one of many mechanisms. The key complement factors include C3a and C5a, which cause mast cells to release chemotactic factors such as histamine and serotonin that attract phagocytes, antibodies and complement, etc. Other key complement factors are C3b and C5b, which enhance phagocytosis of foreign cells, and C8 and C9, which induce lysis of foreign cells (membrane attack complex).

Gelderman et al. (*Mol. Immunol* 2003; 40:13-23) reported that membrane-bound complement regulatory proteins (mCRP) inhibit complement activation by an immunotherapeutic mAb in a syngeneic rat colorectal cancer model. While the use of mAb against tumor antigens and mCRP overcame an observed effect of mCRP on tumor cells, there has been no direct evidence to support this approach. Still other attempts to use bispecific antibodies against CD55 and against a tumor antigen (G250 or EpCAM) have been suggested by Gelderman et al. (Lab Invest 2002; 82:483-493; *Eur J Immunol* 2002; 32:128-135) based on in vitro studies that showed a 2-13-fold increase in C3 deposition compared to use of the parental antitumor antibody. However, no results involving enhanced cell killing were reported. Jurianz et al. (*Immunopharmacology* 1999; 42:209-218) also suggested that combining treatment of a tumor with anti-HER2 antibodies in vitro could be enhanced by prior treatment with antibody-neutralization of membrane-complement-regulatory protein, but again no in vivo results were provided. Sier et al. (*Int J Cancer* 2004; 109:900-908) recently reported that a bispecific antibody made against an antigen expressed on renal cell carcinoma (Mab G250) and CD55 enhanced killing of renal cancer cells in spheroids when beta-glucan was added, suggesting that the presence of CR3-priming beta-glucan was obligatory.

Neutrophils, another cell involved in innate immune response, also ingest, degrade and dispose of debris. Neutrophils have receptors for complement and antibody. By means of complement-receptor bridges and antibody, the foreign noxients can be captured and presented to phagocytes for engulfment and killing.

Macrophages are white blood cells that are part of the innate system that continually search for foreign antigenic substances. As part of the innate immune response, macrophages engulf, kill and dispose of foreign particles. However, they also process antigens for presentation to B and T cells, invoking humoral or cell-mediated immune responses.

The dendritic cell is one of the major means by which innate and adaptive immune systems communicate (Reis e Sousa, *Curr Opin Immunol* 2004; 16:21-25). It is believed that these cells shape the adaptive immune response by the reactions to microbial molecules or signals. Dendritic cells capture, process and present antigens, thus activating CD4+ and CD8+ naive T lymphocytes, leading to the induction of primary immune responses, and derive their stimulatory potency from expression of MHC class I, MHC class II, and accessory molecules, such as CD40, CD54, CD80, CD86, and T-cell activating cytokines (Steinman, *J Exp Hematol* 1996; 24:859-862; Banchereau and Steinman, *Nature* 1998; 392:245-252). These properties have made dendritic cells candidates for immunotherapy of cancers and infectious diseases (Nestle, *Oncogene* 2000; 19:673-679; Fong and Engleman, *Annu Rev Immunol* 2000; 18:245-273; Lindquist and Pisa, *Med Oncol* 2002; 19:197-211), and have been shown to induce antigen-specific cytotoxic T cells that result in strong immunity to viruses and tumors (Kono et al., Clin Cancer Res 2002; 8:394-40).

Also important for interaction of the innate and adaptive immune systems is the NK cell, which appears as a lymphocyte but behaves like a part of the innate immune system. NK cells have been implicated in the killing of tumor cells as well as essential in the response to viral infections (Lanier, *Curr Opin Immunol* 2003; 15:308-314; Carayannopoulos and Yokoyama, *Curr Opin Immunol* 2004; 16:26-33). Yet another important mechanism of the innate immune system is the activation of cytokine mediators that alert other cells of the mammalian host to the presence of infection, of which a key component is the transcription factor NF-κB (Li and Verna, *Nat Rev Immunol* 2002; 2:725-734).

As mentioned earlier, the immune system can overreact, resulting in allergies or autoimmune diseases. It can also be suppressed, absent, or destroyed, resulting in disease and death. When the immune system cannot distinguish between "self" and "nonself," it can attach and destroy cells and tissues of the body, producing autoimmune diseases, e.g., juvenile diabetes, multiple sclerosis, myasthenia gravis, systemic lupus erythematosus, rheumatoid arthritis, and immune thrombocytopenic purpura. Immunodeficiency disease results from the lack or failure of one or more parts of the immune system, and makes the individuals susceptible to diseases that usually do not affect individuals with a normal immune system. Examples of immunodeficiency disease are severe combined immunodeficiency disease (SCID) and acquired immunodeficiency disease (AIDS). The latter results from human immunodeficiency virus (HIV) and the former from enzyme or other inherited defects, such as adenosine deaminase deficiency.

Numerous and diverse methods of immunosuppression or of neutralizing proinflammatory cytokines have proven to be unsuccessful clinically in patients with sepsis and septic shock anti-inflammatory strategies. (Riedmann, et al., cited above; Van Amersfoort et al. (*Clin Microbiol Rev* 2003; 16:379-414), such as general immunosuppression, use of nonsteroidal anti-inflammatory drugs, TNF-α antibody (infliximab) or a TNF-R:Fc fusion protein (etanercept), IL-1 (interleukin-1) receptor antagonist, or high doses of corticosteroids. However, a success in the treatment of sepsis in adults was the PROWESS study (Human Activated Protein C Worldwide Evaluation in Severe Sepsis (Bernard et al., *N Engl J Med* 2001; 344:699-709)), showing a lower mortality (24.7%) than in the placebo group (30.8%). This activated protein C (APC) agent probably inhibits both thrombosis and inflammation, whereas fibrinolysis is fostered. Friggeri et al. (2012, *Mol Med* 18:825-33) reported that APC degrades histones H3 and H4, which block uptake and clearance of apoptotic cells by macrophages and thereby contribute to organ system dysfunction and mortality in acute inflammatory states. Van Amersfoort et al. state, in their review (ibid.) that: "Although the blocking or modulation of a number of other targets including complement and coagulation factors, neutrophil adherence, and NO release, are promising in animals, it remains to be determined whether these therapeutic approaches will be effective in humans." This is further emphasized in a review by Abraham, "Why immunomodulatory therapies have not worked in sepsis" (*Intensive Care Med* 1999; 25:556-566). In general, although many rodent models of inflammation and sepsis have shown encouraging results with diverse agents over the past decade or more, most agents translated to the clinic failed to reproduce in humans what was observed in these animal models, so that there remains a need to provide new agents that can control the complex presentations and multiple-organ involvement of various diseases involving sepsis, coagulopathy, and certain neurodegenerative conditions having inflammatory or immune dysregulatory components.

More recent work on immunoglobulins in sepsis or septic shock has been reported. For example, Toussaint and Gerlach (2012, *Curr Infect Dis Rep* 14:522-29) summarized the use of ivIG as an adjunct therapy in sepsis. The metanalysis failed to show any strong correlation between general immunoglobulin therapy and outcome. LaRosa and Opal (2012, *Curr Infect Dis Rep* 14:474-83) reported on new therapeutic agents of potential use in sepsis. Among other agents, anti-TNF antibodies are in current clinical trials for sepsis, while complement antagonists have shown promising results in preclinical models of sepsis. Nalesso et al. (2012, *Curr Infect Dis Rep* 14:462-73) suggested that combination therapies with multiple agents may prove more effective for sepsis treatment. The immunopathogenesis of sepsis has been summarized by Cohen (2002, *Nature* 420:885-91).

The immune system in sepsis is believed to have an early intense proinflammatory response after infection or trauma, leading to organ damage, but it is also believed that the innate immune system often fails to effectively kill invading microorganisms (Riedmann and Ward, *Expert Opin Biol Ther* 2003; 3:339-350). There have been some studies of macrophage migration inhibitory factor (MIF) in connection with sepsis that have shown some promise. For example, blockage of MIF or targeted disruption of the MIF gene significantly improved survival in a model of septic shock in mice (Calandra et al., *Nature Med* 2000; 6:164-170), and several lines of evidence have pointed to MIF as a potential target for therapeutic intervention in septic patients (Riedmann et al., cited above). Bucala et al. (U.S. Pat. No. 6,645,493 B1) have claimed that an anti-MIF antibody can be effective therapeutically for treating a condition or disease caused by cytokine-mediated toxicity, including different forms of sepsis, inflammatory diseases, acute respiratory disease syndrome, granulomatous diseases, chronic infections, transplant rejection, cachexia, asthma, viral infections, parasitic infections, malaria, and bacterial infections, which is incorporated herein in its entirety, including references. The use of anti-LPS (lipopolysaccharide) antibodies alone similarly has had mixed results in the treatment of patients with septic shock (Astiz and Rackow, *Lancet* 1998; 351: 1501-1505; Van Amersfoort et al., *Clin Microbiol Rev* 2003; 16:379-414.

Complement C5a, like C3a, is an anaphylatoxin. It mediates inflammation and is a chemotactic attractant for induction of neutrophilic release of antimicrobial proteases and oxygen radicals. Therefore, C5a and its predecessor C5 are particularly preferred targets. By targeting C5, not only is C5a affected, but also C5b, which initiates assembly of the membrane-attack complex. Thus, C5 is another preferred target. C3b, and its predecessor C3, also are preferred targets, as both the classical and alternate complement pathways depend upon C3b. Three proteins affect the levels of this factor, C1 inhibitor, protein H and Factor I, and these are also preferred targets according to the invention. Complement regulatory proteins, such as CD46, CD55, and CD59, may be targets to which the multispecific antibodies bind.

Coagulation factors also are preferred targets according to the invention, particularly tissue factor (TF), thrombomodulin, and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, multispecific antibodies that target TF are useful not only in the treatment of coagulopathies, but also in the treatment of sepsis, cancer, pathologic angiogenesis, and other immune and inflammatory dysregulatory diseases according to the invention. A complex interaction between the coagulation pathway and the cytokine network is suggested by the ability of several cytokines to influence TF expression in a variety of cells and by the effects of ligand binding to the receptor. Ligand binding (factor VIIa) has been reported to give an intracellular calcium signal, thus indicating that TF is a true receptor.

Thrombin is the activated form of coagulation factor II (prothrombin); it converts fibrinogen to fibrin. Thrombin is a potent chemotaxin for macrophages, and can alter their production of cytokines and arachidonic acid metabolites. It is of particular importance in the coagulopathies that accompany sepsis. Numerous studies have documented the activation of the coagulation system either in septic patients or following LPS administration in animal models. Despite more than thirty years of research, the mechanisms of LPS-induced liver toxicity remain poorly understood. It is now clear that they involve a complex and sequential series of interactions between cellular and humoral mediators. In the same period of time, gram-negative systemic sepsis and its sequellae have become a major health concern, attempts to use monoclonal antibodies directed against LPS or various inflammatory mediators have yielded only therapeutic failures, as noted elsewhere herein. Multispecific antibodies according to the invention that target both thrombin and at least one other target address the clinical failures in sepsis treatment.

A recombinant form of thrombomodulin has been approved for treatment of disseminated intravascular coagulation (DIC) and is in phase II clinical trials for DIC associated with sepsis (Okamoto et al., 2012, *Crit Care Res Pract*, Epub 2012 Feb. 28). Thrombomodulin has a pivotal role in the protein C system that is important in the pathogensis of sepsis (Levi and Van der Poll, *Minerva Anestesiol* Epub Dec. 17, 2012). Downregulation of thrombomodulin in sepsis causes impaired activation of protein C that is central in the modulation of coagulation and inflammation (Levi and Van der Poll, *Minerva Anestesiol* Epub Dec. 17, 2012). Administration of recombinant thrombomodulin is reported to have a beneficial effect on restoration of coagulation and improvement of organ failure (Levi and Van der Poll, *Minerva Anestesiol* Epub Dec. 17, 2012). A recent retrospective study confirmed that treatment with recombinant thrombomodulin was associated with reduced mortality in hospitalized patients with sepsis-induced DIC (Yamakawa et al., 2013, *Intensive Care Med*, Epub Jan. 30, 2013).

In other embodiments, the multispecific antibodies bind to a MHC class I, MHC class II or accessory molecule, such as CD40, CD54, CD80 or CD86. The multispecific antibody also may bind to a T-cell activation cytokine, or to a cytokine mediator, such as NF-κB.

Kits

Various embodiments may concern kits containing components suitable for treating or diagnosing acute kidney injury in a patient. Exemplary kits may contain one or more histone-neutralizing agents, such as the anti-histone antibodies described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1. Role of Histones in Inducing Remote Organ Injury and Further Inducing Tubular Necrosis in Acute Kidney Injury Introduction Acute kidney injury (AKI) causes renal dysfunction and has potential life-threatening complications, such as the accumulation of uremic toxins, imbalance of fluid volume, mineral disorders, and metabolic acidosis (2015, Clin J Am Soc Nephrol 10:21-8). Acute tubular necrosis triggered by ischemia-reperfusion (IR) or nephrotoxins is a major cause of severe AKI (Basile et al., 2012, Compr Physiol 2:1303-53). The mortality rate of AKI patients has not improved despite advances in technologies such as renal replacement therapy.

The molecular mechanisms of AKI have been well studied in terms of epithelial and endothelial cell physiology and cell-to-cell interactions using ischemic AKI model animals (Sharfuddin & Molitoris, 2011, Nat Rev Nephrol 7:189-200). Recently, we introduced the concept of necroinflammation, where renal cell necrosis via the release of damage-associated molecular patterns (DAMPs) from necrotic cells drives intrarenal inflammation and the injury of other cells in an auto-amplification loop (Mulay et al., 2015, J Am Soc Nephrol 27:27-39). Regulated forms of necrosis include necroptosis, ferroptosis, and mitochondrial permeability transition-mediated regulated necrosis (MPT-RN) (Linkermann et al., 2014, Nat Rev Immunol 14:759-67). All of these release DAMPs that alert the innate immune system (Braza et al., 2016, Nat Rev Nephrol 12:281-90). While this process can help to control infections, it accelerates unnecessary tissue damage such as IR injury (IRI).

Among DAMPs, histones have a particular role as they elicit direct cytotoxic effects, hence histones are cytotoxic DAMPs (Kumar et al., 2015, J Am Soc Nephrol 26:2399-413). Especially, neutrophils infiltrate the kidney during the early injury phase (Matthijsen et al., 2007, Am J Pathol 171:1743-52; Lech et al., 2013, Kidney Int 83:647-61) and contribute to organ damage (Hayama et al., 2006, Transplant Proc 38:2201-2), but the mechanisms are not clear. Zychlinsky, et al. discovered the phenomenon of neutrophil extracellular trap (NET) formation as a previously unknown mode of bacterial killing. (Brinkmann et al., 2004, Science 303:1532-1535). NET formation is usually associated with neutrophil death, a process named NETosis, and that is morphologically distinguished from apoptosis and necrosis (Fuchs et al., 2007, J Cell Biol 176:231-41).

NET formation depends on the activation of peptidyl arginine deiminase (PAD) enzymes, which convert arginine residues of histones to citrulline (Li et al., 2010, J Exp Med 207:1853-62). Histone citrullination neutralizes DNA-histone interactions, resulting in chromatin decondensation and NET release (Remijsen et al., 2011, Cell Death Differ 18:581-8). We speculated on a role of NETs in AKI. In addition, mortality of AKI relates also to multiple organ failure (Scheel et al., 2008, Kidney Int 74:849-51), but the mechanistic link between kidney injury and multiple organ failure could not yet be defined (Klein et al., 2008, Kidney Int 74:901-9; Yap & Lee, 2012, Anesthesiology 116:1139-48). We hypothesized that neutrophils infiltrating the kidney during AKI release cytotoxic histones while undergoing NET formation and that such these histones contribute accelerated AKI as well as to AKI-related remote organ damage. We further hypothesized that anti-histone agents, such as anti-histone antibodies, could ameliorate the toxic effects of AKI, and that PAD inhibitors might further enhance the beneficial effects of histone inhibition.

Materials and Methods

Animal studies.

C57BL/6N male mice were procured from Charles River Laboratories (Sulzfeld, Germany). 6-8 week-old mice (N=5-14) were anesthetized before renal pedicle clamping (unilateral: 15, 25, 35, or 45 min) with a microaneurysm clamp via flank incisions (Medicon, Tuttlingen, Germany). Body temperature was maintained at between 37° C. and 38° C. throughout the procedure by placing the mice on a heating pad. After clamp removal, recovery of blood flow to the kidney was confirmed as evidenced by returning to its original color, before closing the wound. To maintain fluid balance, all mice were supplemented with 0.5 ml of 0.9% NaCl administered peritoneally. Mice were killed after 0 min, 15 min, 30 min, 6 h, 12 h, 15 h, 24 h, 2 d, 3 d, 7 d and 10 days after surgery. Bilateral IRI mice (ischemia 35 min, reperfusion 24 h) were treated with PAD inhibitor (20 mg/kg, intraperitoneal injection; i.p: CALBIOCHEM®), anti-histone IgGs (20 mg/kg, i.p; clone BWA3; IMMUNO-MEDICS®, Morris Plains, N.J.), necrosis inhibitor combination (Necrostatinl/Enzo 1.65 mg/kg i.p, Ferrostatin/CALBIOCHEM®, 2 mg/kg i.p, Ciclosporin/Novartis 10 mg/kg, i.v) 2 hours before IRI surgery. Neutrophil depletion was performed as described previously (Huang et al., 2015, Hepatology 62:600-14) with an i.p. injection of 500 µg anti-Ly6G IgGs (1A8) (BIOXCELL®) or control IgGs 24 and 2 hours before IRI surgery.

Assessment of Tissue Injury and Inflammation.

Tissues were embedded in paraffin, and 3-mm sections were used for HE (hematoxylin and eosin staining), Periodic acid-Schiff (PAS), and IHC (immunohistochemistry) staining. The sections for IHC were deparaffinized, and rehydrated in a graded ethanol series. Endogenous peroxidase was inhibited using 0.3% $H_2O_2$ in PBS for 30 min. Sections were then heated in 97° C. sodium citrate buffer (10 mM, pH 6) for 40 min for antigen retrieval. Sections were treated with the Vector Blocking kit (Vector Laboratories, Burlingame, Calif.) for endogenous biotin inhibition.

For immunofluorescence, the tissues after sacrifice were fixed with 4% paraformaldehyde for 2 hours, dehydrated with 30% sucrose for 24 hours at 4° C., frozen in OCT (TISSUE-TEK®, OCT compounds, SAKURA®) and cryo-sectioned (5 µm thick). The CitH3 positive NETs and TUNEL positive necrotic cells were quantified using ImageJ software. Tubular injury in PAS staining was scored by assessing the percentage of tubules in the cortex and outer-medullary lesion that displayed tubular cell necrosis, tubular dilation, luminal cast formation and inflammatory cells infiltration.

For immunostaining, rat anti-mouse Ly6b (neutrophils) ab (AbD Serotec, Oxford, United Kingdom), rabbit citrullinated histone 3 ab (Abcam, Cambridge, United Kingdom), or goat anti neutrophil elastase ab (Santa Cruz Biotechnology, USA) were used. To count the positive cells, 3 high-power fields (100×) were analyzed. BUN and creatinine were measured using urea or creatinine FS kits (DiaSys Diagnostic Systems, Holzheim, Germany) according to the manufacturer's protocols. Mice plasma was analysed for IL-6 and TNF cytokine secretion by ELISA (BD Pharmingen, San Diego, Calif.). Plasma histone was analyzed by western blotting. To prepare a control model with high concentration of histone, lipopolysaccharide (LPS, 20 mg/kg, i.p) was injected into WT mice (8 weeks age, male), and blood samples were taken 6 hours after LPS injection (Li et al., 2011, Surgery 150:442-51). Bronchoalveolar lavage fluid (BAL) in IRI mice was performed as previously described (Sayah et al., 2015, Am J Respir Crit Care Med 191:455-63). The BAL cell number and supernatant NETs were evaluated by cell counter and NE-DNA complexes ELISA, respectively.

Immunohistofluorescence Staining in Human Tissues.

Fresh frozen sections of renal biopsies from two patients with acute tubular necrosis caused by ischemic condition after renal transplant were provided from the Institute of Pathology at the Sapporo city general hospital. Informed consent was obtained from the patients. The samples were used for HE stain and NETs-immunostaining as previously described.

RNA Preparation and Real-Time RT-PCR.

Total renal RNA was isolated using a Qiagen RNA extraction kit (Qiagen, Germany) as previously described (Kumar et al., 2015, J Am Soc Nephrol 26:2399-413). From isolated RNA, complementary DNA was prepared using reverse transcriptase (SUPERSCRIPT™ II; INVITROGEN™, USA). The SYBR® Green Dye detection system was used for quantitative real-time PCR on a LIGHTCYCLER® 480 (Roche). All gene expression values were normalized using 18s RNA as a house keeping gene.

Cell Culture and Treatment.

The HK-2 (human) and iTEC (human) proximal tubular cell lines were cultured in DMEM medium supplemented with 10% fetal calf serum (FCS) and 1% penicillin-streptomycin until the cells were 80~90% confluent. Before the experiments these cells media were exchanged to DMEM in the absence of FCS/glucose, and placed in normal oxygen ($O_2$: 20%) or hypoxia chamber ($O_2$: 1%), or hydrogen peroxidase ($H_2O_2$: 1 mM) for 24 hours. HK-2 cells were originally purchased from ATCC, and were generously provided by B. Luckow and P. J. Nelson, respectively. iTEC cells were prepared from human renal progenitor cells and tubulogenic differentiation was induced with REGM™ (Lonza Ltd) as described previously (Sayah et al., 2009, J Am Soc Nephrol 20:322-32).

Neutrophil Isolation and In Vitro NET Formation.

Neutrophils were isolated from human healthy volunteers using standard dextran sedimentation followed by Ficoll-Hypaque density centrifugation procedures (Brinkmann et al., 2004, Science 303:1532-1535). Blood donors provided written informed consent forms approved by the local ethical committee. Neutrophils were suspended in RPMI medium ($2 \times 10^5 \sim 2 \times 10^6$ cell/ml) and seeded into 8-well microns slides or 12~96-well plates (Ibidi, Martinsried, Germany) in a 5% carbon dioxide atmosphere at 37° C. for 30 minute before stimulation. The neutrophils were placed in normal or hypoxia condition (1% oxygen) for 3, 6, or 24 hours, or stimulated by Phorbol 12-myristate 13-acetate (PMA, 25 nM, Sigma-Aldrich), total calf thymus histones (10, 50, or 100 µg/ml), and necrotic conditioned media from TCs (control, hypoxia, $H_2O_2$ stimulation) for 3-4 hours. The same groups of neutrophils were pre-treated with PAD inhibitor (Cl-amidine 200 µM), aHisAbs (100 µg/ml) or control IgGs (100 µg/ml).

NETs Cytotoxicity to TCs and Fresh Neutrophils.

Neutrophils were stimulated by PMA, histones, or necrotic TCs derived conditioned media and 3 hours after incubation the supernatant was replaced with fresh media (RPMI), and the bottom NETs were collected to avoid the contamination of the media with exogenous PMA or necrotic TCs or histones as previously described (Najmeh et al., 2015, J Vis Exp 16:98). After centrifugation (1200 rpm, 5 min), the supernatants were applied to TCs (1:1). At 20 hours after addition of conditioned NETs media, TCs injury was evaluated by LDH assay. To investigate whether the formed NETs affect fresh neutrophils, conditioned NETs media was applied to fresh neutrophils and 4 h after incubation, additional NET formation in fresh neutrophils was evaluated by immunostaining.

NETs Quantification Assay.

In human neutrophil experiments, NETs were quantified by the MPO-DNA sandwich ELISA method using anti-DNA abs (Roche, Mannheim, Germany) and anti-human MPO abs (AbD Serotec) as described (Nakazawa, 2014, J Am Soc Nephrol 25:990-7). In mouse neutrophils experiments, BAL NETs (undiluted) and plasma NETs (×2 diluted in PBS) were evaluated by NE-DNA complex using anti-DNA abs and anti-mouse NE abs (Santa Cruz) as described (Sayah et al., 2015, Am J Respir Crit Care Med 191:455-63). The CitH3 positive NETs were quantified using ImageJ software.

Scanning Electron Microscopy.

Cells were fixed with 2.5% glutaraldehyde, post fixed using repeated incubations with 1% osmium tetroxide/1% tannic acid, dehydrated with a graded ethanol series, critical-point dried and coated with 2 nm platinum. Since the NETs are fragile, each step was done with minimal disturbance of the media to preserve the structures.

Cell Death Assay.

A cell death detection (TUNEL) kit (Roche) was used to quantify dead cells in accordance with the manufacturer's instructions. Systemic dead cell derived DNAs in plasma were quantified by PICOGREEN® dsDNA assay kit (Thermo Fisher Scientific). In vitro, cytotoxicity was evaluated by LDH assay (Roche).

Western Blotting.

Mouse plasma or tissue extracts were analyzed by standard immunoblot technique as described elsewhere (Allam et al., 2011, J Immunol 186:2714-8). Anti-histone H3 antibodies, anti-β-actin, and anti-citrullinated histone3 antibodies were purchased from Cell Signaling Technology (Danvers, Mass.) and Abcam. The expression of protein was quantified using ImageJ software.

Statistical Analyses.

Data were expressed as the mean±SEM. Comparison between groups was performed by the two-tailed t test or One-way ANOVA (nonparametric tests). A P-value less than 0.05 indicated statistical significance. All statistical analyses were calculated using GraphPad Prism software (GraphPad).

Results

NETs Expression in Severe Human Acute Tubular Necrosis.

Figure 1B:
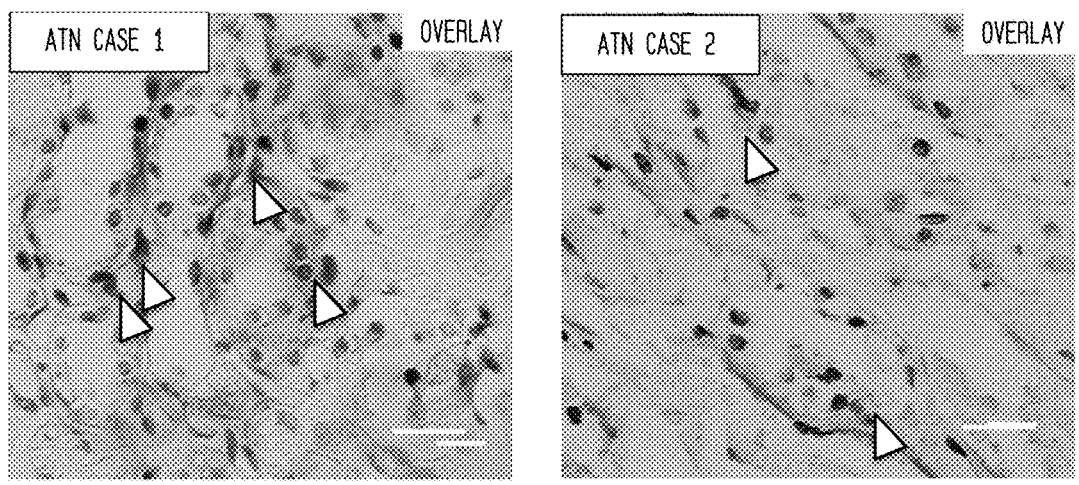
FIG. 1B. NETs evidence in 2 patients with acute tubular necrosis (ATN) after kidney transplantation. Leukocytes are infiltrating surrounding tubular ducts in HE staining (Case 1: left, Case 2: right). Scale Bar: 25 µm.

NETs have been observed at sites of sterile inflammation in humans (Kessenbrock et al., 2009, Nat Med 15:623-5). Hence we first questioned whether NETs develop also in human post-ischemic tubular necrosis. We performed immunofluorescence staining on two kidney biopsies obtained from patients with post-transplant acute tubular necrosis related to long cold ischemia times (Donor of case 1; A 68 year old, male, non-heart-beating donor. Ischemic time=30 minutes. Donor of case 2; A 69 year old, male, Heart-beating donor). Immunostaining in both cases showed the presence of neutrophil elastase/Citrullinated histone 3 (CitH3) positive cells, which implies NET formation, surrounding necrotic tubular cells (FIG. 1A). Haematoxylin and eosin (HE) staining showed that infiltrating leukocytes were present in damaged tubular ducts and the surrounding interstitial space (FIG. 1B).

The Formation of NETs and Tubular Cell Necrosis Enhance Each Other.

Figure 2B:
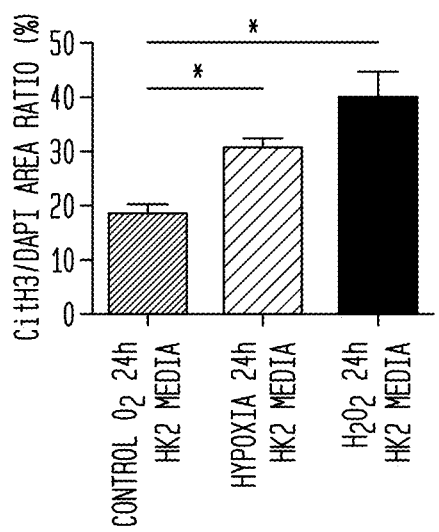
FIG. 2B. NETs initiate the loop of necroinflammation in vitro. The graph shows the ratio of CitH3/DAPI positive area of iTECs.
Figure 2C:
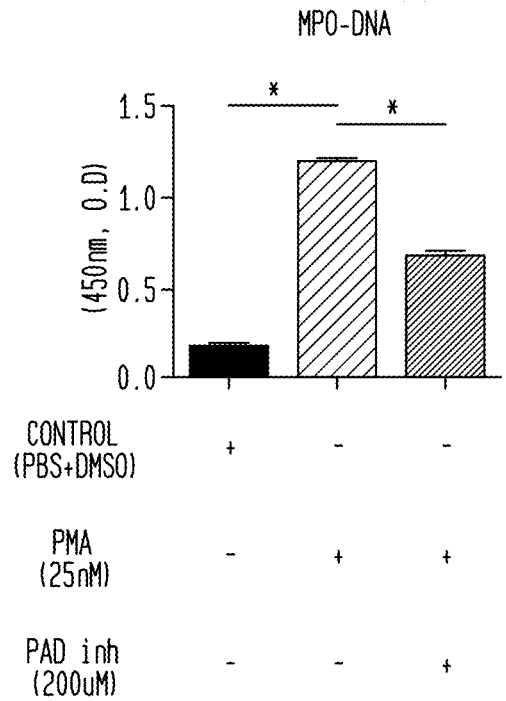
FIG. 2C. NETs initiate the loop of necroinflammation in vitro. Neutrophils were treated with 25 nM PMA in the presence or absence of PAD inhibitor (200 µM) and the degree of NETs was evaluated by MPO-DNA complex of supernatants.
Figure 2D:
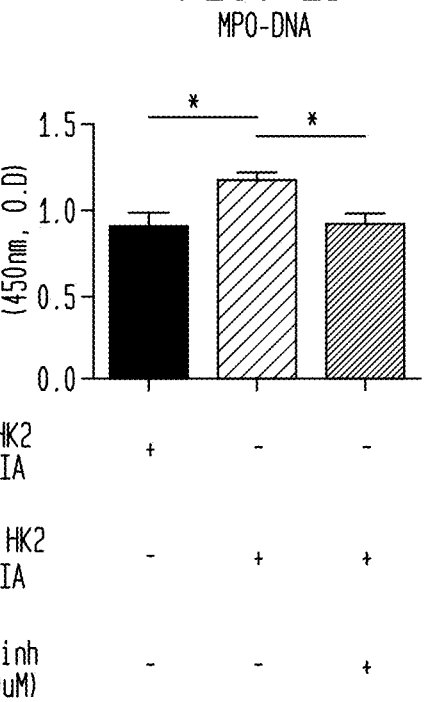
FIG. 2D. NETs initiate the loop of necroinflammation in vitro. Neutrophils were treated with necrotic TCs media in the presence or absence of PAD inhibitor (200 µM) and the degree of NETs was evaluated by MPO-DNA complex of supernatants.
Figure 2E:
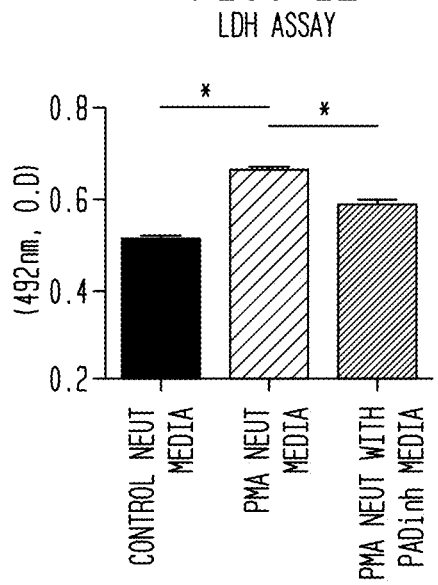
FIG. 2E. NETs initiate the loop of necroinflammation in vitro. The neutrophil supernatants treated with PMA were applied to TCs, and the cytotoxicity of TCs was evaluated by LDH assay 20 hours after addition. The conditioned NETs media was prepared by replacing to fresh media to avoid the contamination of PMA as previously described (McParland et al., 2015, J Vis Exp 98:e52684).
Figure 2F:
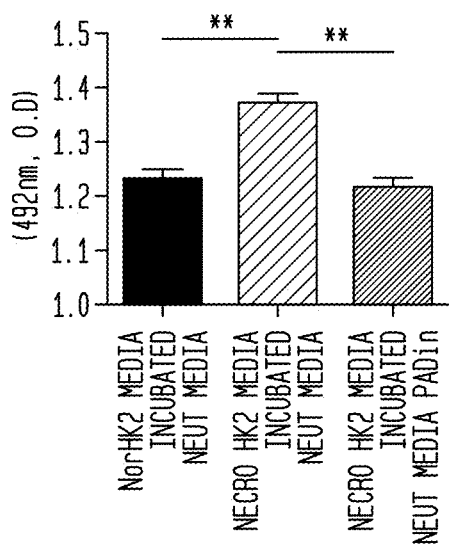
FIG. 2F. NETs initiate the loop of necroinflammation in vitro. The neutrophil supernatants treated with necrotic TCs media were applied to TCs, and the cytotoxicity of TCs was evaluated by LDH assay 20 hours after addition. The conditioned NETs media was prepared by replacing to fresh media to avoid the contamination of TC necrotic media as previously described (McParland et al., 2015, J Vis Exp 98:e52684).

To evaluate whether hypoxia-induced necrosis of tubular cells activates neutrophils, conditioned media from human induced tubular epithelial cells (iTECs) treated with hypoxia ($O_2$; 1%) or hydrogen peroxidase ($H_2O_2$) (10 mM) were applied to human neutrophils. After 4 h of incubation, NET formation was confirmed by fluorescence microscopy (FIGS. 2A and 2B). Similarly, conditioned media from necrotic Human Kidney (HK)-2 cells triggered neutrophils to undergo NETs (FIG. 2C, FIG. 2D) via the activation of citrullinated histones (FIG. 2I) and the neutrophil supernatants were positive for extracellular DNA-myeloperoxidase complexes (FIG. 2F), which implies NET formation. To test whether hypoxia can trigger NET formation directly, neutrophils were incubated under 20% $O_2$ or hypoxic conditions for 24 h but no difference in NET formation was observed (FIG. 2I). These results indicate that only factors released from ischemic tubular cells, but not ischemia itself, triggers NET formation.

Figure 2G:
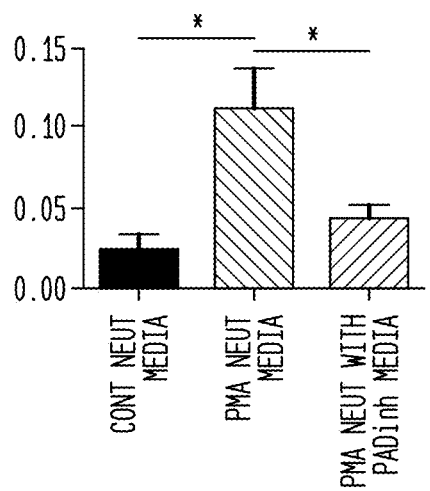
FIG. 2G. NETs initiate the loop of necroinflammation in vitro. PI positive area (%) for control neutrophil media, PMA neutrophil media, PMA neutrophil with PAD in media, $NorO_2$ HK2 media incubated neutrophils, Necro HK2 media incubated neutrophils and Necro HK2 media with PAD incubated neutrophils.
Figure 2G:
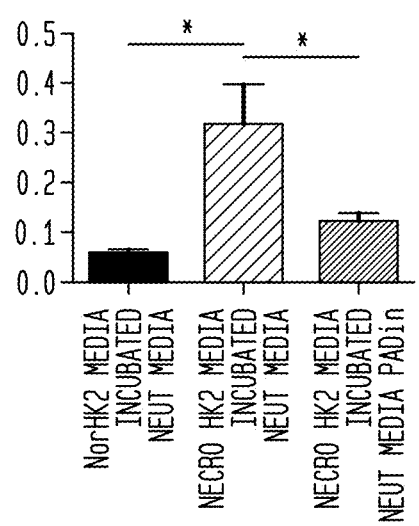
Figure 2H:
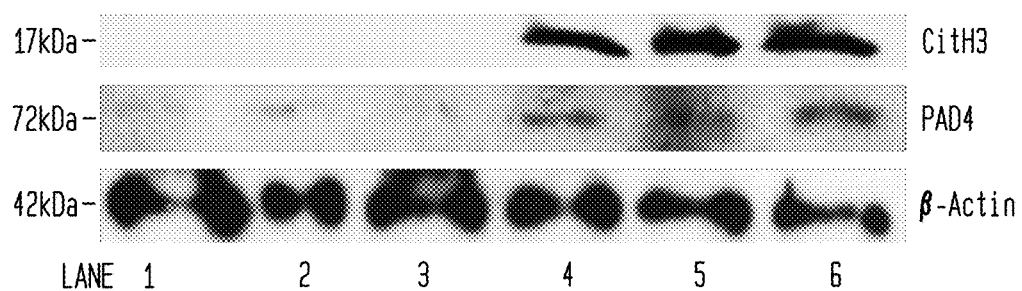
FIG. 2H. NETs initiate the loop of necroinflammation in vitro. The expression of CitH3 and PAD4 of neutrophils treated with normal oxygen or hypoxia condition, or different TCs necrotic media was detected by western blot with β-actin as a loading control. As a positive control of CitH3 expression, neutrophils were treated with 25 nM PMA. Data represent the means±SEM of 3-6 independent experiments, and were analyzed using Student's t-test. *$P<0.05$, **$P<0.01$ versus respective control. DAPI: 4,6-diamidino-2-phenylindole. PMA: Phorbol 12-myristate 13-acetate.

To examine whether NETs affect tubular cells, conditioned media containing NETs was applied to HK-2 cells. After 20 h of incubation, the NET-containing media (FIGS. 2E and 2F) induced HK-2 injury compared to conditioned media obtained from intact neutrophils (FIGS. 2G and 2H). In addition, the NET-containing media activated fresh neutrophils to undergo further NET formation (not shown). PAD inhibitor abrogated induced NET formation in neutrophils and subsequent tubular cell injury (FIG. 2E-2H). Together these data imply that neutrophils undergoing NETosis release factors that kill tubular cells and that induce further NET formation. In turn, necrotic tubular cells induce neutrophils to undergo NETosis. Thus, tubular and neutrophil death could enhance each other.

Postischemic Tubular Necrosis is Associated with Formation of NETs.

Figure 3A:
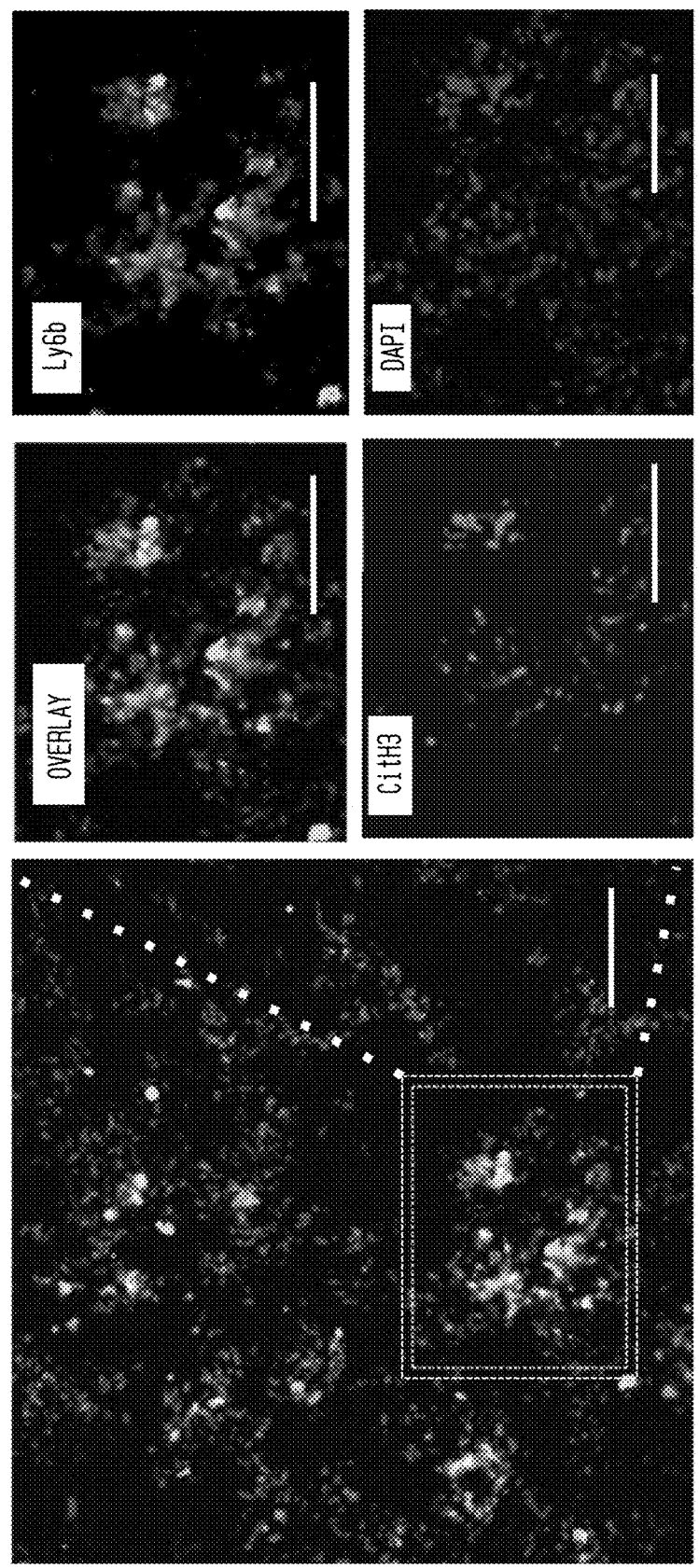
FIG. 3A. In vivo evidence for NETs in acute phase of IRI kidney. Representative NETs staining in outer medulla lesion of unilateral IRI kidney (ischemia 35 min, reperfusion 24 hous). Co-localization of CitH3 (Red), Ly6b(Green), and swelled nuclei (Blue) surrounding tubular duct indicates the NETs formation. Scale Bar: 50 µm.
Figure 3B:
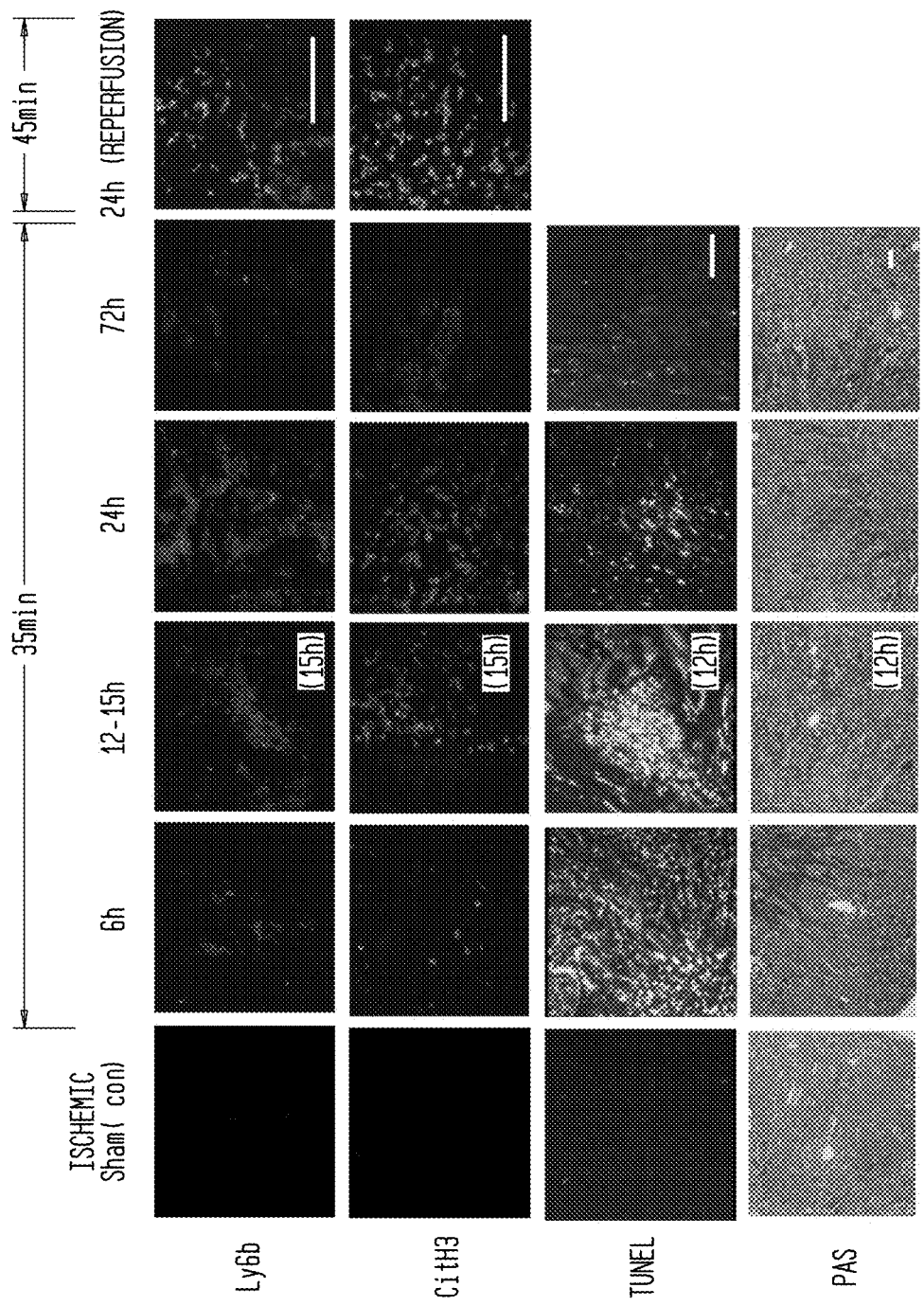
FIG. 3B. In vivo evidence for NETs in acute phase of IRI kidney. NETs staining of unilateral IRI kidney at different time point after reperfusion and different ischemia time. Figures show staining for Ly6b, CitH3, TUNEL and PAS. Scale Bar: 100 µm.
Figure 3C:
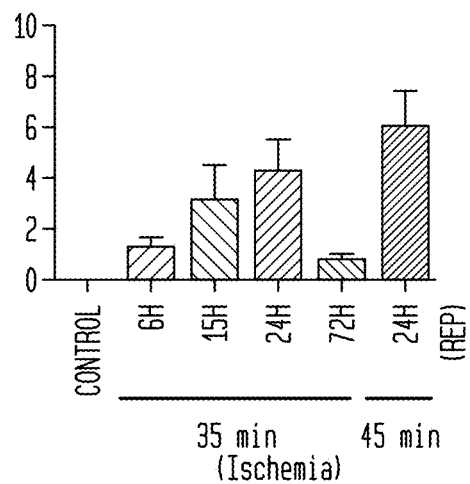
FIG. 3C. In vivo evidence for NETs in acute phase of IRI kidney. Ly6b positive area.
Figure 3D:
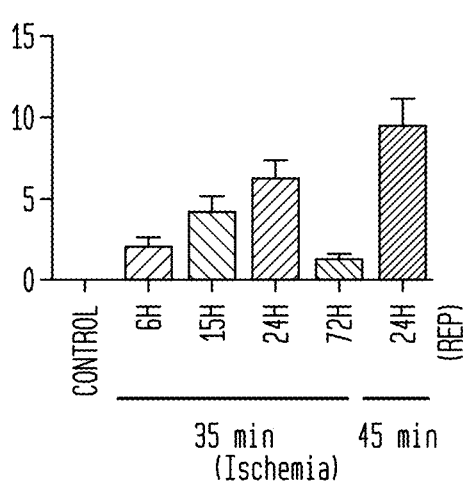
FIG. 3D. In vivo evidence for NETs in acute phase of IRI kidney. CitH3 positive area in IF staining.
Figure 3E:
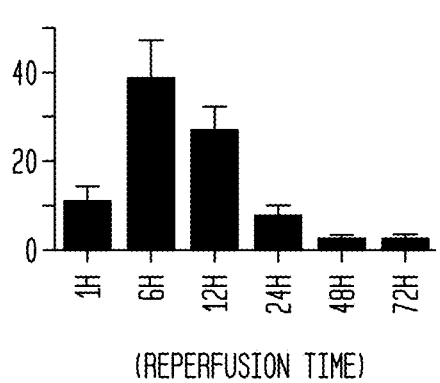
FIG. 3E. In vivo evidence for NETs in acute phase of IRI kidney. TUNEL area (%) as a function of reperfusion time.
Figure 3F:
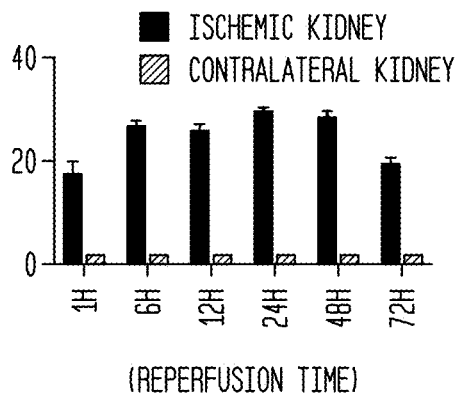
FIG. 3F. In vivo evidence for NETs in acute phase of IRI kidney. Histological evaluation was conducted by PAS staining. Injury score in time course of reperfusion. ischemia (K). Data are means±SEM from five mice in each group. TUNEL: Terminal deoxynucleotidyl transferase dUTP nick end labeling.
Figure 3G:
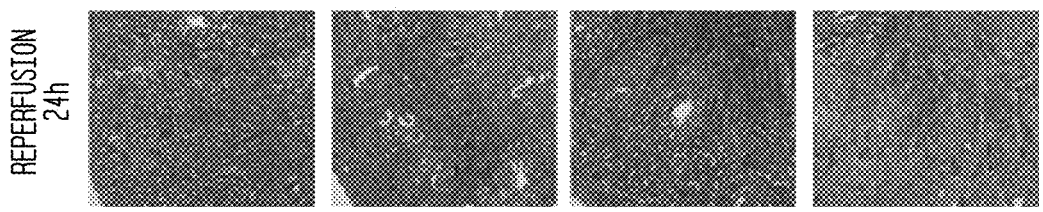
FIG. 3G. In vivo evidence for NETs in acute phase of IRI kidney. Histological evaluation was conducted by PAS staining. Representative image of tubular injury at different ischemic time. Scale Bar: 500 µm.
Figure 3H:
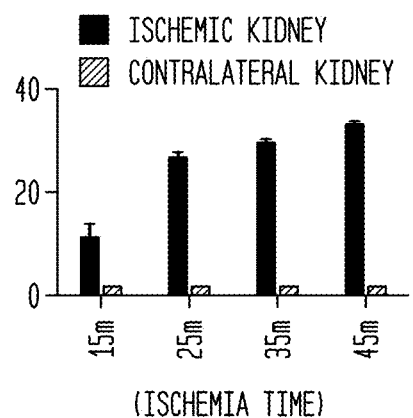
FIG. 3H. In vivo evidence for NETs in acute phase of IRI kidney. Histological evaluation was conducted by PAS staining. Injury score in time course of ischemia. Data are means±SEM from five mice in each group.
Figure 3I:
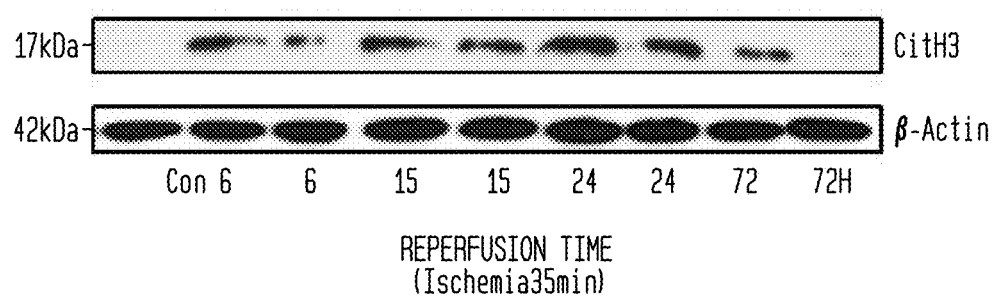
FIG. 3I. In vivo evidence for NETs in acute phase of IRI kidney. CitH3 expression of IRI kidney by Western blot.
Figure 4A:
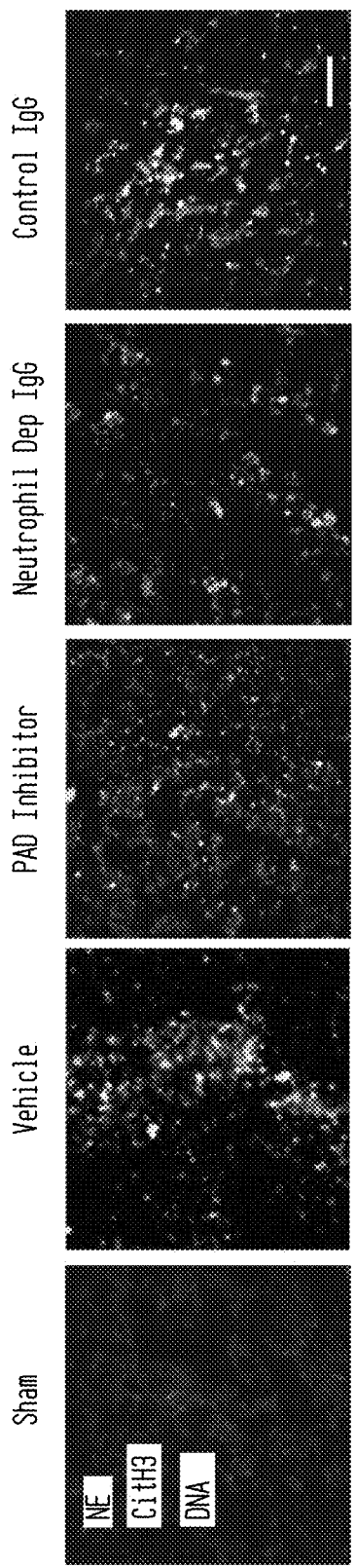
FIG. 4A. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Representative overlay figure of NETs staining in each group. NE: Green, CitH3: Red, DAPI: Blue. Scale Bar: 100 µm.
Figure 4B:
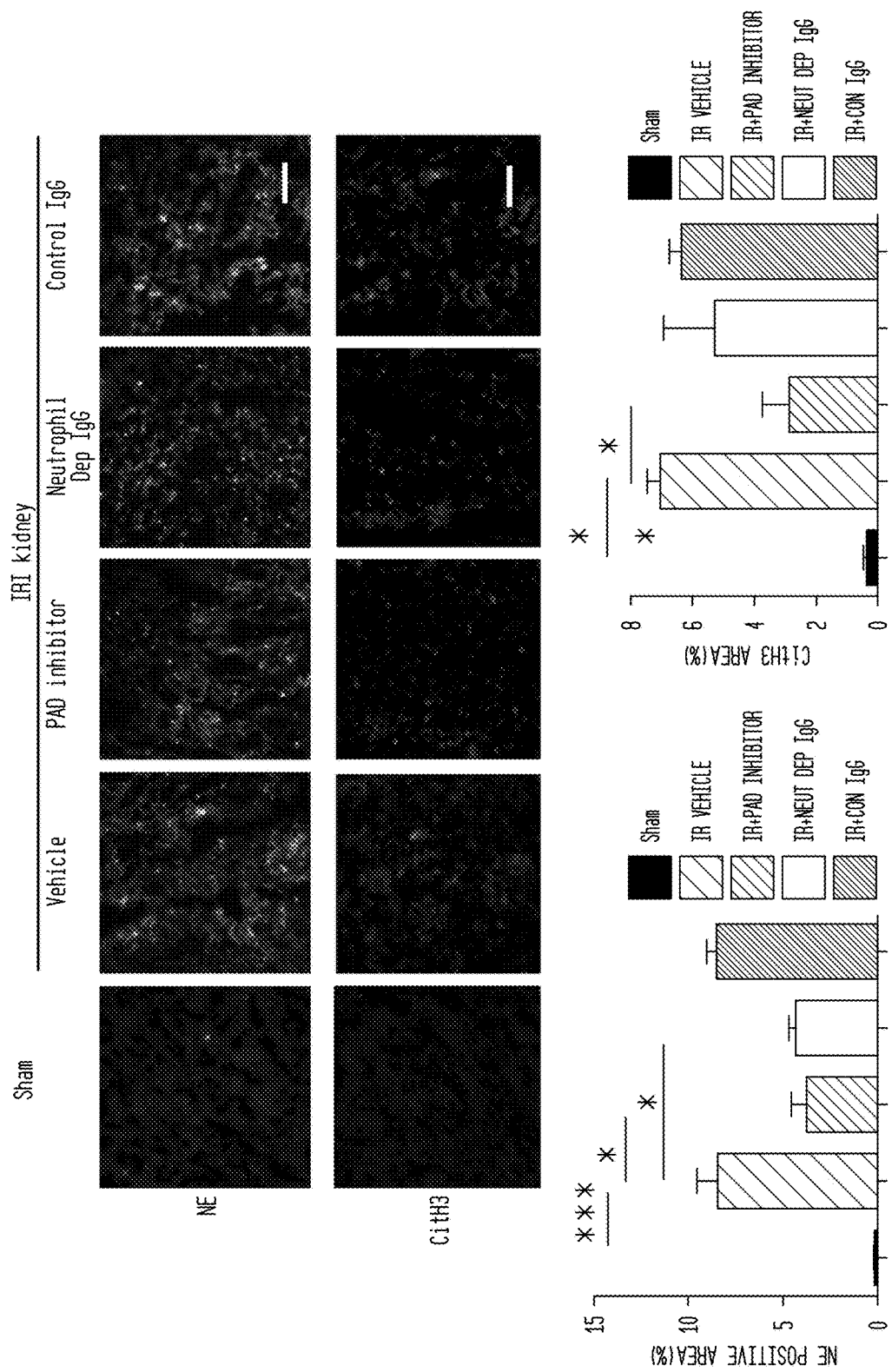
FIG. 4B. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Upper figures and graph show NE staining and the ratio of NE positive area. Lower figures and graph show CitH3 staining and the ratio of CitH3 positive area in different treatment group. Scale Bar: 100 µm.
Figure 4C:
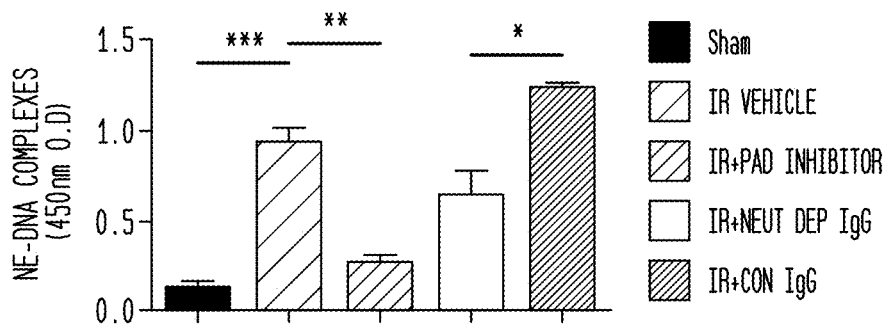
FIG. 4C. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Plasma creatinine levels in each group.
Figure 4D:
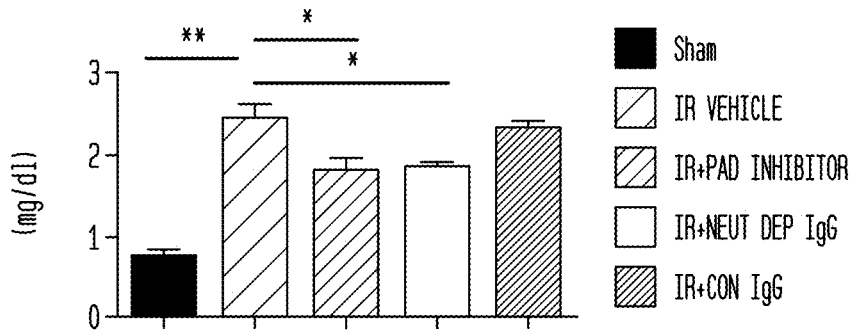
FIG. 4D. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Plasma urea levels in each group.
Figure 4E:
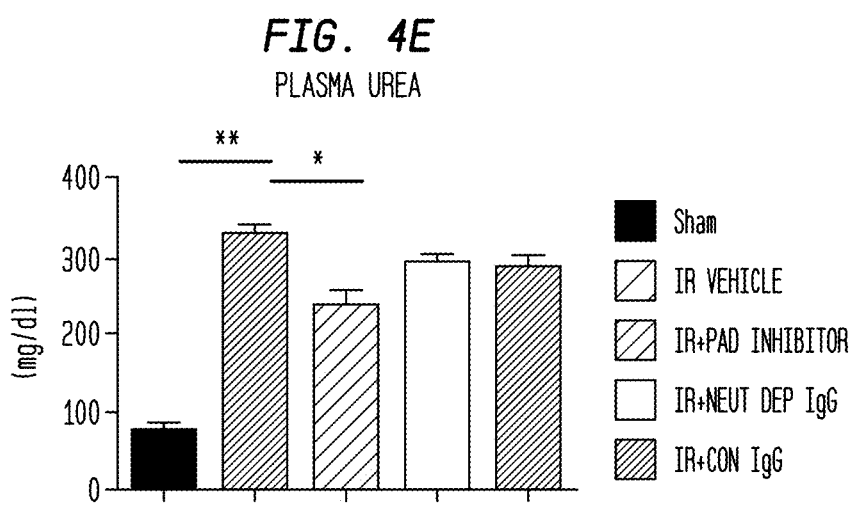
FIG. 4E. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Circulating NETs in each group.
Figure 4F:
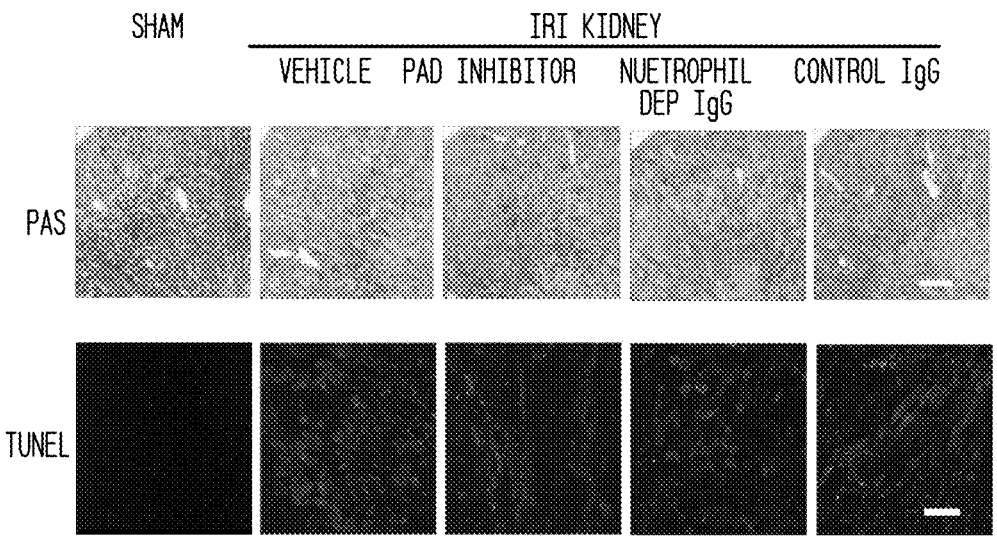
FIG. 4F. NET inhibitor ameliorates bilateral IRI kidney. Bilateral IRI kidney model mice (Ischemia 35 min, reperfusion 24 hours) were treated with vehicle (20% DMSO in PBS), PAD inhibitor (Cl-amidine 20 mg/kg, i.p.), and neutrophil depletion by injection of anti-Ly6G monoclonal antibody (500 µg anti-Ly6G IgGs (1A8) or control IgGs 24 and 2 hours before ischemia) before the surgery. Sham operated mice were prepared as a control (each group, N=5). Histological findings and TUNEL staining. Upper figures and graph shows representative PAS staining and tubular necrosis area, respectively (Scale bar: 500 um). Lower figures and graph show representative TUNEL staining and the ratio of TUNEL positive area, respectively (Scale Bar: 200 um). Data are means±SEM from five mice in each group. *P<0.05, P<0.01, *P<0.01 versus respective control.
Figure 4F:
Figure 4F:
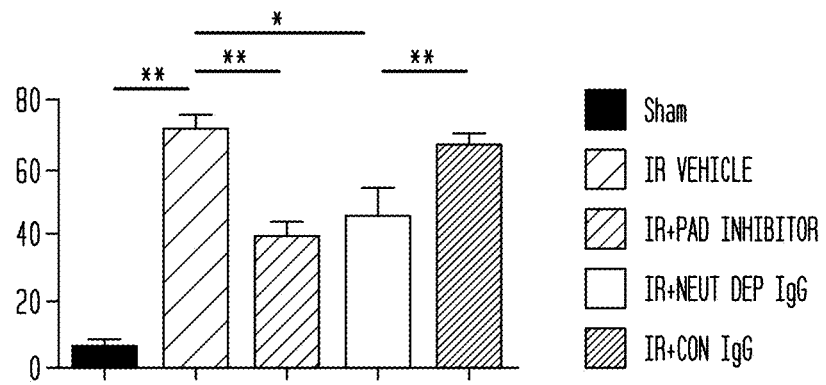
Figure 4F:
Figure 4F:
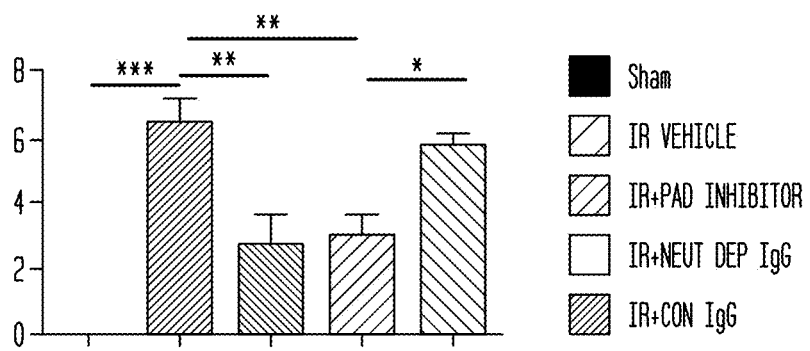

We hypothesized that infiltrating neutrophils form NETs in the post-ischemic kidney, which would imply release of more histones and other DAMPs that further accelerate AKI. Postischemic AKI was induced in wild type mice by unilateral clamping of the renal pedicle for 35 minutes followed by reperfusion for 0 h-72 h. Postischemic kidneys (unilateral ischemia time 35 min, reperfusion 24 h) displayed positivity for CitH3 and Ly6b co-localizing with NETs in areas of S3 segment tubular necrosis of the outer stripe of the outer medulla as assessed by immunofluorescence (FIG. 3A) and immunohistochemistry staining (not shown). The number of NETs in the outer medulla increased between 15 h~24 h after reperfusion and decreased thereafter as determined by immunofluorescence staining (FIG. 3B-3D) and western blotting (FIG. 3E). Similarly, circulating NET components in plasma were detected 15~24 h after reperfusion (not shown). Interestingly, renal cell death in the outer stripe of the outer medulla preceded NET formation, between 1 h~6 h after reperfusion as demonstrated by terminal deoxynucleotidyl transferase dUTP nick-end labelling (TUNEL)-positivity in that area (FIGS. 3F and 3G) as well as by detection of free DNA in plasma (not shown). Histological analysis showed that tubule necrosis persisted for a long time after the peak of TUNEL positivity and NETs abundance (FIG. 3H-3K). These results show that necrosis of some tubular cells is an early event upon IRI followed by neutrophils undergoing NETosis, which is associated with ongoing tubular injury NET Formation Contributes to Post-Ischemic Tubular Necrosis In Vivo.

To determine whether NET formation drives ongoing tubular injury, bilateral IRI kidney mice (ischemia 35 min, reperfusion 24 h) underwent either treatment with a PAD inhibitor or with neutrophil depletion by injection of anti-Ly6G monoclonal antibody. The PAD inhibitor substantially reduced the abundance of NETs in the post-ischemic kidney (FIG. 4A, 4B) as well as NET components in plasma (FIG. 3C). Furthermore, renal function (FIGS. 4D and 4E), tissue necrotic area (FIG. 4F), and the expression of AKI marker genes (not shown) were significantly reduced in the mice treated with the PAD inhibitor as well as neutrophil depletion. We conclude that neutrophils contribute to post-ischemic AKI by forming NETs.

Dual Inhibition of NET Formation and Cell Necrosis has Additive Protective Effects on Post-Ischemic AKI.

Figure 5A:
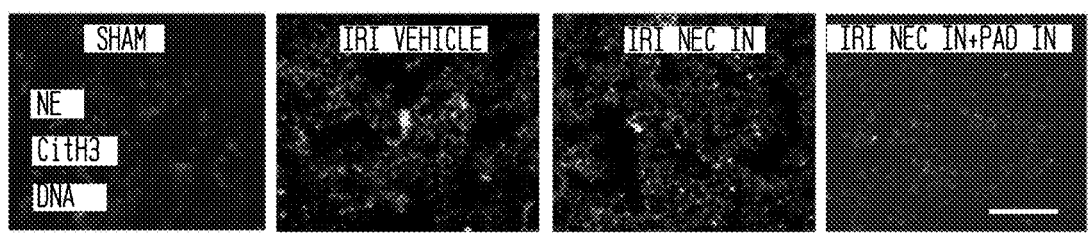
FIG. 5A. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Representative NETs staining in IRI kidney treated with vehicle, necrosis inhibitor (Nec In) and the combination Nec In and PAD inhibitor (PAD In). NE: Green, CitH3: Red, DAPI: Blue. Scale Bar: 200 µm.
Figure 5B:
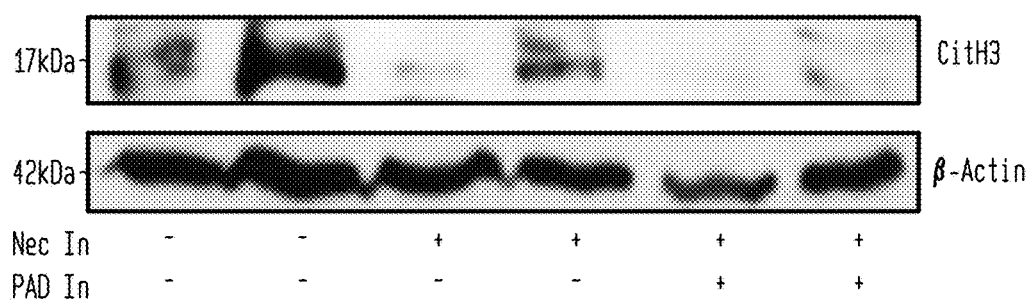
FIG. 5B. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Representative protein expression of CitH3 in IRI kidney treated with different inhibitors.
Figure 5E:
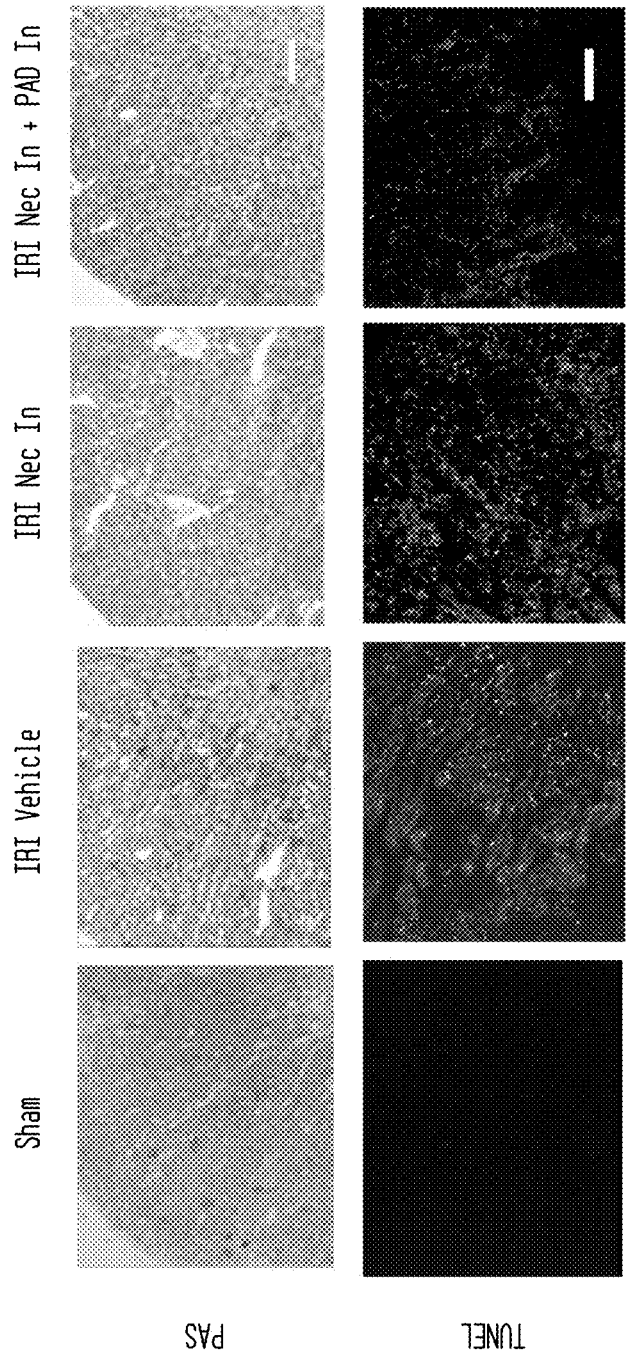
FIG. 5E. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Representative PAS (upper figures, Scale Bar: 500 um) and TUNEL staining (lower figures, Scale Bar: 200 µm).
Figure 5F:
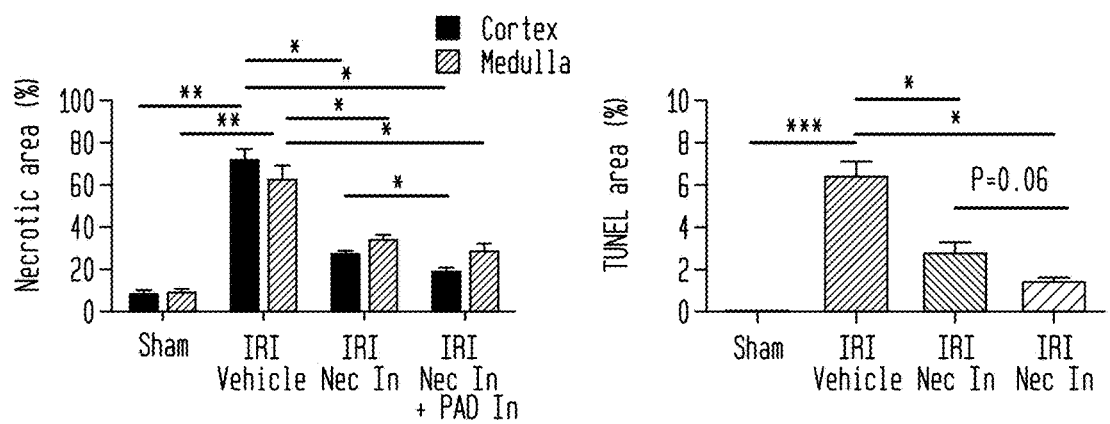
FIG. 5F. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. The quantification of necrotic area in PAS staining (upper graph) and TUNEL positive area (lower graph).
Figure 5G:
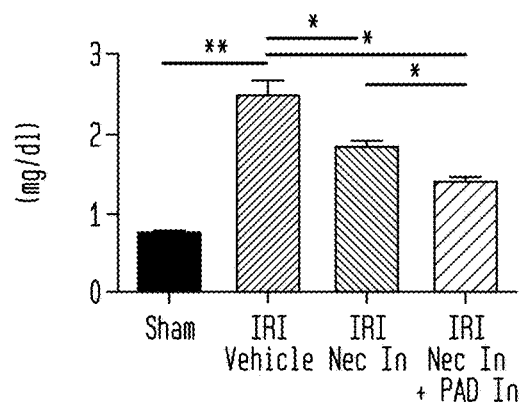
FIG. 5G. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Plasma creatinine and (H) plasma urea in each group. Data are means±SEM from at least five mice in each group. *P<0.05, P<0.01, *P<0.01 versus respective control.
Figure 5H:
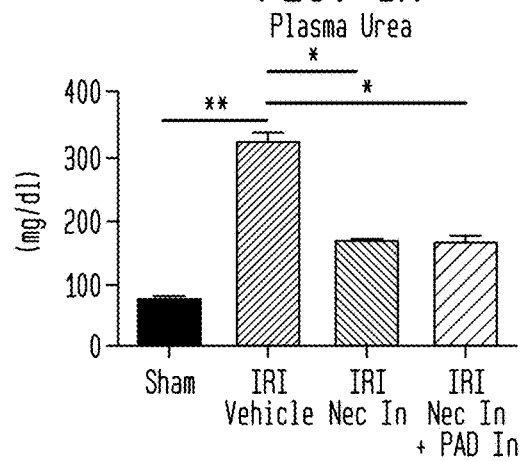
FIG. 5H. NET inhibition had additional protective effect on necrosis inhibition in IRI kidney. Bilateral IRI kidney model mice (ischemia 35 min, reperfusion 24 hours) were treated with vehicle (20% DMSO in PBS, N=14), necrosis inhibitor cocktail (Necrostatin-1; 1.65 mg/kg i.p.), Ferrostatin-1 (2 mg/kg i.p.), Cyclosporine (10 mg/kg, i.v, N=5) and the combination of necrosis inhibitor cocktail and PAD inhibitor (Cl-amidine 20 mg/kg, i.p., N=5) before the surgery. Plasma urea in each group.

To study the contribution of regulated necrosis and NETosis to renal necroinflammation we tested dual NET and necrosis inhibition in mice with post-ischemic AKI. Necrosis inhibition reduced the abundance of NETs (FIG. 5A-5D), necrotic area (FIGS. 5E and 5F), and AKI-related gene expression (not shown) and improved renal function (FIGS. 5G and 5H). Adding a PAD inhibitor to necrosis inhibition abrogated intrarenal NET formation, further improved renal dysfunction, reduced tubular necrosis (FIGS. 5A-5E and 5G) and decreased induction of injury-related genes compared to necrosis inhibition alone (not shown). Together, these results show that NET formation is an accelerating element of the crescendo of necroinflammation in the post-ischemic kidney.

Histones are Central Mediators of Necroinflammation in AKI.

Figure 6A:
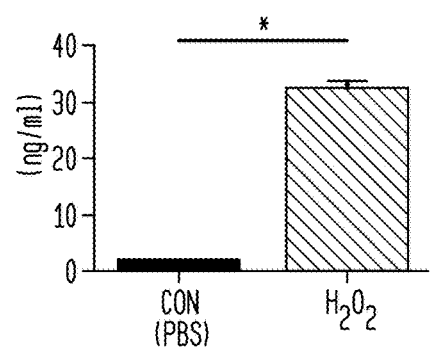
FIG. 6A. Histones are central key players of necroinflammation including NETosis. Histone concentration of the supernatant in HK2 cells treated with 1 mM $H_2O_2$ and PBS for 24 hours was measured by histone ELISA detection kit. Data represent the means±SEM of 4 independent experiments. *P<0.05, versus respective control.
Figure 6B:
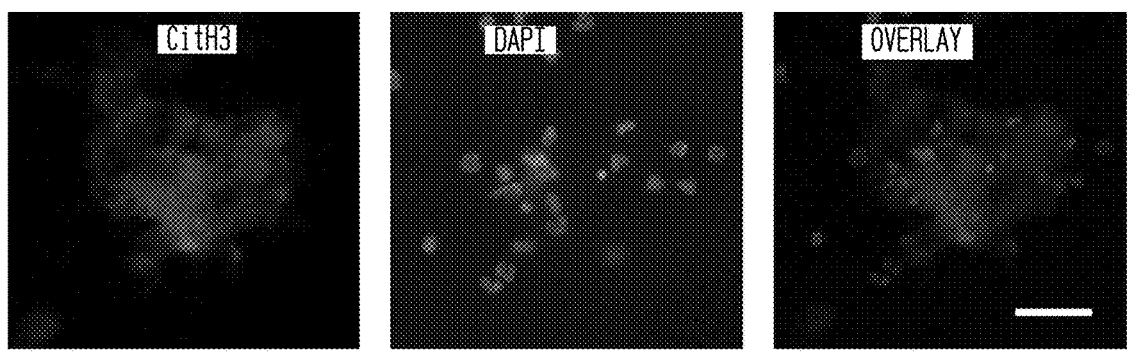
FIG. 6B. Histones are central key players of necroinflammation including NETosis. Representative NETs staining of histone stimulated neutrophils using CitH3 (Red) and DAPI (Blue). Scale Bar: 50 μm.
Figure 6C:
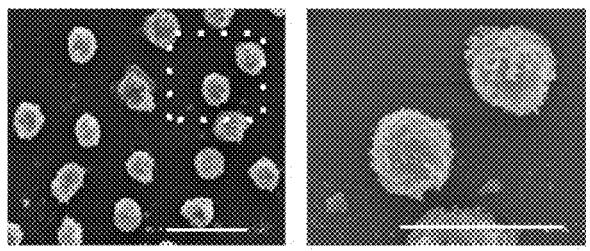
FIG. 6C. Histones are central key players of necroinflammation including NETosis. Representative Scanning Electron microscopy images of unstimulated neutrophils (upper) and histone-stimulated neutrophils (lower). Scale Bar: 20 μm.
Figure 6C:
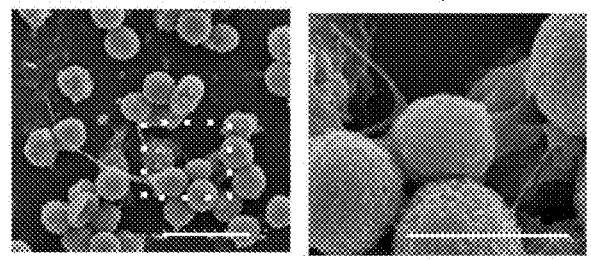
Figure 6D:
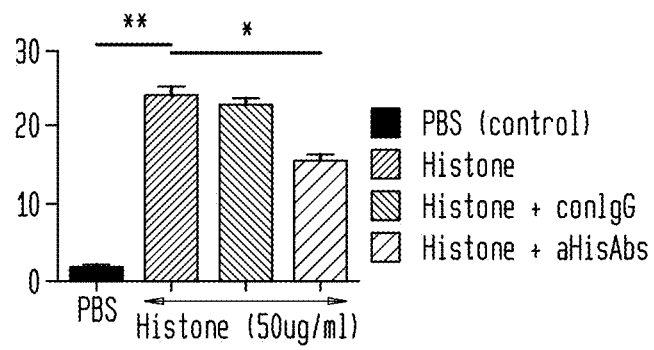
FIG. 6D. Histones are central key players of necroinflammation including NETosis. Neutrophils were treated with exogenous histones (50 μg/ml) in the presence of neutralizing histone abs (aHisAbs) (100 ug/ml) and control Abs (100 μg/ml) and the ratio of CitH3 positive cells was quantified.
Figure 6E:
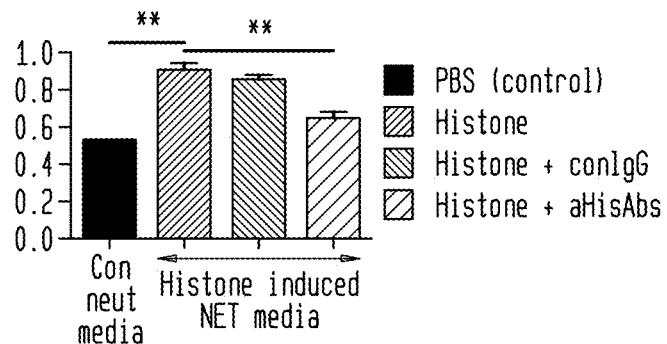
FIG. 6E. Histones are central key players of necroinflammation including NETosis. The supernatants of histone-stimulated neutrophils were applied to HK2 cells and the cytotoxicity was determined by LDH assay. The conditioned media was prepared as previously described to avoid the contamination of exogenous histones. Data represent the means±SEM of 4 independent experiments. *P<0.05, **P<0.01, versus respective control.
Figure 6F:
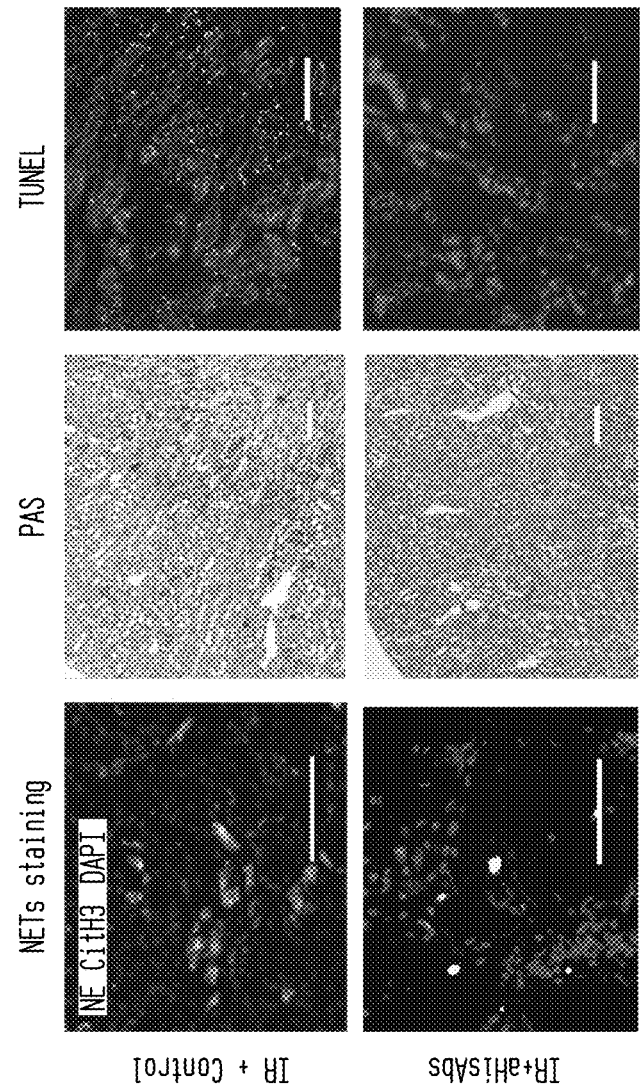
FIG. 6F. Histones are central key players of necroinflammation including NETosis. Representative image of NETs (left), PAS (middle), and TUNEL (right) staining in IRI kidney treated with control (upper) and aHisAbs (lower, aHisAbs 20 mg/kg, i.p, N=5) NE: Green, CitH3: Red, DAPI: Blue. Scale Bar: 200 μm.

To examine which components of necrotic cells induce NETs and which components of NETs injure tubular cells, we focused on histones because histones have unique cytotoxic DAMP effects (Allam et al., 2014, J Mol Med (Berlin) 92:465-72). Necrotic HK-2 cells treated with $H_2O_2$ released histones into the supernatant (FIG. 6A). To test if histones are sufficient to induce neutrophils to undergo NET formation, we exposed neutrophils from healthy human donors to extracellular histones. 3 h later, the neutrophils had formed aggregated NETs and showed CitH3 positivity (FIGS. 6B and 6C). Histone-induced NET formation could be inhibited with a histone-neutralizing BWA3 antibody (aHisAbs) (FIG. 6D). To examine the toxicity of histone-induced NETs to tubular cells, the supernatants of NETs were applied to HK-2 cells. At 20 h of incubation, NETs supernatants induced HK-2 cell death, a process suppressed by adding aHisAbs, which suggests that histones are a central element of NET-related tissue injury (FIG. 6E).

Figure 6G:
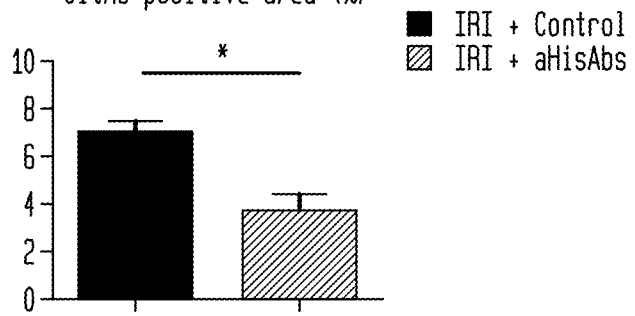
FIG. 6G. Histones are central key players of necroinflammation including NETosis. (G) The quantification of CitH3 positive NETs area.
Figure 6H:
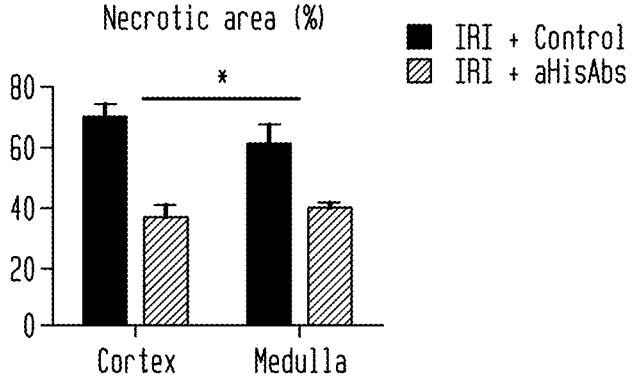
FIG. 6H. Histones are central key players of necroinflammation including NETosis. Histological necrotic area.
Figure 6I:
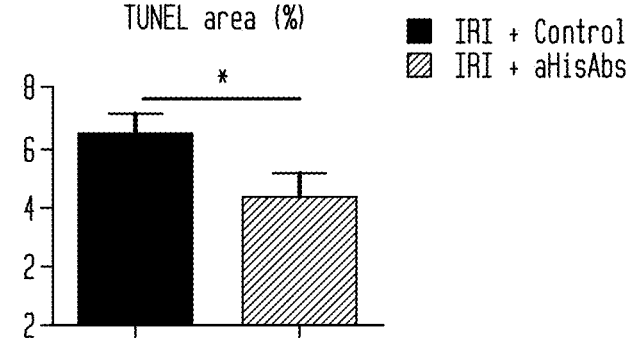
FIG. 6I. Histones are central key players of necroinflammation including NETosis. TUNEL positive area.
Figure 6J:
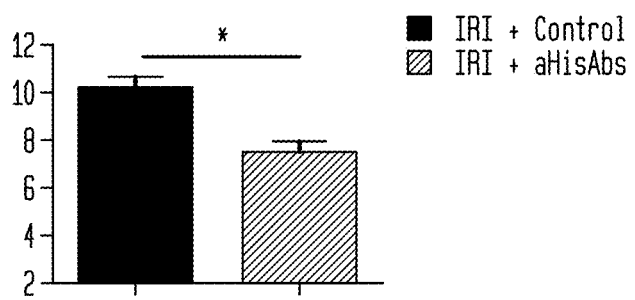
FIG. 6J. Histones are central key players of necroinflammation including NETosis. Plasma creatinine in IRI kidney mice treated with control and aHisAbs. Data show the means±SEM from at least five mice in each group. *P<0.05, versus respective control.

To examine whether aHisAbs could suppress also the vicious cycle of tubular necrosis and NET formation, bilateral IRI kidney mice were treated with aHisAbs before the surgery. aHisAbs reduced the abundance of NETs as assessed by immunofluorescence staining (FIGS. 6F and 6G) and western blotting (not shown). Consistent with the decreased abundance of NETs, tubular necrosis, renal dysfunction, and the expression of kidney injury marker genes were suppressed (FIG. 6F, 6H-6J). Together, histones released from dying tubular cells and from NETs contributed to renal necroinflammation in AKI.

Upon AKI Circulating NETs and Histones Promote Remote Organ Injury.

Figure 7A:
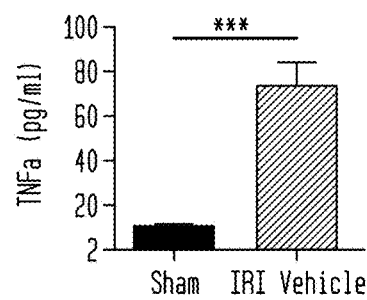
FIG. 7A. AM-related remote organ injury is caused by circulating NETs and DAMPs such as histones. Plasma TNF-α in sham operated mice and bilateral IRI kidney mice (ischemia 35 min, reperfusion 24 h) was measured by ELISA.
Figure 7B:
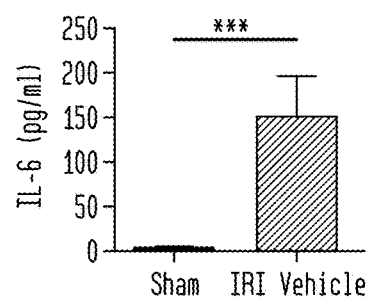
FIG. 7B. AM-related remote organ injury is caused by circulating NETs and DAMPs such as histones. Plasma IL-6 in sham operated mice and bilateral IRI kidney mice (ischemia 35 min, reperfusion 24 h) was measured by ELISA FIG. 7C. AM-related remote organ injury is caused by circulating NETs and DAMPs such as histones. Plasma histone 3 content in sham operated mice and bilateral IRI kidney mice (ischemia 35 min, reperfusion 24 h) was measured by western blotting. As a positive control for plasma histone, the plasma of LPS-induced sepsis mice was used.
Figure 7C:
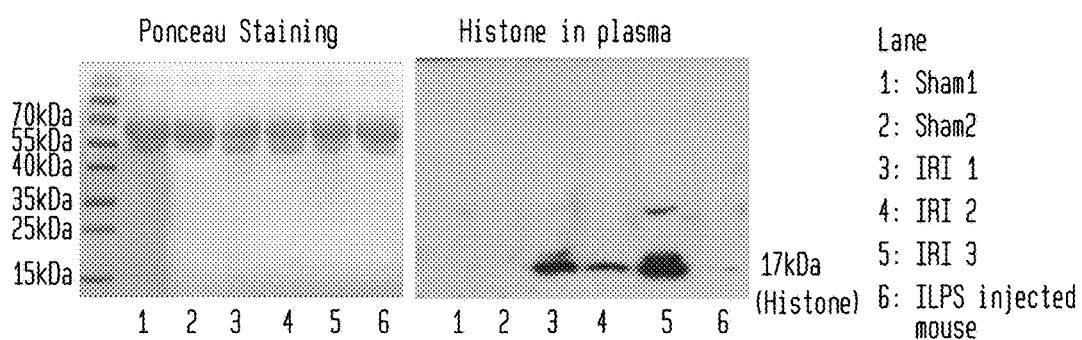
FIG. 7D. AM-related remote organ injury is caused by circulating NETs and DAMPs such as histones. Tissue injury in multi-organ (kidney, lung, liver, brain, heart and pancreas) of sham and bilateral IRI (ischemia 35 min, reperfusion 24 h) kidney mice was evaluated by TUNEL staining. Scale Bar: 100 μm.
FIG. 7E. AM-related remote organ injury is caused by circulating NETs and DAMPs such as histones. Neutrophil infiltration in multi-organ (kidney, lung, liver, brain, heart and pancreas) of sham and bilateral IRI (ischemia 35 min, reperfusion 24 h) kidney mice was evaluated by Ly6b-immunostaining. Scale Bar: 100 μm.
FIG. 7F. AM-related remote organ injury is caused by circulating NETs and DAMPs such as histones. NETs expression in multi-organ (kidney, lung, liver, brain, heart and pancreas) of sham and bilateral IRI (ischemia 35 min, reperfusion 24 h) kidney mice was evaluated by western blotting.
FIG. 7G. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs was evaluated by NETs immunostaining (upper figures, NE: Green, CitH3: Red, DAPI: Blue) and TUNEL staining (lower figures). Scale Bar: 100 μm.
FIG. 7H. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The graph shows NETs area (H) in lung. *P<0.05, P<0.01, *P<0.01 versus respective control. #p<0.05, compared to aHisAbs group.
FIG. 7I. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The graph shows TUNEL positive area in lung. *P<0.05, P<0.01, *P<0.01 versus respective control. #p<0.05, compared to aHisAbs group.
FIG. 7J. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The cell number in bronchoalveolar lavage (BAL) of these groups was counted. *P<0.05, P<0.01, *P<0.01 versus respective control. #p<0.05, compared to aHisAbs group.
FIG. 7K. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The quantification of TUNEL positive area in liver in each group. *P<0.05, P<0.01, *P<0.01 versus respective control. #p<0.05, compared to aHisAbs group.
FIG. 7L. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The quantification of TUNEL positive area in heart in each group. *P<0.05, P<0.01, *P<0.01 versus respective control. #p<0.05, compared to aHisAbs group.
FIG. 7M. AM-related remote organ injury is caused by circulating NETs and DAMPs such as histones. Lung injury followed bilateral IRI kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. The quantification of TUNEL positive area in brain in each group. *P<0.05, P<0.01, *P<0.01 versus respective control. #p<0.05, compared to aHisAbs group.
FIG. 7N. AM-related remote organ injury is caused by circulating NETs and DAMPs such as histones. Lung injury followed bilateral IM kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. Plasma TNF-α in different treated mice was measured by ELISA method. Data show the means±SEM from at least five mice in each group. *P<0.05, P<0.01, *P<0.01 versus respective control. #p<0.05, compared to aHisAbs group.
FIG. 7O. AM-related remote organ injury is caused by circulating NETs and DAMPs such as histones. Lung injury followed bilateral IM kidney (ischemia 35 min, reperfusion 24 h) treated with vehicle, PAD inhibitor, neutrophil depletion, Necrosis inhibitor, Necrosis inhibitor+PAD inhibitor, neutralizing aHisAbs. IL6 in different treated mice was measured by ELISA method. Data show the means±SEM from at least five mice in each group. *P<0.05, P<0.01, *P<0.01 versus respective control. #p<0.05, compared to aHisAbs group.
Figure 7D:
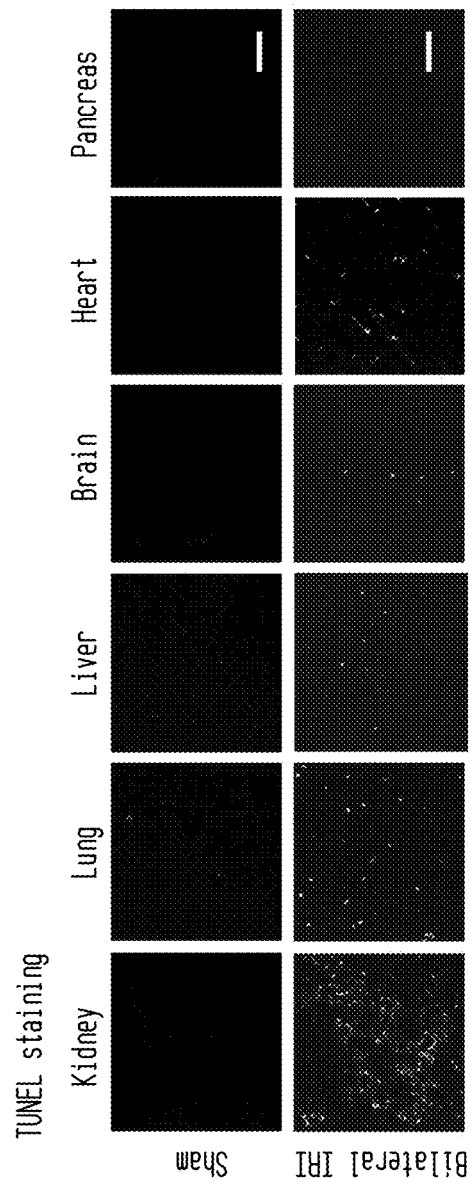
Figure 7E:
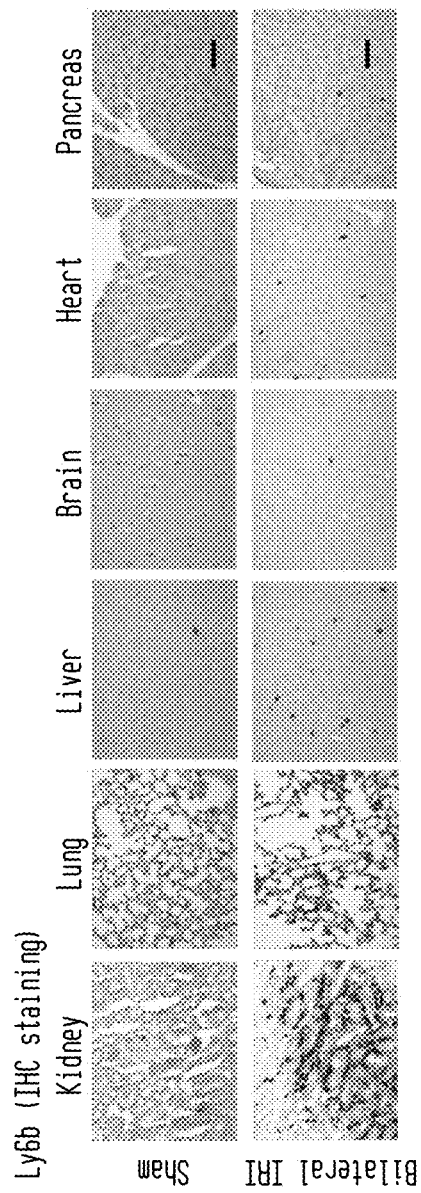
Figure 7F:
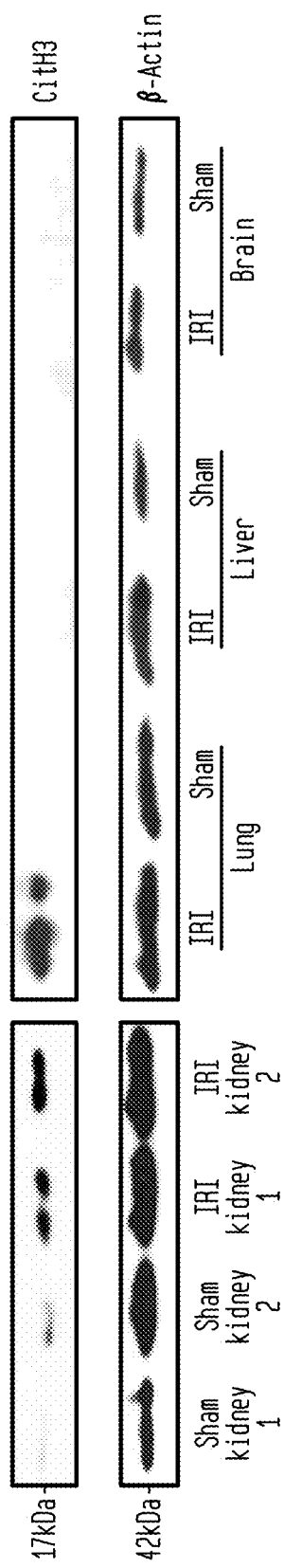
Figure 7G:
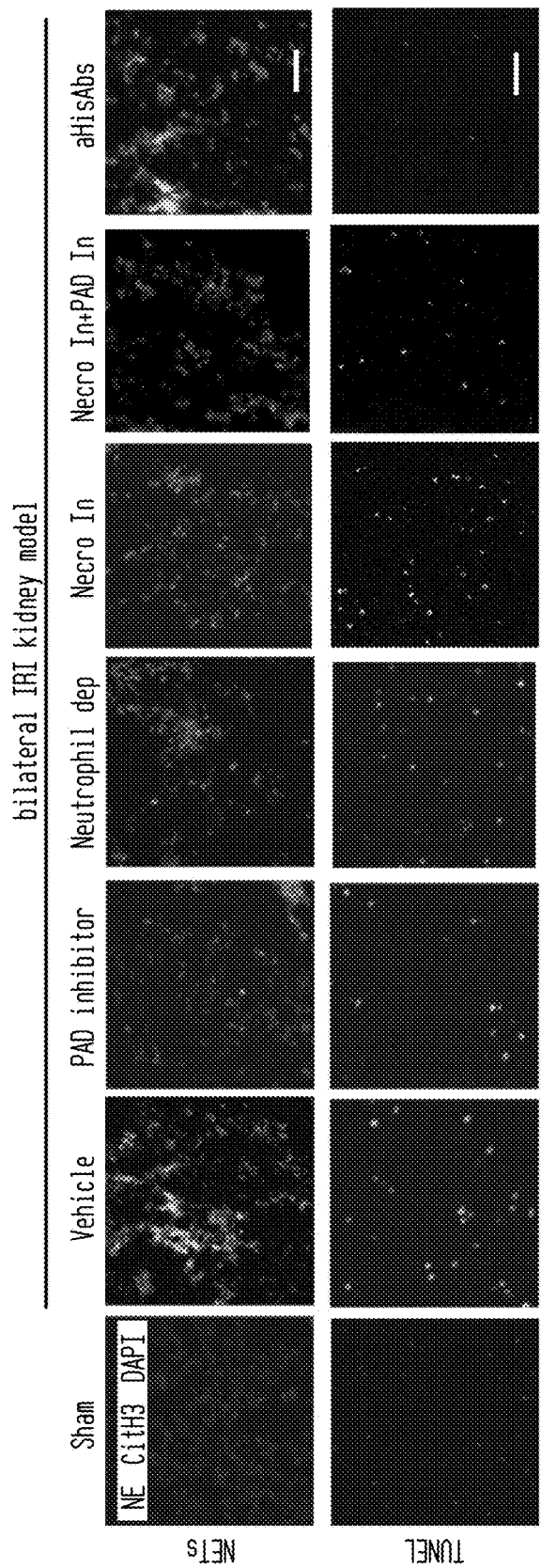
Figure 7H:
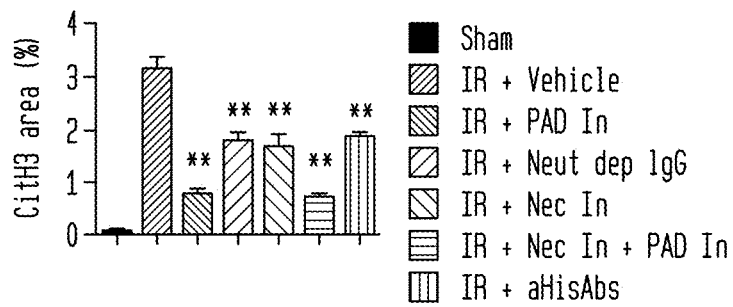
Figure 7I:
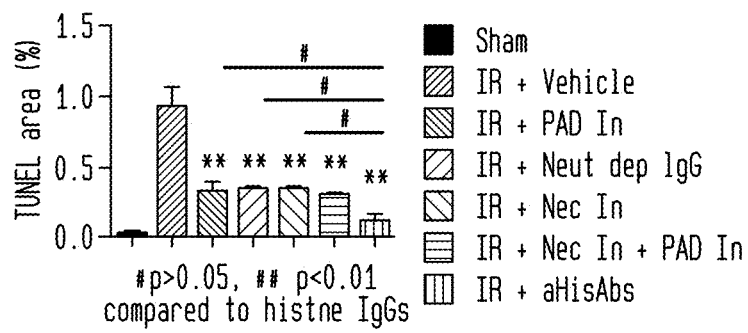
Figure 7J:
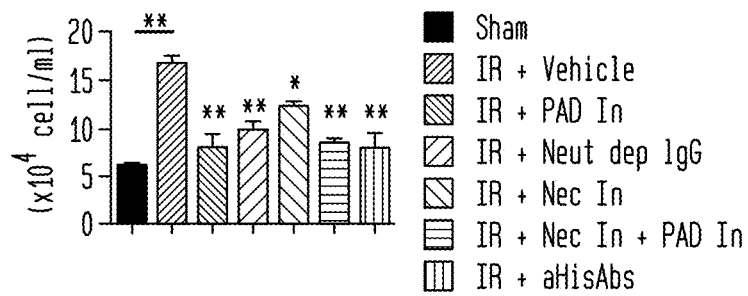
Figure 7K:
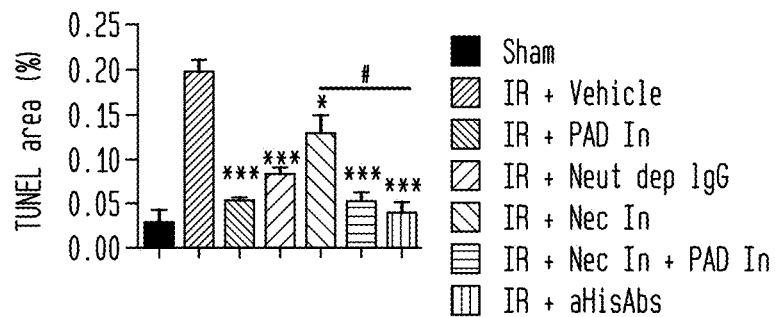
Figure 7L:
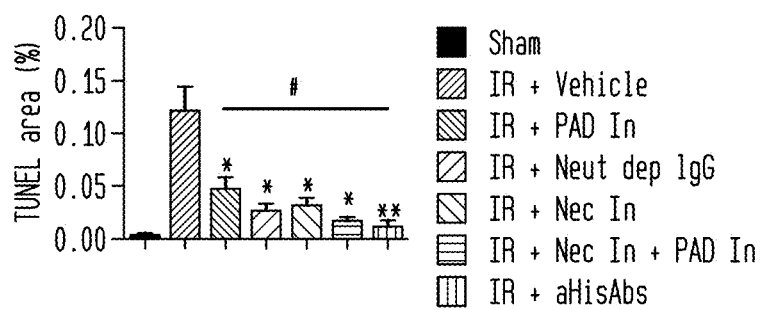
Figure 7M:
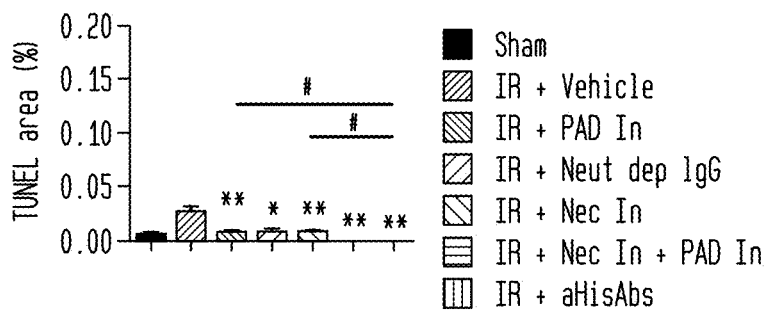
Figure 7N:
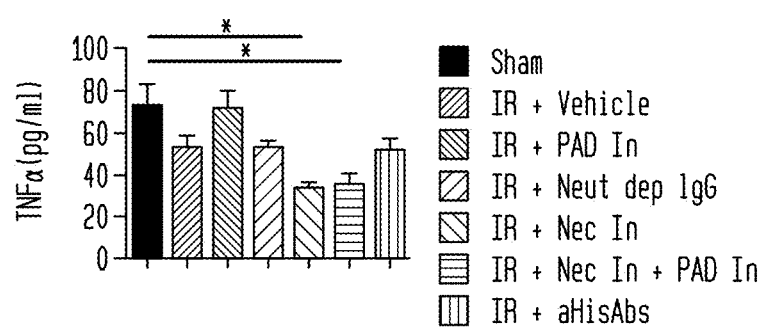
Figure 7O:
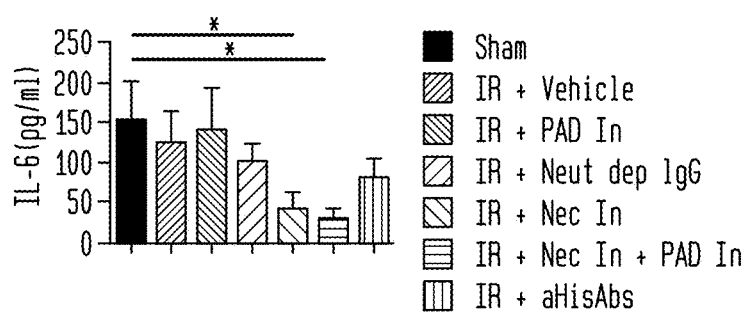

The molecular mechanisms underlying AKI-related remote organ injury were previously unknown. Since we had found that post-ischemic AKI is associated with NETs and DAMPs in the plasma we speculated that the injured kidney releases NETs and their cytotoxic components into the circulation, promoting injury in other organs. Indeed, mice with bilateral IRI displayed not only NETs but also increased plasma concentrations of histones, tumor necrosis factor (TNF)-α and IL-6 (FIG. 7A-7C). To assess remote organ injury, TUNEL staining and neutrophil immunostaining were performed in lung, liver, brain, heart, and pancreas after bilateral IRI surgery. TUNEL-positive cells and neutrophil infiltration were identified in multiple organs (lung, liver, brain, heart) (FIG. 7D, 7E) but western blotting of lysates from these organs detected histone citrullination only in kidney and lung (FIG. 7F). Furthermore, NETs were detected in lung by immunofluorescence staining (FIG. 7G), but not in other organs (data not shown). The area of NETs in lung correlated with the TUNEL-positive area and the number of cells in bronchoalveolar lavage fluid (BAL) (FIG. 7H, 7I, 7J). NET area and BAL cell number peaked between 6 h-24 h after reperfusion in the unilateral IRI kidney model (not shown) and NETs components were detected in BAL supernatant of bilateral IRI mice (not shown). Meanwhile, NETs and necrosis inhibition reduced these markers of lung injury and also reduced remote organ injury to liver, heart, and brain (FIG. 7K-7M) and systemic inflammation (FIGS. 7N and 7O). aHisAbs were especially effective for preventing remote organ injury (FIG. 7I, 7K-7M). These results show that circulating histones promote lung injury and remote organ injury following renal IRI.

Discussion

We hypothesized that several of the infiltrating neutrophils during AKI undergo NETosis, leading to the release of cytotoxic DAMPs such as histones, which exacerbates kidney tubular injury and interstitial inflammation. Furthermore, we speculated that such NET components enter the circulation and contribute to remote organ injury that is often associated with AKI, e.g. in multi-organ failure. Our study revealed that post-ischemic tubular necrosis involves DAMP release, promoting NET formation as a second event, a process that results in further renal and extrarenal injury.

The pathophysiology of AKI involves regulated cell death and inflammation (Linkermann et al., 2014, Proc Natl Acad Sci USA 111:16836-41). In particular, necroptosis, ferroptosis, and MPT-RN of TCs result in the release of DAMPs, leading to the recruitment of inflammatory cells and further injury (Linkermann et al., 2013, Proc Natl Acad Sci USA 110:12024-9). Numerous neutrophils were detected in the early phase of ischemic AKI (Lech et al., 2013, Kidney Int 83:647-61) and neutrophil depletion prevented renal dysfunction, indicating the contribution of neutrophils to AKI (Hayama et al., 2006, Transplant Proc 38:2201-2).

We found the presence of NETs in kidney biopsies of patients with acute tubular necrosis, which is consistent with data from non-infectious human kidney diseases such as ANCA vasculitis (Kessenblock 19448636, Kumar et al., 2015, J Am Soc Nephrol 26:2399-413). Based on these findings, we speculated that hypoxia-induced necrotic TCs activate neutrophils to promote NET formation, which induced further TC injury and further NETs formation. These indicate that tubular necrosis and NETosis could enhance the inflammation and surrounding tissue damage induced by each other, i.e. renal necroinflammation. Indeed, the IRI kidney was protected by treatment with an inhibitor of NET formation, which is consistent with previous findings in glomerular disease (Kumar et al., 2015, J Am Soc Nephrol 26:2399-413, 23722903).

Cl-amidine is a pan-PAD enzyme inhibitor that can inhibit all types of PAD in other cells. PAD4 is located inside neutrophil nuclei, where it facilitates citrullination of histones. Other PAD enzymes are mostly absent from the kidney (Wong et al., 2015, Nat Med 21:815-9). Although PAD4 is expressed in tubular cells (Ham et al., 2014, Am J Physiol Renal Physiol 307:F1052-62), the precise pathophysiology in injured TCs remains unclear. Our in vitro data show that conditioned NET media pretreated with PAD inhibitor reduced the damage of TCs. This shows that the PAD inhibitor in our study mainly inhibited NETosis by affecting PAD4 activity in neutrophils. Furthermore, we demonstrated that dual inhibition of NET formation and cell necrosis has additive protective effects on IRI kidney.

Although RIPK3/CypD double knockout mice (Linkermann et al., 2013, Proc Natl Acad Sci USA 110:12024-9), which have defects in necroptosis and MPT-RN, are prevented from IRI-induced kidney damage, chemical inhibitors of these processes such as necrostatin 1, ferrostatin 1, and sanglifehrin A did not completely prevent kidney injury. Thus, our data indicate that although these inhibitors prevented some TCs death, the amount of DAMPs that was released from the fewer TCs undergoing necrosis was still sufficient to induce NETs formation, and the NETs could be inhibited by PAD inhibitor. Nevertheless, the additive effect of dual therapy was not large compared to necrosis inhibitor alone, which raises the possibility that in the necrosis inhibitor cocktail, 1) necrostatin 1 could inhibit neutrophil necroptosis and NET formation via suppressing the RIPK1/RIPK3/pMLKL signalling pathway (Desai et al. 2016, Eur J Immunol 46:223-9), and 2) cyclosporine, which was used for blocking MPT-RN, could react with calcineurin to inhibit NET induction (Gupta et al., 2014, PLoS One 9:e97088). Consequently, these agents could inhibit the formation of NETs. However, it is unclear whether these inhibitors could affect the PAD4-citrullinated histone pathway in neutrophils.

Our study indicated that remote organ injury following AKI at least partially relates to formation of NETs. In particular, the lungs are the most common site of remote injury, since the permeability of lung capillaries increases during AKI (Ware & Matthay, 2000, N Engl J Med. 342: 1334-49). In this study, we demonstrated that NETs also form in the lungs in association with IRI kidney inducing acute lung injury (ALI).

One possible mechanism why NETs mostly occurred in lungs as a remote organ seems to be that pre-NET-forming neutrophils, which passed through the injured kidney and were stimulated by highly concentrated DAMPs, would anatomically return to the lung and could easily become trapped in vessels because capillaries in lung have a narrower bore compared with those in other organs (Bathe et al., 2002, Biophys J 83:1917-33). Doi et al. (2014, Kidney Int 86:316-26) revealed that in bilateral nephrectomy mice, HMGB1 among DAMPs affected ALI via TLR4 signalling, but in bilateral IRI kidney mice, it induced ALI independent from TLR4. These findings seem to be compatible with those of our study, since IRI could induce necroinflammation including NETs formation to activate various receptors as well as TLR4. For example, histones can activate TLRs 2, 4, and 9, while HMGB1 can activate TLRs 2, 4, 9 and receptor for advanced glycation end-products (Chen et al. 2016, Acta Pharm Sin B 6:183-8).

The inhibitors of NETs and necrosis also protected against other remote organ injuries via blocking circulating histones, cytotoxic cytokines, and circulating NETs components. Among these treatments, aHisAbs were the most effective intervention to protect distant organs against damage, which indicates that histones are one of the most important DAMPs mediating AKI-related remote organ injury. Although inhibitors of NETs and necrosis are supposed to prevent remote organ injury via regulating the cell death pathway caused by DAMPs, neutralizing histones could possibly contribute to inhibiting the direct toxicity of histones (Chen et al., 2014, Cell Death Dis 5:e1370) as well as TLR activation, which could not be inhibited by NETs and necrosis inhibitors. The direct cytotoxicity is known to be due to the high positive charge, which affects the cell membrane to induce a damage of cells (Gillrie et al., 2012, Am J Pathol 180:1028-39). Conversely, inhibitors of NETs and necrosis showed a trend towards a better protective effect against kidney damage during IRI compared with that of aHisAbs. These findings indicate that the site of necro-inflammation might be more effectively spatiotemporally regulated by blocking intracellular signaling arising from IRI than by neutralizing locally produced histones.

In conclusion, during IRI of kidney, the necrosis of TCs appears to be an initial event that leads to the release of DAMPs and the induction of NETosis. NETs and NETs-derived DAMPs such as histones and DNA act as mediators of necroinflammation to induce further injury of TCs and further NETs formation. The cycle of TC deaths and NETs formation exacerbates kidney injury and induces remote organ injury. Conversely, use of anti-histone agents, such as anti-histone antibodies, alone or in combination with PAD inhibitors, can ameliorate the remote organ injury consequent to AKI.

Example 2. Effect of Histone-Neutralizing Agents on Vascular Necrosis in Severe Glomerulonephritis Severe glomerulonephritis involves cell necrosis as well as NETosis, a programmed neutrophil death leading to expulsion of nuclear chromatin leading to neutrophil extracellular traps (NETs). We speculated on a role of the dying cell's and NET's histone component in necrotizing glomerulonephritis. Histones from calf thymus or histones released by neutrophils undergoing NETosis killed glomerular endothelial cells, podocytes, and parietal epithelial cells in a dose-dependent manner. As discussed below, this effect was prevented by histone-neutralizing agents such as anti-histone IgG, activated protein C, or heparin.

Histone toxicity on glomeruli ex vivo was TLR2/4-dependent. Lack of TLR2/4 attenuated intra-arterial histone injection-induced renal thrombotic microangiopathy and glomerular necrosis in mice. Anti-GBM glomerulonephritis involved NET formation and vascular necrosis. Pre-emptive anti-histone IgG administration significantly reduced all aspects of glomerulonephritis, i.e. vascular necrosis, podocyte loss, albuminuria, cytokine induction, recruitment and activation of glomerular leukocytes as well as glomerular crescent formation.

To evaluate the therapeutic potential of histone neutralization we treated mice with established glomerulonephritis with three different histone-neutralizing agents. Anti-histone IgG, recombinant activated protein C, and heparin all abrogated severe glomerulonephritis, suggesting that histone-mediated glomerular pathology is not an initial but rather a subsequent event in necrotizing glomerulonephritis. Together, histone release during glomerulonephritis elicits cytotoxic and immunostimulatory effects. Neutralizing extracellular histones is therapeutic in severe experimental glomerulonephritis.

Materials and Methods

Mice and Anti-GBM Nephritis Model—

C57BL/6 mice were procured from Charles River (Sulzfeld, Germany). 6-8 week old mice received an intravenous injection of 100 μl of anti-GBM serum (sheep anti-rat glomeruli basement membrane serum procured from Probetex INC, PTX-001). Urine samples were collected at different time points after antiserum injection to evaluate the functional parameters of kidney damage. On day 7 the mice were sacrificed by cervical dislocation to collect plasma and kidney tissue. Kidneys were kept at −80° C. for protein isolation and in RNALATER® solution at −20° C. for RNA isolation. A part of the kidney was also kept in formalin to be embedded in paraffin for histological analysis (Teixeira et al., 2005, *Kidney Int* 67:514B). We treated groups of mice either with 20 mg/kg, i.p. control IgG or anti-histone antibody (clone BWA-3) to neutralize the effects of extracellular histones.

Assessment of Renal Pathology—

Renal sections of 2 μm were stained with periodic acid-Schiff reagent. Glomerular abnormalities were scored in 50 glomeruli per section by a blinded observer. The following criteria were assessed in each of the 50 glomeruli and scored as segmental or global lesions if less or more than 50% of the glomerular tuft were affected by focal necrosis and capsule adhesions. Cellular crescents were assessed separately when more than a single layer of PECs were present around the inner circumference of Bowman's capsule. Immunostaining was performed as described using the following primary antibodies: for WT-1/nephrin, neutrophils (Serotec, Oxford, UK), Mac-2 (Cedarlane, Ontario, Canada), TNF-α (Abcam, Cambridge, UK) and fibrinogen (Abcam, Cambridge, UK). Stained glomerular cells were quantified in 50 glomeruli per section.

Electron Microscopy—

Kidney tissues and endothelial cell monolayers were fixed in 2.0% paraformaldehyde/2.0% glutaraldehyde, in 0.1M sodium phosphate buffer, pH 7.4 for 24 h, followed by 3 washes ×15 min in 0.1m sodium phosphate buffer, pH 7.4 and distilled water. For transmission EM kidneys were post-fixed, in phosphate cacodylate-buffered 2% OsO4 for 1 h, dehydrated in graded ethanols with a final dehydration in propylene oxide and embedded in Embed-812 (Electron Microscopy Sciences, Hatfield, Pa.). Ultrathin sections (~90-nm thick) were stained with uranyl acetate and Venable's lead citrate. For scanning EM, after rinsing in distilled $H_2O$, cells on coverslips were treated with 1% thiocarbohydrazide, post-fixed with 0.1% osmium tetroxide, dehydrated in ethanol, mounted on stubs with silver paste and critical-point dried before being sputter coated with gold/palladium. Specimens were viewed with a JEOL model 1200EX electron microscope (JEOL, Tokyo, Japan).

Immunohistochemistry of Human Tissues—

Formalin-fixed paraffin-embedded sections of renal biopsies from five subjects with ANCA-positive RPGN, newly diagnosed in 2013, were drawn from the files of the Institute of Pathology at the Ludwig-Maximilians-University of Munich. The renal biopsies were fixed in 4% PBS-buffered formalin solution and embedded in paraffin. Biopsies contained normal glomeruli and glomeruli exhibiting cellular, fibrocellular or fibrous crescents. Controls consisted of normal kidney tissue from tumor nephrectomies. TLR2 and TLR4 expression was assessed by using specific antibodies (TLR2-LS Bio, Seattle, Wash., TLR4-Novus, Littleton, Colo.).

In-Vitro Models

Cytotoxicity Assay—

Mouse glomerular endothelial cells (GEnC (46)), podocytes (47)), and parietal epithelial cells (PECs, (48)) were cultured in 96 well plates with RPMI media without FCS and PS and allowed to adhere overnight. The cells were stimulated with the different concentrations of total calf thymus histones (10, 20, 30, 40, 50 and 100 μg/ml) with or without histone antibody for another 18-20 h. Cytotoxicity assay was performed using Promega CELLTITER 96® non-radioactive cell proliferation assay (MTT Assay Kit, Mannheim, Germany). Glomerular cells were also incubated with histones with or without anti-histone IgG, heparin and/or aPC. LDH assay using cytotoxicity detection kit (Roche Diagnostics, Mannheim, Germany) was used to assess cell death.

Podocyte Detachment Assay—

Podocytes were grown at 33° C. using modified RPMI media in the presence of IFN-γ in collagen coated 10 cm dishes and $8 \times 10^4$ cells were seeded and allowed to differentiate as podocytes at 37° C. for two weeks in collagen plates without IFN-γ. Once the monolayers of podocytes were differentiated, the cells were treated with either histones or GBM antiserum with or without histone antibody and allowed to sit for 18 h. Detached cells which are present in supernatant were manually counted using an hemocytometer. Adhered cells were trypsinised and counted manually to calculate the percentage of cells detached.

In-Vitro Tube Formation Assay—

Matrigel was thawed overnight at 4° C. to make it liquid. After 10 μl per well of μ-slide angiogenesis (IBIDI, Munich, Germany) was added, the gel was allowed to solidify at 37° C. GEnCs were seeded at $1 \times 10^4$ cells/well and stimulated with VEGF and b-FGF as positive control or with histones with or without anti-histone antibody. Tube formation as a marker of angiogenesis was assessed by light microscopy by taking a series of pictures at 0 h, 4 h 8 h and 24 h (49).

NETosis Assay—

Neutrophils were isolated from healthy mice by dextran sedimentation and hypotonic lysis of RBCs. Neutrophil extracellular traps (NETs) were induced in-vitro by adding TNF-α (Immunotools, Friesoythe, Germany) or phorbol 12-myristate 13-acetate (PMA, Sigma-Aldrich, Mo., USA) for 12 h in with or without anti-histone antibody. Endothelial cell death was assessed by MTT assay and immunofluorescence staining for histones (BWA-3 clone), neutrophil elastase (ABCAM®, Cambridge, UK) and 4',6-Diamidin-2-phenylindol (DAPI, Vector labs, Burlingame, Calif.) after fixing with acetone.

BMDCs and J774 Macrophages—

Bone marrow cells were isolated from healthy mouse and plated at $1 \times 10^6$ cells per well and differentiated into BMDCs in the presence of GM-CSF (Immunotools). J774 macrophage cells were grown in RPMI media, plated at $1 \times 10^6$ cells per well, and stimulated with different doses of histones with or without anit-histone antibody for 18 h. Supernatants were collected for TNF-α (Bio Legend, San Diego, Calif.) and IL-6 Elisa (BD Biosciences, San Diego, Calif.) determination. Flow cytometry for the activation markers CD40, CD103 and CD86 (BD) was also performed.

Flow Cytometry—

Flow cytometric analysis of cultured and renal immune cells was performed on a FACSCALIBUR™ flow cytometer (BD) as described (Lech et al., 2009, *J Immunol* 183:4109). Every isolate was incubated with binding buffer containing either anti-mouse CD11c, CD11b, CD103, F4/80, and CD45 antibodies (BD) for 45 min at 4° C. in the dark were used to detect renal mononuclear phagocyte populations. Anti-CD86 (BD) was used as an activation marker. Anti-CD3 and CD4 (BD) were used to identify the respective T-cell populations.

RNA Preparation and Real-Time RT-PCR—

Reverse transcription and real time RT-PCR from total renal RNA was prepared as described (Patole et al., 2007, *J Autoimmun* 29:52). SYBR Green Dye detection system was used for quantitative real-time PCR on a Light Cycler 480 (Roche, Mannheim, Germany). Gene-specific primers (300 nM, Metabion, Martinsried, Germany) were used as follows: Reverse and forward primers respectively 18s: AGGGCCT-CACTAAACCATCC (SEQ ID NO:36) and GCAATTAT- TCCCCATGAACG (SEQ ID NO:37), TNF-α: CCAC-CACGCTCTTCTGTCTAC (SEQ ID NO:38) and AGGGTCTGGGCCATAGAACT (SEQ ID NO:39), Fibrinogen (FGL-2): AGGGGTAACTCTGTAGGCCC (SEQ ID NO:40) and GAACACATGCAGTCACAGCC (SEQ ID NO:41), WT-1: CATCCCTCGTCTCCCATTTA (SEQ ID NO:42) and TATCCGAGTTGGGGAAATCA (SEQ ID NO:43), CD44: AGCGGCAGGTTACATTCAAA (SEQ ID NO:44) and CAAGTTTTGGTGGCACACAG (SEQ ID NO:45). Controls consisting of ddH$_2$O were negative for target and housekeeping genes.

Statistical Analysis

Data were expressed as mean±standard error of the mean (SEM). Comparison between groups was performed by two-tailed t-test or ANOVA. A value of p<0.05 was considered to be statistically significant. All statistical analyses were calculated using Graph Pad Prism (GraphPad).

Example 3. Glomerular TLR2 and TLR4 Expression in Severe Human Glomerulonephritis We first asked whether the TLR2 and TLR4 (Allam et al., 2012, *J Am Soc Nephrol* 23:1375) extracellular histones were expressed in the healthy and diseased glomeruli. TLR2/4 immunostaining of normal human kidney showed a weak granular positivity in all glomerular cells. TLR4 positivity was clearly noted in glomerular endothelial cells (not shown). In addition, TLR2 was strongly positive in the cytoplasm of epithelial cells of the proximal and distal tubule, while this was less prominent for TLR4 (not shown). Immunostaining of kidney biopsies of patients with ANCA-associated necrotizing and crescentic GN revealed prominent positivity also in PECs along the inner aspect of Bowman's capsule (not shown). As glomerular crescents are largely formed by PECs (Smeets et al., 2009, *J Am Soc Nephrol* 20:2593; Smeets et al., 2009, *J Am Soc Nephrol* 20:2604), glomerular crescents displayed TLR2 and TLR4 positivity (not shown). Thus, the cells of the normal glomerulus express TLR2/4 and PECs induce these TLRs in crescentic GN.

Example 4. Anti-Histone IgG Prevents Histone Toxicity on Glomerular Cells

Histones were previously shown to be toxic to pulmonary endothelial cells in vitro and in vivo (Xu et al., 2009, *Nat Med* 15:1318; Abrams et al., 2013, *Am J Respir Crit Care Med* 187:160). We tested this effect on cultured glomerular endothelial cells and found that a total histone preparation was cytotoxic in a dose-dependent manner. Anti-histone IgG derived from the BWA-3 hybridoma is known to neutralize the toxic and immunostimulatory effect of extracellular histones (Xu et al., 2009, *Nat Med* 15:1318; Xu et al., 2011, *J Immunol* 187:2626; Monestier et al., 1993, *Mol Immunol* 30:1069. Anti-histone IgG almost entirely prevented histone toxicity on glomerular endothelial cells up to a histone concentration of 30 µg/ml (not shown). Anti-histone IgG also prevented histone-induced GEnC microtubule destruction in angiogenesis assays (not shown). Histone-induced toxicity was also evident in cultured podocytes and PECs albeit at much higher histone concentrations compared to the toxic dose required to kill endothelial cells (not shown). Anti-histone-IgG also significantly reduced histone-induced detachment of cultured podocytes (not shown). Thus, extracellular histones are toxic to glomerular cells, which toxicity can be blocked by anti-histone IgG.

Example 5. Neutrophil Extracellular Traps Kill Glomerular Endothelial Cells through Histone Release In severe GN neutrophils undergo NETosis, which deposits nuclear chromatin within the glomerular capillaries (Kessenbrock et al., 2009, *Nat Med* 15:623). Immunohistochemical staining showed nuclear chromatin release from netting neutrophils, including the spread of histones outside the dying cells (not shown). Neutrophils undergoing TNF-α- or PMA-induced NETosis on monolayers of glomerular endothelial cells destroyed this monolayer by inducing endothelial cell death, while TNF or PMA alone did not (not shown). This NETosis-related endothelial cell toxicity was entirely prevented by anti-histone IgG (not shown). We conclude that netting neutrophils damage glomerular endothelial cells via the release of histones.

Example 6. Histones Need TLR2/4 to Trigger Glomerular Necrosis and Microangiopathy Whether glomerular toxicity of extracellular histones is TLR2/4-dependent is not clear. To answer this question we exposed glomeruli isolated from wild type and Tlr2/4-deficient mice to histones ex vivo. Histones exposure was cytotoxic to glomeruli, a process that was entirely prevented using glomeruli from Tlr2/4-deficient mice (not shown). Lack of TLR2/4 also prevented IL-6 and TNF expression in histone-exposed glomeruli (not shown). We also studied the effects of extracellular histones on glomeruli in vivo. Because intravenous histone injection kills mice immediately by pulmonary microvascular injury (Xu et al., 2009, *Nat Med* 15:1318), we injected histones directly into the left renal artery in anaesthetized mice. Unilateral histone injection caused glomerular lesions within 24 hours ranging from minor endothelial fibrinogen positivity to thrombotic microangiopathy and global glomerular necrosis (not shown). The contralateral kidney remained unaffected (not shown). Histone injection into the renal artery of Tlr2/4-deficient mice showed significantly reduced glomerular lesions and fibrinogen positivity (not shown). These results demonstrate that extracellular histones induce glomerular injury in a TLR2/4-dependent manner.

Example 7. Extracellular Histones Contribute to Severe Glomerulonephritis

Based on these results we speculated that intrinsic histone release may also contribute to severe GN in vivo. To address this question we applied the same neutralizing anti-histone IgG as used in vitro that demonstrated the functional contribution of extracellular histones in lethal endotoxemia (Xu et al., 2009, *Nat Med* 15:1318). Mice were injected i.p. with 20 mg/kg anti-histone IgG or with 20 mg/kg control IgG 24 hours before the intravenous injection of a GBM antiserum raised in sheep. At the end of the study at day 7 only sheep IgG but no mouse IgG deposits were found in glomeruli, excluding any autologous anti-sheep IgG response contributing to glomerulonephritis (not shown). Anti-histone IgG significantly reduced blood urea nitrogen (BUN) and serum creatinine levels following GBM antiserum injections (not shown). This was associated with a significant reduction in crescent formation and global glomerular pathology with less severe lesions 7 days after antiserum injection (not shown). Myeloperoxidase (MPO) immunostaining visualized NETs inside glomeruli, which was associated with focal loss of endothelial CD31 positivity as a marker of glomerular vascular injury (not shown). Anti-histone IgG did not affect extracellular positivity but maintained CD31+ vasculature (not shown), indicating a protective effect on NET-related vascular injury.

Because histones were toxic to glomerular endothelial cells and podocytes in vitro, we assessed the glomerular capillary ultrastructure by transmission electron microscopy. In control mice with crescentic glomeruli there was severe glomerular damage with fibrin deposits replacing large glomerular segments (fibrinoid necrosis). The capillary loops showed extensive GBM splitting and thinning, prominent endothelial cell nuclei, massive subendothelial edema with closure of the endothelial fenestrae, and obliteration of the capillary lumina. Subendothelial transudates (leaked serum proteins) and luminal platelets and neutrophils were also noted. Severe podocyte injury with diffuse foot process effacement, reactive cytoplasmic changes and detachment from the GBM were apparent (not shown).

In contrast, glomeruli of mice injected with anti-histone IgG showed restored endothelial fenestrations, flat appearing endothelial cells and preserved podocytes with intact foot processes (not shown). WT-1/nephrin co-immunostaining revealed that anti-histone IgG largely prevented podocyte loss in antiserum-induced GN (not shown). This was consistent with significant reduction of albuminuria on day 7 following antiserum injection as compared to control IgG-treated mice (not shown). These results demonstrate that extracellular histones induce severe GN by causing glomerular vascular injury and podocyte loss, accompanied by proteinuria. They also demonstrate the efficacy of anti-histone antibody in preventing glomerular damage in glomerulonephritis.

Example 8. Extracellular Histones Drive Glomerular Leukocyte Recruitment and Activation Infiltrating leukocytes are not only a documented source of extracellular histones in severe GN (Kessenbrock et al., 2009, *Nat Med* 15:623) but also important effector cells (Kurts et al., 2013, *Nat Rev Immunol* 13:738). For example, in GBM antiserum-exposed glomerular endothelial cells, histone exposure triggered CXCL2 expression (not shown). In vivo, anti-histone IgG significantly reduced the numbers of glomerular neutrophils and macrophages as quantified by immunostaining (not shown). Flow cytometry of renal cell suspensions allowed us to better distinguish renal mononuclear phagocyte populations. Anti-histone IgG significantly reduced the numbers of activated (MHC II+) F4/80+ cells as well as of activated (CD86+) CD11b/CD103+ cells, and of CD4+ dendritic cells (not shown). In fact, histones dose-dependently induced activation markers like WICK CD40, CD80, and CD86 also in cultured bone marrow derived macrophages (BMDCs), which was entirely prevented with anti-histone IgG (not shown). Taken together, extracellular histones trigger glomerular leukocyte recruitment and activation, which can be blocked with anti-histone IgG in vitro and in vivo.

Example 9. Extracellular Histones Trigger Intraglomerular TNF-α Release and Thrombosis Activated mononuclear phagocytes are also an important source of pro-inflammatory cytokines in glomerular disease. Among these, TNF-α particularly contributes to podocyte loss, proteinuria, and glomerulosclerosis (Ryu et al., 2012, *J Pathol* 226:120). Because anti-histone IgG entirely prevented histone-induced TNF-α secretion in cultured macrophages and dendritic cells (not shown), we next assessed glomerular TNF-α expression. Immunostaining displayed robust TNF-α positivity within the glomerular tuft, which not only localized in infiltrating cells but also in inner and outer aspect of the glomerular capillaries (not shown). Anti-histone IgG strongly reduced glomerular TNF-α positivity, which was consistent with the corresponding renal mRNA expression levels (not shown). TNF-α is not only an inducer of NETosis but also triggers a prothrombotic activation of (glomerular) endothelial cells and intravascular fibrin formation (32-34). Our GN model displayed global fibrinogen positivity within glomerular capillaries, which was almost entirely prevented with anti-histone IgG (not shown). Also fibrinogen mRNA levels were reduced in the anti-histone IgG group (not shown). These results show that extracellular histones trigger intraglomerular TNF-α production and microthrombi formation within glomerular capillaries.

Example 10. Extracellular Histones Activate Parietal Epithelial Cells via TLR2/4

Mitogenic plasma proteins leaking from injured glomerular capillaries cause PEC hyperplasia and glomerular crescent formation (Ryu et al., 2012, *J Pathol* 228:482; Smeets et al., 2009, *J Am Soc Nephrol* 20:2593; Smeets et al., 2009, *J Am Soc Nephrol* 20:2604). In fact, in antiserum-induced GN glomerular crescents were positive for claudin-1/WT-1 positive cells (not shown), where claudin-1 identifies PECs and WT-1 marks PEC activation (Shankland et al., 2013, *Curr Opin Nephrol Hypertens* 22:302. PECs cultured in 10% serum started proliferating upon histone exposure (not shown). Having shown that TLR2 and -4 are upregulated in PECs during severe human GN, we questioned whether extracellular histones drive PEC activation in a TLR2/4-dependent manner.

The mitogenic effect of histones to serum exposed PECs was entirely blocked by TLR2/4 inhibition (not shown). TLR2/4 inhibition also blocked histone-induced expression of CD44 and WT-1 in PECs (not shown). Previous reports documented that heparin and recombinant activated protein C (aPC) also block histone toxicity (Xu et al., 2009, *Nat Med* 15:1318; Wildhagen et al., 2013, *Blood* 123:1098). As such, the protective effect on PEC activation was shared by anti-histone IgG, heparin or activated protein C (aPC) (not shown), the latter two suppressing histone cytotoxicity on glomerular endothelial cells just like anti-histone IgG (not shown). Thus, extracellular histones activate PECs in a TLR2/4-dependent manner, a process that may act synergistically with other triggers of PEC hyperplasia during crescent formation and that can be blocked by anti-histone IgG, aPC or heparin.

Example 11. Delayed Onset of Histone Neutralization Still Improves Severe GN

The results of pre-emptive histone neutralization proved their pathogenic contribution to severe GN. We mext examined whether histone neutralization could be therapeutic in established disease. Anti-histone IgG, heparin, and aPC all completely blocked histone toxicity on glomeruli ex vivo (not shown). In another series of experiments we initiated anti-histone IgG, heparin, and aPC treatments 24 hours after GBM antiserum injection, a time point where massive proteinuria and elevated BUN were already established (not shown). All these treatments consistently and significantly reduced plasma creatinine levels, proteinuria, and podocyte loss at day 7 (not shown). Histone blockade also significantly reduced the percentage of glomeruli with global lesions or halted damage (not shown). Glomerular crescents were reduced by 80% (not shown) and so were features of secondary tubular injury (not shown). This was associated with less glomerular neutrophil and macrophage infiltrates as well as a significant reduction of intrarenal leukocyte subpopulations as well as their activation, as identified by flow cytometry (not shown). Thus, delayed onset of histone blockade with anti-histone IgG, heparin or aPC protects from renal dysfunction and structural injury during severe GN.

Example 12. Summary of Effects of Histone Neutralization on Necrosis in Glomerulonephritis We hypothesized that extracellular histones elicit toxic and immunostimulatory effects on glomerular cells during necrotizing and crescentic GN. The data reported in the Examples above confirm this concept and also demonstrate that histone neutralization continues to be protective when it commences after disease onset, which implies a potential therapeutic use of histone neutralizing agents in severe GN.

Necrotizing and crescentic GN, such as seen in ANCA-associated renal vasculitis or anti-GBM disease, is associated with neutrophil-induced glomerular injury. First discovered in 2004, NETosis is a regulated form of neutrophil death that supports killing of extracellular bacteria (Brinkmann et al., 2004, *Science* 303:1532). NETosis is not limited to antibacterial host defence but also occurs in sterile forms of inflammation, because it can be triggered by pro-inflammatory cytokines such as TNF-α. Our in vitro studies show that TNF-α is a sufficient stimulus to trigger NETosis-driven injury of glomerular endothelial cells. NETosis releases many aggressive proteases, oxygen radicals, and potential DAMPs into the extracellular space that have the potential to drive vascular injury in the glomerulus.

Our data demonstrate an essential role of histones in this context. The endothelial toxicity of extracellular histones was first described in a seminal paper on sepsis, where early lethality was due to microvascular endothelial cell injury in the lung (Xu et al., 2009, *Nat Med* 15:1318). Subsequent reports further explored the thrombogenic potential of extracellular histones via direct activation of endothelial cells as well as of platelets (Abrams et al., 2013, *Am J Respir Crit Care Med* 187:160; Saffarzadeh et al., 2012, *PLoS One* 7:e32366; Semeraro et al., 2011, *Blood* 118:1952; Ammollo et al., 2011, *J Thromb Haemost* 9:1795; Fuchs et al., 2011, *Blood* 118:3708; Fuchs et al., 2010. *Proc Natl Acad Sci USA* 107:15880).

In infection and sepsis models, NETosis is the most likely source of extracellular histones. However, in mechanical trauma, toxic liver injury, cerebral stroke, and post-ischemic renal tubular necrosis histones are also released from dying tissue cells (Allam et al., 2014, *J Mol Med*, 92:465; Allam et al., 2012, *J Am Soc Nephrol* 23:1375). The source of extracellular histones in our in vivo model could be dying glomerular cells as well as netting neutrophils, which we identified by MPO staining in situ. Histone blockade had no effect on NETosis per se but rather worked on the related vascular injury inside the glomerulus.

Our in vitro and in vivo data clearly demonstrate that extracellular histones are toxic to glomerular cells and promote glomerular injury in healthy mice upon intra-arterial injection or during severe antiserum-induced GN. The mechanisms of histone toxicity are not entirely clear but are thought to be due to their strong basic charge (Gillrie et al., 2012, *Am J Pathol* 180:1028). While histones basic charge is needed inside the nucleus to neutralize acidic residues of the DNA, outside the cell, it has the capacity to damage cell membranes (Gillrie et al., 2012, *Am J Pathol* 180:1028). The polyanion heparin blocks this charge effect of histones, which may explain its antagonistic effect on histone toxicity in vitro and in vivo. However, we and others discovered that histones elicit also DAMP-like activity by activating TLR2, TLR4, and NLRP3 (Semeraro et al., 2011, *Blood* 118:1952; Allam et al., 2012, *J Am Soc Nephrol* 23:1375; Allam et al., 2013, *Eur J Immunol* 43:3336; Huang et al., 2013, *J Immunol* 191:2665; Xu et al., 2011, *J Immunol* 187:2626), which is another pathway of how extracellular histones trigger sterile inflammation.

Because TLR2 and TLR4 (but not NLRP3) are known to induce glomerular injury in the heterologous anti-GBM GN model (Brown et al., 2006, *J Immunol* 177:1925; Brown et al., 2007, *J Am Soc Nephrol* 18:1732; Lichtnekert et al., 2011, *PLoS One* 6:e26778; Lichtnekert et al., 2009, *Am J Physiol Renal Physiol* 296:F867), we further explored the histone-TLR2/4 axis. Tlr2/4-deficient glomeruli were protected from histone-induced injury ex vivo and in vivo, implying that the histone-related glomerular injury relates to the TLR2/4-dependent DAMP effect. In particular the presence of serum turned the cytotoxic effect of histones on PECs into PEC proliferation, which was entirely TLR2/4 dependent. Although PEC necrosis can be followed by excessive PEC recovery leading to PEC hyperplasia and crescent formation (Sicking et al., 2012, *J Am Soc Nephrol* 23:629), concomitant plasma leakage and histone release provide additional mitogenic stimuli during severe GN (Ryu et al., 2012, *J Pathol* 228:382).

Our proof-of-concept experiments were based on pre-emptive histone neutralization with anti-histone IgG. To explore a potential efficacy of histone blockade in severe GN we also applied three different modes of histone inactivation following GN induction. Delayed onset of anti-histone IgG was equally protective as pre-emptive therapy in terms of glomerular injury, proteinuria, and serum creatinine levels. The same applies to heparin treatment, which confirms previously published results in GN models (Floege et al., 1993, *Kidney Int* 43:369). Our data clearly show that heparin inhibits the direct toxic effects of histones on glomerular endothelial cells, which is consistent with the results of other investigators in other cell types (Hirsch, 1958, *J Exp Med* 108:925; Ammollo et al., *J Thromb Haemost* 9:1795; Fuchs et al., 2010, *Proc Natl Acad Sci USA* 107:15880). As previously reported aPC degrades extracellular histones (Xu et al., 2009, *Nat Med* 15:1318. In the current studies it was equally effective as anti-histone IgG and heparin in abrogating extracellular histone toxicity in vitro and severe GN in vivo.

Together, NETosis releases histones into the extracellular space where they have toxic effects on glomerular endothelial cells and podocytes. Extracellular histone-induced glomerular injury is partially due to TLR2/4. Pre-emptive as well as delayed onset of histone neutralization either by anti-histone IgG, recombinant aPC or heparin abrogates all aspects of GBM antiserum-induced severe GN. We conclude that extracellular histones represent a novel therapeutic target in severe GN.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

What is claimed is:

1. A method of treating remote organ injury induced by acute kidney injury, comprising administering to a subject with acute kidney injury at least one anti-histone agent selected from the group consisting of an anti-histone antibody, activated protein C and heparin.

2. The method of claim 1, wherein the anti-histone antibody binds to a human histone selected from the group consisting of histone H2B, histone H3 and histone H4.

3. The method of claim 2, wherein the anti-histone antibody is an anti-histone H4 antibody.

4. The method of claim 2, wherein the anti-histone antibody is selected from the group consisting of BWA-3, LG2-1 and LG2-2.

5. The method of claim 1, wherein administration of anti-histone antibody reduces post-ischemic tubular necrosis, renal dysfunction, NET formation and lung injury induced by AKI.

6. The method of claim 1, wherein the anti-histone antibody is a chimeric, humanized or human antibody.

7. The method of claim 1, wherein the subject is a human subject.

8. The method of claim 1, wherein administration of the anti-histone agent is effective to prevent remote organ injury in subjects with acute kidney injury.

9. The method of claim 1, wherein the anti-histone antibody or fragment thereof is not conjugated to a therapeutic agent.

10. The method of claim 1, wherein the anti-histone antibody or fragment thereof is conjugated to at least one therapeutic agent.

11. The method of claim 10, wherein the therapeutic agent is selected from the group consisting of a second antibody, a second antibody fragment, a radionuclide, an immunomodulator, an anti-angiogenic agent, a pro-apoptotic agent, a cytokine, a chemokine, a drug, a toxin, a hormone, an siRNA and an enzyme.

12. The method of claim 1, wherein the anti-histone antibody or fragment thereof is a fusion protein.

13. The method of claim 1, wherein the remote organ is lung or heart.

* * * * *